United States Patent
Ji et al.

(10) Patent No.: US 11,034,981 B2
(45) Date of Patent: Jun. 15, 2021

(54) PRODUCTION OF FATTY ALCOHOLS IN RHODOSPORIDIUM

(71) Applicant: TEMASEK LIFE SCIENCES LABORATORY LIMITED, Singapore (SG)

(72) Inventors: Lianghui Ji, Singapore (SG); Yanbin Liu, Singapore (SG); Chong Mei John Koh, Singapore (SG); Sihui Amy Yap, Singapore (SG); Si Te Ngoh, Singapore (SG)

(73) Assignee: TEMASEK LIFE SCIENCES LABORATORY LIMITED, Singapore (SG)

( * ) Notice: Subject to any disclaimer, the term of this patent is extended or adjusted under 35 U.S.C. 154(b) by 0 days.

(21) Appl. No.: 16/484,322

(22) PCT Filed: Jan. 29, 2018

(86) PCT No.: PCT/SG2018/050045
§ 371 (c)(1),
(2) Date: Aug. 7, 2019

(87) PCT Pub. No.: WO2018/147799
PCT Pub. Date: Aug. 16, 2018

(65) Prior Publication Data
US 2019/0360003 A1 Nov. 28, 2019

Related U.S. Application Data

(60) Provisional application No. 62/455,669, filed on Feb. 7, 2017.

(51) Int. Cl.
*C12P 7/04* (2006.01)

(52) U.S. Cl.
CPC .......... *C12P 7/04* (2013.01); *C12Y 102/01042* (2013.01); *C12Y 203/0102* (2013.01); *C12Y 203/01026* (2013.01); *C12Y 203/01158* (2013.01)

(58) Field of Classification Search
CPC ............... C12P 7/04; C12Y 102/01042; C12Y 203/0102; C12Y 203/01026; C12Y 203/01158; C12Y 203/01; C12Y 203/01062; C12N 9/0008; C12N 9/1029; C12N 1/16
See application file for complete search history.

(56) References Cited

U.S. PATENT DOCUMENTS

2016/0090612 A1  3/2016  Hattendorf et al.

FOREIGN PATENT DOCUMENTS

| WO | 2012169969 A1 | 12/2012 |
| WO | 2016039685 A1 | 3/2016 |
| WO | 2016128602 A1 | 8/2016 |
| WO | 2016159869 A1 | 10/2016 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Sadowski et al., Current Opinion in Structural Biology 19:357-362, 2009.*
Zhou et al., Cell Mol Life Sci 63(19-20):2260-2290, 2006.*
Kozak, M., Gene 234:187-208, 1999.*
Copeland et al., Gen Bank accession No. YP_959486 Dec. 18, 2014.*
International Search Report and Written Opinion in PCT/SG2018/050045 dated Mar. 20, 2018, 16 pages.
Fillet, S., et al., "Fatty alcohols production by oleaginous yeast," J Ind Microbial Biotechnol, 2015, vol. 42, 1463-1472.
Liu, Y., et al., "Developing a set of strong intronic promoters for robust metabolic engineering in oleaginous *Rhodotorula* (Rhodosporidium) yeast species" Microb Cell Fact, 2016, 15:200, 9 pages.
Supplementary European Search Report issued in corresponding European Application No. EP 18750679.5, dated Mar. 25, 2021, 12 pages.
Wang et al, "Exploring fatty alcohol-producing capability of Yarrowla Ilpolytica11", Biotechnol Biofuels 107, vol. 9, No. 107, Dec. 20, 2016, pp. 1-10.
Sitepu et al., "Manipulation of culture conditions alters lipid content and fatty acid profiles of a wide variety of known and new oleaginous yeast species", Bioresource Technology, vol. 144, 28 Jun. 28, 2013, pp. 360-369.
Thakur et al., "Estimation of intracellular lipids by the measurement of absorbance of yeast cells stained with Sudan Black B", Enzyme Microb. Technol., vol. 11, Apr. 1, 1989, pp. 252-254.
Amaretti et al., "Single cell oils of the cold-adapted oleaginous yeast Rhodotorula glacialis DBVPG 4785", Microbial Cell Factories, vol. 9, Sep. 23, 2010, pp. 1-6.

* cited by examiner

Primary Examiner — Delia M Ramirez
(74) Attorney, Agent, or Firm — Rothwell, Figg, Ernst & Manbeck, P.C.

(57) ABSTRACT

The present invention relates to the field of fungal production fatty alcohols. More specifically, the present invention relates to genetically modified host cells, nucleic acid constructs and culture medium for the production of fatty alcohols in *Rhodosporidium*.

18 Claims, 12 Drawing Sheets

Specification includes a Sequence Listing.

SEQUENCE LISTING

```
<160> NUMBER OF SEQ ID NOS: 62

<210> SEQ ID NO 1
<211> LENGTH: 1856
<212> TYPE: DNA
<213> ORGANISM: Rhodosporidium toruloides
```

<400> SEQUENCE: 1

```
atgggccagc aggcgacgct cgaggagctg tacacacgct cagaaatctc caagatcaag      60
caagtcgagc cagctcttct cctcaccacc ccacaacata ccccgcagcc cacgacagct     120
ctcccacagc acccacagcc tgctgaccag ctcgagtgca tccacagatt tgcgcccttt     180
ggcgtcccgc ggtcgcgccg gctgcagacg ttctccgtct ttgcctggac gacggcactg     240
cccatcctac tcggcgtctt cttcctgctc tggtgcgtca ggcttggcgt ggattgggag     300
tagcgggcga ctcagctgac ttgcgcatcc gctccagctc gttcccaccg ctctggccgg     360
ccgtcatcgc ctacctcacc tgggtctttt tcattgacca ggcgccgact cacggtggac     420
gggcgcagtc ttggctgcgg aagagtcgga tatgggtctg gtttgcagga tattatcccg     480
tcaggtgcgt cgtcccgtct gttgcgcgtc ttgcgacctc gctcacgccc aactcgcccg     540
accggctacc tccgaacttc ccgccaacag cttgatcaag gttcgtccac ctttccttca     600
gcttgagtga tctgtagagg agctgcagga tcaagcccaa ccggggagg acctcggagg      660
acgacgccgc tgacttgctc tcctcctaca gagcgccgac ttgccgcctg accggaagta     720
cgtcttcggc tatcatccgc acggcgtcat aggcatgggc ccatcgcca acttcgcgac      780
cgacgcaacc ggcttctcga cactcttccc cggcttgaac cctcacctcc tcaccctcca     840
aagcaacttc aagctcccgc tctatcgcga gttgctgctc ccctcggca tctgctccgt      900
ctcgatgaag agctgccaga acatcctgcg gcaaggtgcg ccagtcattc gaacgggcg      960
gtcgagcgtg aactctgggg atgggaagag ctgaccttct gcctcactcc atccatgcag    1020
gtcctggctc ggctctcacc atcgttgtcg gtggcgcagc cgagagcttg agtgcgcatc    1080
ccggaaccgc cgacctcacg ctcaagcgac gaaaaggatt catcaagctc gcgatccggc    1140
aaggcgccga cctcgtgccc gtcttttcgt tcggcgagaa cgacgtgcgt cctctgctcg    1200
acttccgcta gcgaagccct cgctgacgc tcccggtttc ttccccccaga tcttcggcca    1260
gctgcgaaat gagcgaggga cgcggctgta caagttgcag aagcgtttcc agggcgtatt    1320
cggcttcact ctccgtacgt tgcgccgtgt cgcttcaatc tgtcgagcgt ccagtcgctc    1380
acgcagctac aactcccaca gctctcttct acggtcgggg actcttcaac tgtacgcccg    1440
agtctacgtg actagtctac cgtgggaggc actgaagagc acggctgacg tcccacctct    1500
ccgcgcagat aacgttggct tgatgccgta ccgccatccg atcgtctcgg tcggtgcgtc    1560
cccctcgtc cctcctgacc tgcgggcttc agctaacaat tctcgacgac atctagtcgg     1620
tcgaccaatc tcggtgcagc agaaggacca cccaacgaca gcggatctcg aagaagtcca    1680
ggcgcggtat atcgcagaac tcaagcggtg cgttccagac gtctaccttt gcccgttgtc    1740
tcagactcgg taagacagat cactgacgct cggtcactg gccgcgcagc atctgggaag     1800
actacaagga cgcctacgcc aaaagtcgca cgcgggagct caatattatc gcctga        1856
```

<210> SEQ ID NO 2
<211> LENGTH: 3024
<212> TYPE: DNA
<213> ORGANISM: Rhodosporidium toruloides

<400> SEQUENCE: 2

```
atgagcacag tacggaggcg caaccagccg aagcgcaacg cttctgcgcc cgccaatcag      60
ctcgataccg acgattcttc gcccgctccc tctcgacccg actcgcccga tatcgacaaa     120
gcgccggtgc gagaggtccc actgttcaag cggaggctga aaagggaga tggcaaggtg      180
gaagacccga aggtcattct ggacgagaag acgggcaggg tctccctcga ctttcctagg     240
```

```
acgccatatg accagctcga cctgagtgac tcgttcctcg ccgccttgca cgaggcaccc    300
ttcgagccaa agaagacgtg gacgaagcgg cggagaggct ggttcttttt gggaggattg    360
ctcggtctct gcgcagggtg cgttcgcttt cgttgttgcc gcttaaaatg cgtccagact    420
gacagctcgc tcattcctcc gtgtagctgg atgttcaccg aaggcgaccc actcgcctct    480
ctcgccaacc tcgacctcga cgccttctca tcctgggacc ttcagtcaat cctcgccgac    540
atgccttccc tctccgctct caacgtcacc gaactccttg caccaggtcg tgaatggctg    600
aacagccgag tgaacaactt tgacgtcggg cgagatgcgg ctgcgcgagg gctgaagaag    660
aagcatgcgg tcattctggt gccgggcatc atctcgtcgg tgcgtgcgct gcacttctca    720
catacgcctt acaggctgat gatccccgag tagggtctcg agtcgtggtc gaccaagcca    780
gatgcagctc ccttctttcg ctcgaaggtc tgggcgggaa cctcgatgat tcgtgccgtc    840
atcaagaaca aggaggcttg ggtcaaggcg atcagtctcg acccgtttac tggattggat    900
caggacgggt acaagatccg agctgctcag ggtgtgagtc gactcgttct ccagttcgcg    960
ctgctcgctg attgcatcct tctccagctc gacgccgctt ccgctttcat gcccgggtac   1020
tgtaaatttg ccacttctca gctccttcgc tcgcgatgct gacccttcgt tactcgcagg   1080
gatctggcag aaggtcatcg agaacctcgc cgtcctggac tacgaccaca cgacctgtc    1140 tctcgcatca tacgactggc gacttgcgta cgttgcgctt gatcgctcgc ttgtcttgca   1200
acctgcttac ccttcgcgtc cttcagcttc tacaacctcg aagtccgaga tcgttacttc   1260
tctcggctca aggcttcgat agaattcaac ctcgccatca gcggccagaa gacggttctc   1320
gtctcgcaca gcatgggctc ttcggctctt ctggtgcgtc tcggtttccc aatcttgccg   1380
cacactgtct gacccttgcg tccgttgtag tggttcttca agtaagcttg cctcgccatc   1440
cagcctcgcg aaggattgac tgacggttgc ggacttgcgc aggtgggtcg agtcgccgag   1500
atacggcaac ggcggtccgg actgggtcga gcggcacgtc tcggactggg tcaatgtcgc   1560
gggcacgatg ctcggtgcgc tcaaactctc cttgcgatag atgctctact gaaccctccg   1620
gtcctatcag gcgttccgaa agccatggcc gccctcctct cgggcgagat gcgcgatacg   1680
gtcacgcttt ctcccgccgt catctacctc ctcgaacgct tcttctcccg ctccgaacgc   1740
gccaagctgt tccgctcgtg ggcaggtgcg gcgagcatga tgcttaaggg aggaaacgac   1800
gtctggggcg acgagcagca ggcgccggac gacatggagg aatcggcaat cacgggcgga   1860
aagctgtagt gcgtccgccg tttcatacat ctcacgcatc ggctgacgcc cattcacgca   1920
gctacttccg gcctgagagt cactcgaaca cgtcggaagt gacggaagac accgtccacc   1980
cgaacctgac gctcaacgac gcgaccagct tcctcctaga gaaggtcccg ccgtcctacc   2040
agcagatgct ggcgagtaac ttctcggtgc gtgcactgat acggactgag cgagtgagga   2100
agctcatcga ctcgcgacag ttcggcttcg agcgcgacga gcagcagctc atcaagaaca   2160
acgacgacca ttcgaagtgg agcaatccgc tcgaggtgca gctgccgaag gcgccgtcga   2220
tgaccatcta ctgcttgtac ggcgtcggca aggagactga gcgcgcgtac ttctaccagc   2280
agggtgcggc ccgccctcat cgccgtctgc gagcgttact gacgtcgaca gcggcttact   2340
acaggcggtt acgagcacga cgaaacgccg accgtcaatc tcacagactc gcgggcgtcc   2400
agcctcgaac ccgtttgtct cgagccgaac tgcaccgact cgacgccgcg cccgccgctc   2460
gacctgccgc tccagcgacg cgtatggatc gacggtagcg tgacgatgga cgagaagagc   2520
gtgccgaagg ttaggagcgg agtcgtcttc aacgacggag acgggacggt cagcttgctc   2580
```

| | |
|---|---|
| agtctgggca gcatgtgtgt cgagggctgg aaggtgcgtc tccttcaacg tattctgtga | 2640 |
| gctgaaactg acgagcgccc ctcttagcga cctctgtaca atccggcagg catcaaggtc | 2700 |
| gtcacgcacg agatcttgca tgctccgctc gctttcgatc cgcgaggtgg accaacgact | 2760 |
| gcagaccatg tgcgctctgc ttctacaccg tttcccggct atcagctgac cctcatggtc | 2820 |
| gcaggtcgac atcctcggat cgtgtgtcct cctcgtcgcg ctacctccgc cagacaaggt | 2880 |
| tactgaccag cgcctcgtga ctgctacaga tccgaactga acgacgcgat cctcgacatt | 2940 |
| gctgccggcc aaggcgagcg cgtcaaggac caataccatt cgcggatcca ggacattgcg | 3000 |
| cgcaagatca ggtgggaggg ctga | 3024 |

<210> SEQ ID NO 3
<211> LENGTH: 2788
<212> TYPE: DNA
<213> ORGANISM: Rhodosporidium toruloides

<400> SEQUENCE: 3

| | |
|---|---|
| atggcctcgc tagacccgcc actcccaggc ccagccaacc tcgtcgacga cgccctccga | 60 |
| caccccgact cggcacctcc catcccgccc gactccgctc ctccttcgca tccctcgact | 120 |
| gcgactcagc cctccgcaac ttcgcgcgga cagctttcga ctgcttcgag ctatgcgagc | 180 |
| gatgtgtcga cgagggacgg gacaccggat ctggcgaatg ggtgagttga agcgctggag | 240 |
| gagaagtacc gaggtcttga tcagtgggga ggtgtgtgcg gcgagggagc gagatgcagg | 300 |
| ggctgacggg ctgcgtacgt gcagacaagg cgtaacgacg actattacga ccgtgacagg | 360 |
| caagggcgga aaggcggtca cccagacgtg cgttcccgaa ctcctcctcg tcgattgttc | 420 |
| ctccttcccc ccagtctttg gagactgacg acgttccctc caccgtcctt atcaatttcc | 480 |
| gaccgttctg ctccacgttc cgtgtccccc tcgtccccga cccgcctggc acctcccgct | 540 |
| cttccacctc ctaagcctca cccacgtcgg cgcctcctcc gtcgacgccc gcttctcctc | 600 |
| ctccacctcc tccatcaccc tccgcccat cccagcacgc ggcggcgacc cgaagaagat | 660 |
| caaagtcctc cgttcccgtc gaacccactt cgccccacgc acctcccact tcgaccgcca | 720 |
| caacctgacc tccgcctccg accccttccg cggcctctac actttattct ggatcgtaat | 780 |
| cttcgtcgga gcactcaaga ctgtgtatca tcggtttgcg gagcagggtg ggtggggagg | 840 |
| tgaatggagg tttgcggcgt tgattagtcg tgatgggtgg gtgttggcgg ttagtgatgc | 900 |
| ggtgttggtt agcgcgtcgt tgttgtgcgt gccatatgcc aaggtgcgta cgcgcttgcg | 960 |
| cttcggactc acagctcgaa gctcctgaac tgacggaacg atgctcccgg tctcgctacg | 1020 |
| cagctgctcg tacacggctg gatccggtac cacggcgccg gcgtaatcat ccaacacatc | 1080 |
| tgccaaacgc tctacctcgc catcgcgatc cgctggacct tccaccggtt cgtcctctcc | 1140 |
| cttccccttt cccttcctcc tctcctgtgc tgacgggaca atgagcgcag caactggccc | 1200 |
| tgggtccaaa gcggcttcat gaccctccac gccctctcga tgctcatgaa gatccatagc | 1260 |
| tactgttcgc taaacgggga gctttcggag cggcggagac agttgaggaa ggatgagggg | 1320 |
| aggctggagg aggtgctgga ggagatgggc gggaggagga gggcggagag ggaggcgagg | 1380 |
| gaggagtggg agaggcagtg cggtgaggcg gcgagggcga aggagggcga ggcgggttcg | 1440 |
| cgcgagggaa agaaggagga ggtggcggcc cagtcgtcga cagacgcttc gacttcggct | 1500 |
| ctgtcgtcgg aggatgaggc ggcagcggcg ttgctgcggc atcgacagtc gactgcccga | 1560 |
| cggcgttcca tctcgccatc cgcctctcgc acccactctt cttccgcttc ctcctctcac | 1620 |
| cccgctccct cccgcgccga agagccccaa gaaggcgtcg agacgctcac atggcaccca | 1680 |

```
tccgaccgag tcagcaaact tgctatcgcc atctgcgagg cgaaggacct tctcaccagc    1740
aacggcaaga aacccgtcac gttccccgag aacgtcacgt ttgcgaactt catcgactac    1800
ttgcttgtgc cgacgctggt gtatgagctg aataccctc ggacggactc gtgagtactc     1860
gttcgttcgc ttgggttaca ccttcgagtg gaactgacac gcttcgacgc cgtacagcat    1920
ccgccctctc tacatcctcg aaaagaccct cgcaaccttc ggcaccttct ccatcctcgt    1980
cctgatcgtc gactcgttca tcctccccgt cacctcgcgc accgacaccc cctcttcgg    2040 tttcgtcctc gacctcgcgc tcccgttcac actcgcgtac ctcctcatct tttatgtcat    2100
tttcgagggc gtgtgtaatg ggtttgccga gttgacgagg tttgcggatc ggaacttgtg    2160
cgtgctggcg ctttcttccc tacttgcgaa ttgatccacc taactctctg tcttcccgta    2220
gcttcgacga ctggtggaac tcgtgcacgt tcgatgagtt ctcccgcaaa gtgcgcttcc    2280
gctcctcacc ctcctcatcc taatcccggc taactctttt ctcgtctccg ctcagtggaa    2340
ccgcccagtg cacgccttcc tcctccgcca cgtctacgcc gaaacgatgg cctcgtacaa    2400
gctctcgaag ctctcggccg cgttcgtcac gttcttgttc agcgcttgcg tgcacgaact    2460
cgtcatggcg gtcgtcacga agaagcttcg gctgtatttg ttctcgatgc aggtgcgtgc    2520
gatggctccg tatagtcggc tgcaaaaggg cgaaagccat catatactga tgaacttgga    2580
cgaacgtcgc acagatggcc caactcccgc tcatcatggt cggccgcgcc aagatcttcc    2640
gcaagtaccc tgccctcggc aacgtacgtt ccttcctcct ccttccccg tgcgccggac     2700 tgacgaccct cgccgctcac agctcttctt ctggctcgct cttctctcgg ggttcccgct    2760
tctcgggacg ctgtatttgc ggtactga                                       2788

<210> SEQ ID NO 4
<211> LENGTH: 2250
<212> TYPE: DNA
<213> ORGANISM: Rhodosporidium toruloides

<400> SEQUENCE: 4
atgtccgtct cgacgaacgc tatcttcaag ctcccgaccg tcaagaacga gcccaacttc      60
aactatgcgc caggcagccc cgagcgcgcg gctcttaaga aggccctcgc cgagctcgag     120
gccgccgcgc cgttcgaagt gcccgccttc gtcggcggca aggaggtgcg tcgcacgcct     180
tatcgcggac gcatgtgcat ccgagacggt agctgaccac tatacgtgtg caggtcaagg     240
tctcgggcga gcgcaccgag cagcctatgc cccacaacca caagaaggcg ctctgcacct     300
tcggaacctc gactcctgag ctcgccagcc aggctatcga ggctgcgctc gctgcccagc     360
ctgagtggga ggctatgccc ttcaacgacc gcgccgccat cttcttgagg gtgcgcgaga     420
ccacgctact ttagctgcga acgaatcgct cactcggctc tttgcaggct gccgacctga     480
tcagcggcaa gtaccgtgcc aagatctgcg ctgctaccat gctcggccag ggcaagaacg     540
tctggcaggc cgagattgac gccgctgccg aggtgcgcat ctcggatccg tcgtccgctt     600
cgacagagcc tgaccttcgc tccgaacccg cagctcgccg acttcttccg cttcggcgcc     660
gctcaggtcg agcagctcta cgcgatgcag cccaccgaga actcgcctgg cgtctggaac     720
cgcaccgagt accgcccgct tgagggtttc gtctttgctg tcacccccttc caagtgcgtg     780 cagtcccgtt cttccttgac gtacacagct gacgagtact ttgcagcttc accgctatcg     840
gcggcaacct cgtcgcgct cccgcgctca cggaaacgt cctcgtctgg aagccctcgc      900
ccatggcgac ctactcctcg tggctcgtct tccagatcct ccttgaggcc ggtctcccca     960
```

-continued

```
agaacgtcat ccagttcctc ccctgcccaa acggcgacgc gaccatctcg ctcgttgacc      1020
gcgtcctctc gcaccgcatg ttcgccggtc tccacttcac tggctcgacc cacgtcttcc      1080
gccacctctg gcagaagatc ggcaacaaca tcaacaacta cctcagctac ccccgcatcg      1140
tcggcgagac cggcggaaag aacttccagc tcgtccaccc ctctgccaac gtccgcgctg      1200
ctgtcaccgg tgccatccgc ggtgccttcg agtaccaggg tgcgtgcgac gtctacctta      1260
ctcttcgagt cctaggctga cgctcctccg aatcgcaggc cagaagtgct cggctctctc      1320
gcgtctttac gtcccgaagg gtctgtggga gggcgagggc aagttcaagg agatccttct      1380
ctccgaggtt gccaagatca ctctcggccc cgtcaccgag tttgagcact tcatgggtcc      1440
cgtcatgtgc gtcgcggtcg tcccgaaagt ctcgcttcct ccagctgacc tcgtctcgtc      1500
tcgccccgca gctcgcaggc ttcgttgaca agtgcctca gctacgttga gaaggccaag      1560
caggcaggtg gcgaggtcct cgccggcggc aagggcgacg cgtcgagcgg ttactacgtc      1620
gagccgacca tcatcctgac caaggaccct cgctcgccta ccatggtcga cgagatcttc      1680
ggcccggtcc tcactgttta catctacgag gacgaccagt tcgaggagac gtgcaagttg      1740
atcgaccaga cgacgacgta cgccctcact ggctgcatct tctcggacga ccgtgccgcg      1800
actgtcaagg ccggtgctct cctccgccac gctgcgggta actactacat caacgtgcgt      1860
tgcgcacact tgcttgaccg ttcggcgtag agttggactg gactgtttcg ctgaccttcc      1920
tcgctcccct tcgctccct tcacccgctt tcgcactctt cttgctactg ccaatcatcc      1980 ttccgcccctt tgtacgctct tccggcaaca ggacaagtcg accggtgctg ttgtcggtgc      2040
ccgtaagtct gaacatacat ctcttctcga catcgaccgg cactgacgct cccttcatc      2100 gcagagcctt tcggtggcgc acgcggatcg ggcacgaacg acaaggcggg ctcgatgacg      2160
ttcttcaccc gctggtgcca ccgcggagt gtgaaggaat ccttctgccc gcccgaatct      2220
ttcccttacc cgtcgaacca gcgcgattaa                                      2250
```

```
<210> SEQ ID NO 5
<211> LENGTH: 1257
<212> TYPE: DNA
<213> ORGANISM: Rhodosporidium toruloides
<220> FEATURE:
<221> NAME/KEY: CDS
<222> LOCATION: (34)..(1080)

<400> SEQUENCE: 5
ttcgctcttc acaaccagct cagacgggct gcg atg ggc cag cag gcg acg ctc      54
                                   Met Gly Gln Gln Ala Thr Leu
                                   1               5 gag gag ctg tac aca cgc tca gaa atc tcc aag atc aaa ttt gcg ccc      102
Glu Glu Leu Tyr Thr Arg Ser Glu Ile Ser Lys Ile Lys Phe Ala Pro
        10                  15                  20 ttt ggc gtc ccg cgg tcg cgc cgg ctg cag acg ttc tcc gtc ttt gcc      150
Phe Gly Val Pro Arg Ser Arg Arg Leu Gln Thr Phe Ser Val Phe Ala
25                  30                  35 tgg acg acg gca ctg ccc atc cta ctc ggc gtc ttc ttc ctg ctc tgc      198
Trp Thr Thr Ala Leu Pro Ile Leu Leu Gly Val Phe Phe Leu Leu Cys
40                  45                  50                  55 tcg ttc cca ccg ctc tgg ccg gcc gtc atc gcc tac ctc acc tgg gtc      246
Ser Phe Pro Pro Leu Trp Pro Ala Val Ile Ala Tyr Leu Thr Trp Val
                60                  65                  70 ttt ttc att gac cag gcg ccg act cac ggt gga cgg gcg cag tct tgg      294
Phe Phe Ile Asp Gln Ala Pro Thr His Gly Gly Arg Ala Gln Ser Trp
        75                  80                  85
```

```
ctg cgg aag agt cgg ata tgg gtc tgg ttt gca gga tat tat ccc gtc       342
Leu Arg Lys Ser Arg Ile Trp Val Trp Phe Ala Gly Tyr Tyr Pro Val
         90                  95                 100 agc ttg atc aag agc gcc gac ttg ccg cct gac cgg aag tac gtc ttc       390
Ser Leu Ile Lys Ser Ala Asp Leu Pro Pro Asp Arg Lys Tyr Val Phe
    105                 110                 115 ggc tat cat ccg cac ggc gtc ata ggc atg ggc gcc atc gcc aac ttc       438
Gly Tyr His Pro His Gly Val Ile Gly Met Gly Ala Ile Ala Asn Phe
120                 125                 130                 135 gcg acc gac gca acc ggc ttc tcg aca ctc ttc ccc ggc ttg aac cct       486
Ala Thr Asp Ala Thr Gly Phe Ser Thr Leu Phe Pro Gly Leu Asn Pro
                140                 145                 150 cac ctc ctc acc ctc caa agc aac ttc aag ctc ccg ctc tat cgc gag       534
His Leu Leu Thr Leu Gln Ser Asn Phe Lys Leu Pro Leu Tyr Arg Glu
            155                 160                 165 ttg ctg ctc gcc ctc ggc atc tgc tcc gtc tcg atg aag agc tgc cag       582
Leu Leu Leu Ala Leu Gly Ile Cys Ser Val Ser Met Lys Ser Cys Gln
        170                 175                 180 aac atc ctg cgg caa ggt cct ggc tcg gct ctc acc atc gtt gtc ggt       630
Asn Ile Leu Arg Gln Gly Pro Gly Ser Ala Leu Thr Ile Val Val Gly
185                 190                 195 ggc gca gcc gag agc ttg agt gcg cat ccc gga acc gcc gac ctc acg       678
Gly Ala Ala Glu Ser Leu Ser Ala His Pro Gly Thr Ala Asp Leu Thr
200                 205                 210                 215 ctc aag cga cga aaa gga ttc atc aag ctc gcg atc cgg caa ggc gcc       726
Leu Lys Arg Arg Lys Gly Phe Ile Lys Leu Ala Ile Arg Gln Gly Ala
                220                 225                 230 gac ctc gtg ccc gtc ttt tcg ttc ggc gag aac gac atc ttc ggc cag       774
Asp Leu Val Pro Val Phe Ser Phe Gly Glu Asn Asp Ile Phe Gly Gln
            235                 240                 245 ctg cga aat gag cga ggg acg cgg ctg tac aag ttg cag aag cgt ttc       822
Leu Arg Asn Glu Arg Gly Thr Arg Leu Tyr Lys Leu Gln Lys Arg Phe
        250                 255                 260 cag ggc gta ttc ggc ttc act ctc cct ctc ttc tac ggt cgg gga ctc       870
Gln Gly Val Phe Gly Phe Thr Leu Pro Leu Phe Tyr Gly Arg Gly Leu
265                 270                 275 ttc aac tat aac gtt ggc ttg atg ccg tac cgc cat ccg atc gtc tcg       918
Phe Asn Tyr Asn Val Gly Leu Met Pro Tyr Arg His Pro Ile Val Ser
280                 285                 290                 295 gtc gtc ggt cga cca atc tcg gtg cag cag aag gac cac cca acg aca       966
Val Val Gly Arg Pro Ile Ser Val Gln Gln Lys Asp His Pro Thr Thr
                300                 305                 310 gcg gat ctc gaa gaa gtc cag gcg cgg tat atc gca gaa ctc aag cgc      1014
Ala Asp Leu Glu Glu Val Gln Ala Arg Tyr Ile Ala Glu Leu Lys Arg
            315                 320                 325 atc tgg gaa gac tac aag gac gcc tac gcc aaa agt cgc acg cgg gag      1062
Ile Trp Glu Asp Tyr Lys Asp Ala Tyr Ala Lys Ser Arg Thr Arg Glu
        330                 335                 340 ctc aat att atc gcc tga cctcctcgca acggacgctt cccgccggcc             1110
Leu Asn Ile Ile Ala
    345 aaaagaccct ccattgcctg tattctctcc tgtgtgtgcc atccctagcc gttgtcgatt    1170 cccccttgccg ttccctctc ctcgatatct cgatatccgt tctctgtagc ttgccttccg    1230 ctttgcacca tgcccccgtt caacacg                                        1257

<210> SEQ ID NO 6
<211> LENGTH: 348
<212> TYPE: PRT
<213> ORGANISM: Rhodosporidium toruloides
```

<400> SEQUENCE: 6

| | | | | | | | | | | | | | | | |
|---|---|---|---|---|---|---|---|---|---|---|---|---|---|---|---|
|Met|Gly|Gln|Gln|Ala|Thr|Leu|Glu|Glu|Leu|Tyr|Thr|Arg|Ser|Glu|Ile|
|1| | | |5| | | | |10| | | | |15| |
|Ser|Lys|Ile|Lys|Phe|Ala|Pro|Phe|Gly|Val|Pro|Arg|Ser|Arg|Arg|Leu|
| | | |20| | | | |25| | | | |30| | |
|Gln|Thr|Phe|Ser|Val|Phe|Ala|Trp|Thr|Thr|Ala|Leu|Pro|Ile|Leu|Leu|
| | |35| | | | |40| | | | |45| | | |
|Gly|Val|Phe|Phe|Leu|Leu|Cys|Ser|Phe|Pro|Pro|Leu|Trp|Pro|Ala|Val|
| |50| | | | |55| | | | |60| | | | |
|Ile|Ala|Tyr|Leu|Thr|Trp|Val|Phe|Phe|Ile|Asp|Gln|Ala|Pro|Thr|His|
|65| | | | |70| | | | |75| | | | |80|
|Gly|Gly|Arg|Ala|Gln|Ser|Trp|Leu|Arg|Lys|Ser|Arg|Ile|Trp|Val|Trp|
| | | | |85| | | | |90| | | | |95| |
|Phe|Ala|Gly|Tyr|Tyr|Pro|Val|Ser|Leu|Ile|Lys|Ser|Ala|Asp|Leu|Pro|
| | | |100| | | | |105| | | | |110| | |
|Pro|Asp|Arg|Lys|Tyr|Val|Phe|Gly|Tyr|His|Pro|His|Gly|Val|Ile|Gly|
| | |115| | | | |120| | | | |125| | | |
|Met|Gly|Ala|Ile|Ala|Asn|Phe|Ala|Thr|Asp|Ala|Thr|Gly|Phe|Ser|Thr|
|130| | | | |135| | | | |140| | | | | |
|Leu|Phe|Pro|Gly|Leu|Asn|Pro|His|Leu|Leu|Thr|Leu|Gln|Ser|Asn|Phe|
|145| | | | |150| | | | |155| | | | |160|
|Lys|Leu|Pro|Leu|Tyr|Arg|Glu|Leu|Leu|Ala|Leu|Gly|Ile|Cys|Ser|
| | | | |165| | | | |170| | | | |175| |
|Val|Ser|Met|Lys|Ser|Cys|Gln|Asn|Ile|Leu|Arg|Gln|Gly|Pro|Gly|Ser|
| | |180| | | | |185| | | | |190| | | |
|Ala|Leu|Thr|Ile|Val|Val|Gly|Gly|Ala|Ala|Glu|Ser|Leu|Ser|Ala|His|
| | |195| | | | |200| | | | |205| | | |
|Pro|Gly|Thr|Ala|Asp|Leu|Thr|Leu|Lys|Arg|Arg|Lys|Gly|Phe|Ile|Lys|
| |210| | | | |215| | | | |220| | | | |
|Leu|Ala|Ile|Arg|Gln|Gly|Ala|Asp|Leu|Val|Pro|Val|Phe|Ser|Phe|Gly|
|225| | | | |230| | | | |235| | | | |240|
|Glu|Asn|Asp|Ile|Phe|Gly|Gln|Leu|Arg|Asn|Glu|Arg|Gly|Thr|Arg|Leu|
| | | | |245| | | | |250| | | | |255| |
|Tyr|Lys|Leu|Gln|Lys|Arg|Phe|Gln|Gly|Val|Phe|Gly|Phe|Thr|Leu|Pro|
| | | |260| | | | |265| | | | |270| | |
|Leu|Phe|Tyr|Gly|Arg|Gly|Leu|Phe|Asn|Tyr|Asn|Val|Gly|Leu|Met|Pro|
| | |275| | | | |280| | | | |285| | | |
|Tyr|Arg|His|Pro|Ile|Val|Ser|Val|Val|Gly|Arg|Pro|Ile|Ser|Val|Gln|
| |290| | | | |295| | | | |300| | | | |
|Gln|Lys|Asp|His|Pro|Thr|Thr|Ala|Asp|Leu|Glu|Glu|Val|Gln|Ala|Arg|
|305| | | | |310| | | | |315| | | | |320|
|Tyr|Ile|Ala|Glu|Leu|Lys|Arg|Ile|Trp|Glu|Asp|Tyr|Lys|Asp|Ala|Tyr|
| | | | |325| | | | |330| | | | |335| |
|Ala|Lys|Ser|Arg|Thr|Arg|Glu|Leu|Asn|Ile|Ile|Ala| | | | |
| | | |340| | | | |345| | | | | | | |

<210> SEQ ID NO 7
<211> LENGTH: 2336
<212> TYPE: DNA
<213> ORGANISM: Rhodosporidium toruloides
<220> FEATURE:
<221> NAME/KEY: CDS
<222> LOCATION: (54)..(2264)

<400> SEQUENCE: 7

-continued

| | | |
|---|---|---|
| ctcactagac ctcgctcacc tcgcttgact ggactgctgc tggctgagaa agg atg<br>                                                                                            Met<br>                                                                                           1 | | 56 |
| agc aca gta cgg agg cgc aac cag ccg aag cgc aac gct tct gcg ccc<br>Ser Thr Val Arg Arg Arg Asn Gln Pro Lys Arg Asn Ala Ser Ala Pro<br>            5                            10                            15 | | 104 |
| gcc aat cag ctc gat acc gac gat tct tcg ccc gct ccc tct cga ccc<br>Ala Asn Gln Leu Asp Thr Asp Asp Ser Ser Pro Ala Pro Ser Arg Pro<br>      20                         25                            30 | | 152 |
| gac tcg ccc gat atc gac aaa gcg ccg gtg cga gag gtc cca ctg ttc<br>Asp Ser Pro Asp Ile Asp Lys Ala Pro Val Arg Glu Val Pro Leu Phe<br>        35                            40                          45 | | 200 |
| aag cgg agg ctg aaa aag gga gat ggc aag gtg gaa gac ccg aag gtc<br>Lys Arg Arg Leu Lys Lys Gly Asp Gly Lys Val Glu Asp Pro Lys Val<br>50                       55                            60                           65 | | 248 |
| att ctg gac gag aag acg ggc agg gtc tcc ctc gac ttt cct agg acg<br>Ile Leu Asp Glu Lys Thr Gly Arg Val Ser Leu Asp Phe Pro Arg Thr<br>                  70                            75                         80 | | 296 |
| cca tat gac cag ctc gac ctg agt gac tcg ttc ctc gcc gcc ttg cac<br>Pro Tyr Asp Gln Leu Asp Leu Ser Asp Ser Phe Leu Ala Ala Leu His<br>                      85                            90                         95 | | 344 |
| gag gca ccc ttc gag cca aag aag acg tgg acg aag cgg cgg aga ggc<br>Glu Ala Pro Phe Glu Pro Lys Lys Thr Trp Thr Lys Arg Arg Arg Gly<br>                100                            105                         110 | | 392 |
| tgg ttc ttt ttg gga gga ttg ctc ggt ctc tgc gca ggc tgg atg ttc<br>Trp Phe Phe Leu Gly Gly Leu Leu Gly Leu Cys Ala Gly Trp Met Phe<br>           115                            120                         125 | | 440 |
| acc gaa ggc gac cca ctc gcc tct ctc gcc aac ctc gac ctc gac gcc<br>Thr Glu Gly Asp Pro Leu Ala Ser Leu Ala Asn Leu Asp Leu Asp Ala<br>130                       135                        140                          145 | | 488 |
| ttc tca tcc tgg gac ctt cag tca atc ctc gcc gac atg cct tcc ctc<br>Phe Ser Ser Trp Asp Leu Gln Ser Ile Leu Ala Asp Met Pro Ser Leu<br>                150                            155                         160 | | 536 |
| tcc gct ctc aac gtc acc gaa ctc ctt gca cca ggt cgt gaa tgg ctg<br>Ser Ala Leu Asn Val Thr Glu Leu Leu Ala Pro Gly Arg Glu Trp Leu<br>                  165                            170                         175 | | 584 |
| aac agc cga gtg aac aac ttt gac gtc ggg cga gat gcg gct gcg cga<br>Asn Ser Arg Val Asn Asn Phe Asp Val Gly Arg Asp Ala Ala Ala Arg<br>              180                            185                         190 | | 632 |
| ggg ctg aag aag aag cat gcg gtc att ctg gtg ccg ggc atc atc tcg<br>Gly Leu Lys Lys Lys His Ala Val Ile Leu Val Pro Gly Ile Ile Ser<br>         195                            200                         205 | | 680 |
| tcg ggt ctc gag tcg tgg tcg acc aag cca gat gca gct ccc ttc ttt<br>Ser Gly Leu Glu Ser Trp Ser Thr Lys Pro Asp Ala Ala Pro Phe Phe<br>210                       215                        220                          225 | | 728 |
| cgc tcg aag gtc tgg gcg gga acc tcg atg att cgt gcc gtc atc aag<br>Arg Ser Lys Val Trp Ala Gly Thr Ser Met Ile Arg Ala Val Ile Lys<br>                  230                            235                         240 | | 776 |
| aac aag gag gct tgg gtc aag gcg atc agt ctc gac ccg ttt act gga<br>Asn Lys Glu Ala Trp Val Lys Ala Ile Ser Leu Asp Pro Phe Thr Gly<br>                245                            250                         255 | | 824 |
| ttg gat cag gac ggg tac aag atc cga gct gct cag ggt ctc gac gcc<br>Leu Asp Gln Asp Gly Tyr Lys Ile Arg Ala Ala Gln Gly Leu Asp Ala<br>              260                            265                         270 | | 872 |
| gct tcc gct ttc atg ccc ggg tac tgg atc tgg cag aag gtc atc gag<br>Ala Ser Ala Phe Met Pro Gly Tyr Trp Ile Trp Gln Lys Val Ile Glu<br>         275                            280                         285 | | 920 |
| aac ctc gcc gtc ctg gac tac gac cac aac gac ctg tct ctc gca tca<br>Asn Leu Ala Val Leu Asp Tyr Asp His Asn Asp Leu Ser Leu Ala Ser | | 968 |

-continued

| | | | | |
|---|---|---|---|---|
| 290 | 295 | 300 | 305 | |
| tac gac tgg cga ctt gcc ttc tac aac ctc gaa gtc cga gat cgt tac<br>Tyr Asp Trp Arg Leu Ala Phe Tyr Asn Leu Glu Val Arg Asp Arg Tyr<br>          310                   315                320 | | | | 1016 |
| ttc tct cgg ctc aag gct tcg ata gaa ttc aac ctc gcc atc agc ggc<br>Phe Ser Arg Leu Lys Ala Ser Ile Glu Phe Asn Leu Ala Ile Ser Gly<br>    325                   330                 335 | | | | 1064 |
| cag aag acg gtt ctc gtc tcg cac agc atg ggc tct tcg gct ctt ctg<br>Gln Lys Thr Val Leu Val Ser His Ser Met Gly Ser Ser Ala Leu Leu<br>        340                 345                350 | | | | 1112 |
| tgg ttc ttc aag tgg gtc gag tcg ccg aga tac ggc aac ggc ggt ccg<br>Trp Phe Phe Lys Trp Val Glu Ser Pro Arg Tyr Gly Asn Gly Gly Pro<br>355                     360                365 | | | | 1160 |
| gac tgg gtc gag cgg cac gtc tcg gac tgg gtc aat gtc gcg ggc acg<br>Asp Trp Val Glu Arg His Val Ser Asp Trp Val Asn Val Ala Gly Thr<br>370                     375                380                385 | | | | 1208 |
| atg ctc ggc gtt ccg aaa gcc atg gcc gcc ctc ctc tcg ggc gag atg<br>Met Leu Gly Val Pro Lys Ala Met Ala Ala Leu Leu Ser Gly Glu Met<br>            390                 395                400 | | | | 1256 |
| cgc gat acg gtc acg ctt tct ccc gcc gtc atc tac ctc ctc gaa cgc<br>Arg Asp Thr Val Thr Leu Ser Pro Ala Val Ile Tyr Leu Leu Glu Arg<br>              405                410                415 | | | | 1304 |
| ttc ttc tcc cgc tcc gaa cgc gcc aag ctg ttc cgc tcg tgg gca ggt<br>Phe Phe Ser Arg Ser Glu Arg Ala Lys Leu Phe Arg Ser Trp Ala Gly<br>        420                   425                 430 | | | | 1352 |
| gcg gcg agc atg atg ctt aag gga gga aac gac gtc tgg ggc gac gag<br>Ala Ala Ser Met Met Leu Lys Gly Gly Asn Asp Val Trp Gly Asp Glu<br>        435                   440                 445 | | | | 1400 |
| cag cag gcg ccg gac gac atg gag gaa tcg gca atc acg ggc gga aag<br>Gln Gln Ala Pro Asp Asp Met Glu Glu Ser Ala Ile Thr Gly Gly Lys<br>450                     455                460                465 | | | | 1448 |
| ctg tac tac ttc cgg cct gag agt cac tcg aac acg tcg gaa gtg acg<br>Leu Tyr Tyr Phe Arg Pro Glu Ser His Ser Asn Thr Ser Glu Val Thr<br>              470                475                480 | | | | 1496 |
| gaa gac acc gtc cac ccg aac ctg acg ctc aac gac gcg acc agc ttc<br>Glu Asp Thr Val His Pro Asn Leu Thr Leu Asn Asp Ala Thr Ser Phe<br>            485                 490                495 | | | | 1544 |
| ctc cta gag aag gtc ccg ccg tcc tac cag cag atg ctg gcg agt aac<br>Leu Leu Glu Lys Val Pro Pro Ser Tyr Gln Gln Met Leu Ala Ser Asn<br>        500                 505                510 | | | | 1592 |
| ttc tcg ttc ggc ttc gag cgc gac gag cag cag ctc atc aag aac aac<br>Phe Ser Phe Gly Phe Glu Arg Asp Glu Gln Gln Leu Ile Lys Asn Asn<br>        515                 520                525 | | | | 1640 |
| gac gac cat tcg aag tgg agc aat ccg ctc gag gtg cag ctg ccg aag<br>Asp Asp His Ser Lys Trp Ser Asn Pro Leu Glu Val Gln Leu Pro Lys<br>530                   535                540                545 | | | | 1688 |
| gcg ccg tcg atg acc atc tac tgc ttg tac ggc gtc ggc aag gag act<br>Ala Pro Ser Met Thr Ile Tyr Cys Leu Tyr Gly Val Gly Lys Glu Thr<br>            550                 555                560 | | | | 1736 |
| gag cgc gcg tac ttc tac cag cag ggc ggt tac gag cac gac gaa acg<br>Glu Arg Ala Tyr Phe Tyr Gln Gln Gly Gly Tyr Glu His Asp Glu Thr<br>              565                570                575 | | | | 1784 |
| ccg acc gtc aat ctc aca gac tcg cgg gcg tcc agc ctc gaa ccc gtt<br>Pro Thr Val Asn Leu Thr Asp Ser Arg Ala Ser Ser Leu Glu Pro Val<br>            580                 585                590 | | | | 1832 |
| tgt ctc gag ccg aac tgc acc gac tcg acg ccg cgc ccg ctc gac<br>Cys Leu Glu Pro Asn Cys Thr Asp Ser Thr Pro Arg Pro Leu Asp<br>        595                   600                605 | | | | 1880 |
| ctg ccg ctc cag cga cgc gta tgg atc gac ggt agc gtg acg atg gac | | | | 1928 |

```
Leu Pro Leu Gln Arg Arg Val Trp Ile Asp Gly Ser Val Thr Met Asp
610                 615                 620                 625 gag aag agc gtg ccg aag gtt agg agc gga gtc gtc ttc aac gac gga      1976
Glu Lys Ser Val Pro Lys Val Arg Ser Gly Val Val Phe Asn Asp Gly
                630                 635                 640 gac ggg acg gtc agc ttg ctc agt ctg ggc agc atg tgt gtc gag ggc      2024
Asp Gly Thr Val Ser Leu Leu Ser Leu Gly Ser Met Cys Val Glu Gly
            645                 650                 655 tgg aag cga cct ctg tac aat ccg gca ggc atc aag gtc gtc acg cac      2072
Trp Lys Arg Pro Leu Tyr Asn Pro Ala Gly Ile Lys Val Val Thr His
        660                 665                 670 gag atc ttg cat gct ccg ctc gct ttc gat ccg cga ggt gga cca acg      2120
Glu Ile Leu His Ala Pro Leu Ala Phe Asp Pro Arg Gly Gly Pro Thr
    675                 680                 685 act gca gac cat gtc gac atc ctc gga tca tcc gaa ctg aac gac gcg      2168
Thr Ala Asp His Val Asp Ile Leu Gly Ser Ser Glu Leu Asn Asp Ala
690                 695                 700                 705 atc ctc gac att gct gcc ggc caa ggc gag cgc gtc aag gac caa tac      2216
Ile Leu Asp Ile Ala Ala Gly Gln Gly Glu Arg Val Lys Asp Gln Tyr
                710                 715                 720 cat tcg cgg atc cag gac att gcg cgc aag atc agg tgg gag ggc tga      2264
His Ser Arg Ile Gln Asp Ile Ala Arg Lys Ile Arg Trp Glu Gly
            725                 730                 735 cccaccctgt acgccttgcc cagcgtttct ccccttctc gtgtagagat cgcaacagtg     2324
ttgtttcccg ct                                                         2336

<210> SEQ ID NO 8
<211> LENGTH: 736
<212> TYPE: PRT
<213> ORGANISM: Rhodosporidium toruloides

<400> SEQUENCE: 8

Met Ser Thr Val Arg Arg Asn Gln Pro Lys Arg Asn Ala Ser Ala
1               5                   10                  15

Pro Ala Asn Gln Leu Asp Thr Asp Ser Ser Pro Ala Pro Ser Arg
                20                  25                  30

Pro Asp Ser Pro Asp Ile Asp Lys Ala Pro Val Arg Glu Val Pro Leu
            35                  40                  45

Phe Lys Arg Arg Leu Lys Lys Gly Asp Gly Lys Val Glu Asp Pro Lys
50                  55                  60

Val Ile Leu Asp Glu Lys Thr Gly Arg Val Ser Leu Asp Phe Pro Arg
65                  70                  75                  80

Thr Pro Tyr Asp Gln Leu Asp Leu Ser Asp Ser Phe Leu Ala Ala Leu
                85                  90                  95

His Glu Ala Pro Phe Glu Pro Lys Lys Thr Trp Thr Lys Arg Arg
                100                 105                 110

Gly Trp Phe Phe Leu Gly Gly Leu Gly Leu Cys Ala Gly Trp Met
            115                 120                 125

Phe Thr Glu Gly Asp Pro Leu Ala Ser Leu Ala Asn Leu Asp Leu Asp
                130                 135                 140

Ala Phe Ser Ser Trp Asp Leu Gln Ser Ile Leu Ala Asp Met Pro Ser
145                 150                 155                 160

Leu Ser Ala Leu Asn Val Thr Glu Leu Leu Ala Pro Gly Arg Glu Trp
                165                 170                 175

Leu Asn Ser Arg Val Asn Asn Phe Asp Val Gly Arg Asp Ala Ala Ala
                180                 185                 190
```

```
Arg Gly Leu Lys Lys Lys His Ala Val Ile Leu Val Pro Gly Ile Ile
            195                 200                 205

Ser Ser Gly Leu Glu Ser Trp Ser Thr Lys Pro Asp Ala Ala Pro Phe
    210                 215                 220

Phe Arg Ser Lys Val Trp Ala Gly Thr Ser Met Ile Arg Ala Val Ile
225                 230                 235                 240

Lys Asn Lys Glu Ala Trp Val Lys Ala Ile Ser Leu Asp Pro Phe Thr
                245                 250                 255

Gly Leu Asp Gln Asp Gly Tyr Lys Ile Arg Ala Ala Gln Gly Leu Asp
            260                 265                 270

Ala Ala Ser Ala Phe Met Pro Gly Tyr Trp Ile Trp Gln Lys Val Ile
        275                 280                 285

Glu Asn Leu Ala Val Leu Asp Tyr Asp His Asn Asp Leu Ser Leu Ala
    290                 295                 300

Ser Tyr Asp Trp Arg Leu Ala Phe Tyr Asn Leu Glu Val Arg Asp Arg
305                 310                 315                 320

Tyr Phe Ser Arg Leu Lys Ala Ser Ile Glu Phe Asn Leu Ala Ile Ser
                325                 330                 335

Gly Gln Lys Thr Val Leu Val Ser His Ser Met Gly Ser Ser Ala Leu
            340                 345                 350

Leu Trp Phe Phe Lys Trp Val Glu Ser Pro Arg Tyr Gly Asn Gly Gly
        355                 360                 365

Pro Asp Trp Val Glu Arg His Val Ser Asp Trp Val Asn Val Ala Gly
    370                 375                 380

Thr Met Leu Gly Val Pro Lys Ala Met Ala Leu Leu Ser Gly Glu
385                 390                 395                 400

Met Arg Asp Thr Val Thr Leu Ser Pro Ala Val Ile Tyr Leu Leu Glu
                405                 410                 415

Arg Phe Phe Ser Arg Ser Glu Arg Ala Lys Leu Phe Arg Ser Trp Ala
            420                 425                 430

Gly Ala Ala Ser Met Met Leu Lys Gly Gly Asn Asp Val Trp Gly Asp
        435                 440                 445

Glu Gln Gln Ala Pro Asp Asp Met Glu Glu Ser Ala Ile Thr Gly Gly
    450                 455                 460

Lys Leu Tyr Tyr Phe Arg Pro Glu Ser His Ser Asn Thr Ser Glu Val
465                 470                 475                 480

Thr Glu Asp Thr Val His Pro Asn Leu Thr Leu Asn Asp Ala Thr Ser
                485                 490                 495

Phe Leu Leu Glu Lys Val Pro Pro Ser Tyr Gln Gln Met Leu Ala Ser
            500                 505                 510

Asn Phe Ser Phe Gly Phe Glu Arg Asp Glu Gln Gln Leu Ile Lys Asn
        515                 520                 525

Asn Asp Asp His Ser Lys Trp Ser Asn Pro Leu Glu Val Gln Leu Pro
    530                 535                 540

Lys Ala Pro Ser Met Thr Ile Tyr Cys Leu Tyr Gly Val Gly Lys Glu
545                 550                 555                 560

Thr Glu Arg Ala Tyr Phe Tyr Gln Gln Gly Gly Tyr Glu His Asp Glu
                565                 570                 575

Thr Pro Thr Val Asn Leu Thr Asp Ser Arg Ala Ser Ser Leu Glu Pro
            580                 585                 590

Val Cys Leu Glu Pro Asn Cys Thr Asp Ser Thr Pro Arg Pro Pro Leu
        595                 600                 605

Asp Leu Pro Leu Gln Arg Arg Val Trp Ile Asp Gly Ser Val Thr Met
```

```
                   610              615              620
Asp Glu Lys Ser Val Pro Lys Val Arg Ser Gly Val Val Phe Asn Asp
625                 630              635                 640

Gly Asp Gly Thr Val Ser Leu Leu Ser Leu Gly Ser Met Cys Val Glu
                645              650                 655

Gly Trp Lys Arg Pro Leu Tyr Asn Pro Ala Gly Ile Lys Val Val Thr
            660                 665              670

His Glu Ile Leu His Ala Pro Leu Ala Phe Asp Pro Arg Gly Gly Pro
            675              680              685

Thr Thr Ala Asp His Val Asp Ile Leu Gly Ser Ser Glu Leu Asn Asp
690                 695              700

Ala Ile Leu Asp Ile Ala Ala Gly Gln Gly Glu Arg Val Lys Asp Gln
705                 710              715                 720

Tyr His Ser Arg Ile Gln Asp Ile Ala Arg Lys Ile Arg Trp Glu Gly
                725              730              735

<210> SEQ ID NO 9
<211> LENGTH: 2153
<212> TYPE: DNA
<213> ORGANISM: Rhodosporidium toruloides
<220> FEATURE:
<221> NAME/KEY: CDS
<222> LOCATION: (7)..(2043)

<400> SEQUENCE: 9 caaaga atg gcc tcg cta gac ccg cca ctc cca ggc cca gcc aac ctc        48
       Met Ala Ser Leu Asp Pro Pro Leu Pro Gly Pro Ala Asn Leu
         1               5                  10 gtc gac gac gcc ctc cga cac ccc gac tcg gca cct ccc atc ccg ccc       96
Val Asp Asp Ala Leu Arg His Pro Asp Ser Ala Pro Pro Ile Pro Pro
 15              20                  25                  30 gac tcc gct cct cct tcg cat ccc tcg act gcg act cag ccc tcc gca     144
Asp Ser Ala Pro Pro Ser His Pro Ser Thr Ala Thr Gln Pro Ser Ala
                 35                  40                  45 act tcg cgc gga cag ctt tcg act gct tcg agc tat gcg agc gat gtg     192
Thr Ser Arg Gly Gln Leu Ser Thr Ala Ser Ser Tyr Ala Ser Asp Val
             50                  55                  60 tcg acg agg gac ggg aca ccg gat ctg gcg aat gga caa ggc gta acg     240
Ser Thr Arg Asp Gly Thr Pro Asp Leu Ala Asn Gly Gln Gly Val Thr
         65                  70                  75 acg act att acg acc gtg aca ggc aag ggc gga aag gcg gtc acc cag     288
Thr Thr Ile Thr Thr Val Thr Gly Lys Gly Gly Lys Ala Val Thr Gln
     80                  85                  90 acc ctc acc cac gtc ggc gcc tcc tcc gtc gac gcc cgc ttc tcc tcc     336
Thr Leu Thr His Val Gly Ala Ser Ser Val Asp Ala Arg Phe Ser Ser
95                  100                 105                 110 tcc acc tcc tcc atc acc ctc cgc ccc atc cca gca cgc ggc ggc gac     384
Ser Thr Ser Ser Ile Thr Leu Arg Pro Ile Pro Ala Arg Gly Gly Asp
                115                 120                 125 ccg aag aag atc aaa gtc ctc cgt tcc cgt cga acc cac ttc gcc cca     432
Pro Lys Lys Ile Lys Val Leu Arg Ser Arg Arg Thr His Phe Ala Pro
            130                 135                 140 cgc acc tcc cac ttc gac cgc cac aac ctg acc tcc gcc tcc gac ccc     480
Arg Thr Ser His Phe Asp Arg His Asn Leu Thr Ser Ala Ser Asp Pro
        145                 150                 155 ttc cgc ggc ctc tac act tta ttc tgg atc gta atc ttc gtc gga gca     528
Phe Arg Gly Leu Tyr Thr Leu Phe Trp Ile Val Ile Phe Val Gly Ala
    160                 165                 170 ctc aag act gtg tat cat cgg ttt gcg gag cag ggt ggg tgg gga ggt     576
```

| | | | | | | | | | | | | | | | |
|---|---|---|---|---|---|---|---|---|---|---|---|---|---|---|---|
|Leu|Lys|Thr|Val|Tyr|His|Arg|Phe|Ala|Glu|Gln|Gly|Gly|Trp|Gly|Gly|
|175| | | |180| | | |185| | | |190| | | |

| gaa | tgg | agg | ttt | gcg | gcg | ttg | att | agt | cgt | gat | ggg | tgg | gtg | ttg | gcg | 624 |
|---|---|---|---|---|---|---|---|---|---|---|---|---|---|---|---|---|
| Glu | Trp | Arg | Phe | Ala | Ala | Leu | Ile | Ser | Arg | Asp | Gly | Trp | Val | Leu | Ala | |
| | | | | 195 | | | | | 200 | | | | | 205 | | |

| gtt | agt | gat | gcg | gtg | ttg | gtt | agc | gcg | tcg | ttg | ttg | tgc | gtg | cca | tat | 672 |
|---|---|---|---|---|---|---|---|---|---|---|---|---|---|---|---|---|
| Val | Ser | Asp | Ala | Val | Leu | Val | Ser | Ala | Ser | Leu | Leu | Cys | Val | Pro | Tyr | |
| | | | 210 | | | | | 215 | | | | | 220 | | | |

| gcc | aag | ctg | ctc | gta | cac | ggc | tgg | atc | cgg | tac | cac | ggc | gcc | ggc | gta | 720 |
|---|---|---|---|---|---|---|---|---|---|---|---|---|---|---|---|---|
| Ala | Lys | Leu | Leu | Val | His | Gly | Trp | Ile | Arg | Tyr | His | Gly | Ala | Gly | Val | |
| | | | 225 | | | | | 230 | | | | | 235 | | | |

| atc | atc | caa | cac | atc | tgc | caa | acg | ctc | tac | ctc | gcc | atc | gcg | atc | cgc | 768 |
|---|---|---|---|---|---|---|---|---|---|---|---|---|---|---|---|---|
| Ile | Ile | Gln | His | Ile | Cys | Gln | Thr | Leu | Tyr | Leu | Ala | Ile | Ala | Ile | Arg | |
| | | | 240 | | | | | 245 | | | | | 250 | | | |

| tgg | acc | ttc | cac | cgc | aac | tgg | ccc | tgg | gtc | caa | agc | ggc | ttc | atg | acc | 816 |
|---|---|---|---|---|---|---|---|---|---|---|---|---|---|---|---|---|
| Trp | Thr | Phe | His | Arg | Asn | Trp | Pro | Trp | Val | Gln | Ser | Gly | Phe | Met | Thr | |
| 255 | | | | | 260 | | | | | 265 | | | | | 270 | |

| ctc | cac | gcc | ctc | tcg | atg | ctc | atg | aag | atc | cat | agc | tac | tgt | tcg | cta | 864 |
|---|---|---|---|---|---|---|---|---|---|---|---|---|---|---|---|---|
| Leu | His | Ala | Leu | Ser | Met | Leu | Met | Lys | Ile | His | Ser | Tyr | Cys | Ser | Leu | |
| | | | | 275 | | | | | 280 | | | | | 285 | | |

| aac | ggg | gag | ctt | tcg | gag | cgg | cgg | aga | cag | ttg | agg | aag | gat | gag | ggg | 912 |
|---|---|---|---|---|---|---|---|---|---|---|---|---|---|---|---|---|
| Asn | Gly | Glu | Leu | Ser | Glu | Arg | Arg | Arg | Gln | Leu | Arg | Lys | Asp | Glu | Gly | |
| | | | | 290 | | | | | 295 | | | | | 300 | | |

| agg | ctg | gag | gag | gtg | ctg | gag | gag | atg | ggc | ggg | agg | agg | gcg | gag | | 960 |
|---|---|---|---|---|---|---|---|---|---|---|---|---|---|---|---|---|
| Arg | Leu | Glu | Glu | Val | Leu | Glu | Glu | Met | Gly | Gly | Arg | Arg | Ala | Glu | | |
| | | | | 305 | | | | | 310 | | | | | 315 | | |

| agg | gag | gcg | agg | gag | gag | tgg | gag | agg | cag | tgc | ggt | gag | gcg | gcg | agg | 1008 |
|---|---|---|---|---|---|---|---|---|---|---|---|---|---|---|---|---|
| Arg | Glu | Ala | Arg | Glu | Glu | Trp | Glu | Arg | Gln | Cys | Gly | Glu | Ala | Ala | Arg | |
| | 320 | | | | | 325 | | | | | 330 | | | | | |

| gcg | aag | gag | ggc | gag | gcg | ggt | tcg | cgc | gag | gga | aag | aag | gag | gag | gtg | 1056 |
|---|---|---|---|---|---|---|---|---|---|---|---|---|---|---|---|---|
| Ala | Lys | Glu | Gly | Glu | Ala | Gly | Ser | Arg | Glu | Gly | Lys | Lys | Glu | Glu | Val | |
| 335 | | | | | 340 | | | | | 345 | | | | | 350 | |

| gcg | gcc | cag | tcg | tcg | aca | gac | gct | tcg | act | tcg | gct | ctg | tcg | tcg | gag | 1104 |
|---|---|---|---|---|---|---|---|---|---|---|---|---|---|---|---|---|
| Ala | Ala | Gln | Ser | Ser | Thr | Asp | Ala | Ser | Thr | Ser | Ala | Leu | Ser | Ser | Glu | |
| | | | | 355 | | | | | 360 | | | | | 365 | | |

| gat | gag | gcg | gca | gcg | gcg | ttg | ctg | cgg | cat | cga | cag | tcg | act | gcc | cga | 1152 |
|---|---|---|---|---|---|---|---|---|---|---|---|---|---|---|---|---|
| Asp | Glu | Ala | Ala | Ala | Ala | Leu | Leu | Arg | His | Arg | Gln | Ser | Thr | Ala | Arg | |
| | | | 370 | | | | | 375 | | | | | 380 | | | |

| cgg | cgt | tcc | atc | tcg | cca | tcc | gcc | tct | cgc | acc | cac | tct | tct | tcc | gct | 1200 |
|---|---|---|---|---|---|---|---|---|---|---|---|---|---|---|---|---|
| Arg | Arg | Ser | Ile | Ser | Pro | Ser | Ala | Ser | Arg | Thr | His | Ser | Ser | Ser | Ala | |
| | | | | 385 | | | | | 390 | | | | | 395 | | |

| tcc | tcc | tct | cac | ccc | gct | ccc | tcc | cgc | gcc | gaa | gag | ccc | caa | gaa | ggc | 1248 |
|---|---|---|---|---|---|---|---|---|---|---|---|---|---|---|---|---|
| Ser | Ser | Ser | His | Pro | Ala | Pro | Ser | Arg | Ala | Glu | Glu | Pro | Gln | Glu | Gly | |
| | 400 | | | | | 405 | | | | | 410 | | | | | |

| gtc | gag | acg | ctc | aca | tgg | cac | cca | tcc | gac | cga | gtc | agc | aaa | ctt | gct | 1296 |
|---|---|---|---|---|---|---|---|---|---|---|---|---|---|---|---|---|
| Val | Glu | Thr | Leu | Thr | Trp | His | Pro | Ser | Asp | Arg | Val | Ser | Lys | Leu | Ala | |
| 415 | | | | | 420 | | | | | 425 | | | | | 430 | |

| atc | gcc | atc | tgc | gag | gcg | aag | gac | ctt | ctc | acc | agc | aac | ggc | aag | aaa | 1344 |
|---|---|---|---|---|---|---|---|---|---|---|---|---|---|---|---|---|
| Ile | Ala | Ile | Cys | Glu | Ala | Lys | Asp | Leu | Leu | Thr | Ser | Asn | Gly | Lys | Lys | |
| | | | | 435 | | | | | 440 | | | | | 445 | | |

| ccc | gtc | acg | ttc | ccc | gag | aac | gtc | acg | ttt | gcg | aac | ttc | atc | gac | tac | 1392 |
|---|---|---|---|---|---|---|---|---|---|---|---|---|---|---|---|---|
| Pro | Val | Thr | Phe | Pro | Glu | Asn | Val | Thr | Phe | Ala | Asn | Phe | Ile | Asp | Tyr | |
| | | | 450 | | | | | 455 | | | | | 460 | | | |

| ttg | ctt | gtg | ccg | acg | ctg | gtg | tat | gag | ctg | gaa | tac | cct | cgg | acg | gac | 1440 |
|---|---|---|---|---|---|---|---|---|---|---|---|---|---|---|---|---|
| Leu | Leu | Val | Pro | Thr | Leu | Val | Tyr | Glu | Leu | Glu | Tyr | Pro | Arg | Thr | Asp | |
| | | | | 465 | | | | | 470 | | | | | 475 | | |

| tcc | atc | cgc | cct | ctc | tac | atc | ctc | gaa | aag | acc | ctc | gca | acc | ttc | ggc | 1488 |
|---|---|---|---|---|---|---|---|---|---|---|---|---|---|---|---|---|
| Ser | Ile | Arg | Pro | Leu | Tyr | Ile | Leu | Glu | Lys | Thr | Leu | Ala | Thr | Phe | Gly | |
| | 480 | | | | | 485 | | | | | 490 | | | | | |

```
acc ttc tcc atc ctc gtc ctg atc gtc gac tcg ttc atc ctc ccc gtc    1536
Thr Phe Ser Ile Leu Val Leu Ile Val Asp Ser Phe Ile Leu Pro Val
495                 500                 505                 510 acc tcg cgc acc gac acc ccc ctc ttc ggt ttc gtc ctc gac ctc gcg    1584
Thr Ser Arg Thr Asp Thr Pro Leu Phe Gly Phe Val Leu Asp Leu Ala
            515                 520                 525 ctc ccg ttc aca ctc gcg tac ctc ctc atc ttt tat gtc att ttc gag    1632
Leu Pro Phe Thr Leu Ala Tyr Leu Leu Ile Phe Tyr Val Ile Phe Glu
        530                 535                 540 ggc gtg tgt aat ggg ttt gcc gag ttg acg agg ttt gcg gat cgg aac    1680
Gly Val Cys Asn Gly Phe Ala Glu Leu Thr Arg Phe Ala Asp Arg Asn
    545                 550                 555 ttc ttc gac gac tgg tgg aac tcg tgc acg ttc gat gag ttc tcc cgc    1728
Phe Phe Asp Asp Trp Trp Asn Ser Cys Thr Phe Asp Glu Phe Ser Arg
560                 565                 570 aaa tgg aac cgc cca gtg cac gcc ttc ctc ctc cgc cac gtc tac gcc    1776
Lys Trp Asn Arg Pro Val His Ala Phe Leu Leu Arg His Val Tyr Ala
575                 580                 585                 590 gaa acg atg gcc tcg tac aag ctc tcg aag ctc tcg gcc gcg ttc gtc    1824
Glu Thr Met Ala Ser Tyr Lys Leu Ser Lys Leu Ser Ala Ala Phe Val
            595                 600                 605 acg ttc ttg ttc agc gct tgc gtg cac gaa ctc gtc atg gcg gtc gtc    1872
Thr Phe Leu Phe Ser Ala Cys Val His Glu Leu Val Met Ala Val Val
        610                 615                 620 acg aag aag ctt cgg ctg tat ttg ttc tcg atg cag atg gcc caa ctc    1920
Thr Lys Lys Leu Arg Leu Tyr Leu Phe Ser Met Gln Met Ala Gln Leu
    625                 630                 635 ccg ctc atc atg gtc ggc cgc gcc aag atc ttc cgc aag tac cct gcc    1968
Pro Leu Ile Met Val Gly Arg Ala Lys Ile Phe Arg Lys Tyr Pro Ala
640                 645                 650 ctc ggc aac ctc ttc ttc tgg ctc gct ctt ctc tcg ggg ttc ccg ctt    2016
Leu Gly Asn Leu Phe Phe Trp Leu Ala Leu Leu Ser Gly Phe Pro Leu
655                 660                 665                 670 ctc ggg acg ctg tat ttg cgg tac tga gctcagggcg cagtgcacga          2063
Leu Gly Thr Leu Tyr Leu Arg Tyr
            675 ctgtattcac taggcagtgc cttgcaatct gcatttccgc cttcgctcgt tgcaagcggg  2123 tcgactttca gcgcgaagtc tgcgacggcc                                   2153

<210> SEQ ID NO 10
<211> LENGTH: 678
<212> TYPE: PRT
<213> ORGANISM: Rhodosporidium toruloides

<400> SEQUENCE: 10

Met Ala Ser Leu Asp Pro Pro Leu Pro Gly Pro Ala Asn Leu Val Asp
1               5                   10                  15

Asp Ala Leu Arg His Pro Asp Ser Ala Pro Ile Pro Pro Asp Ser
            20                  25                  30

Ala Pro Pro Ser His Pro Ser Thr Ala Thr Gln Pro Ala Thr Ser
        35                  40                  45

Arg Gly Gln Leu Ser Thr Ala Ser Ser Tyr Ala Ser Asp Val Ser Thr
    50                  55                  60

Arg Asp Gly Thr Pro Asp Leu Ala Asn Gly Gln Gly Val Thr Thr Thr
65                  70                  75                  80

Ile Thr Thr Val Thr Gly Lys Gly Gly Lys Ala Val Thr Gln Thr Leu
                85                  90                  95

Thr His Val Gly Ala Ser Ser Val Asp Ala Arg Phe Ser Ser Ser Thr
```

-continued

```
                100                 105                 110
Ser Ser Ile Thr Leu Arg Pro Ile Pro Ala Arg Gly Gly Asp Pro Lys
            115                 120                 125
Lys Ile Lys Val Leu Arg Ser Arg Arg Thr His Phe Ala Pro Arg Thr
            130                 135                 140
Ser His Phe Asp Arg His Asn Leu Thr Ser Ala Ser Asp Pro Phe Arg
145                 150                 155                 160
Gly Leu Tyr Thr Leu Phe Trp Ile Val Ile Phe Val Gly Ala Leu Lys
                165                 170                 175
Thr Val Tyr His Arg Phe Ala Glu Gln Gly Gly Trp Gly Gly Glu Trp
            180                 185                 190
Arg Phe Ala Ala Leu Ile Ser Arg Asp Gly Trp Val Leu Ala Val Ser
            195                 200                 205
Asp Ala Val Leu Val Ser Ala Ser Leu Leu Cys Val Pro Tyr Ala Lys
210                 215                 220
Leu Leu Val His Gly Trp Ile Arg Tyr His Gly Ala Gly Val Ile Ile
225                 230                 235                 240
Gln His Ile Cys Gln Thr Leu Tyr Leu Ala Ile Ala Ile Arg Trp Thr
                245                 250                 255
Phe His Arg Asn Trp Pro Trp Val Gln Ser Gly Phe Met Thr Leu His
                260                 265                 270
Ala Leu Ser Met Leu Met Lys Ile His Ser Tyr Cys Ser Leu Asn Gly
            275                 280                 285
Glu Leu Ser Glu Arg Arg Arg Gln Leu Arg Lys Asp Glu Gly Arg Leu
            290                 295                 300
Glu Glu Val Leu Glu Glu Met Gly Gly Arg Arg Ala Glu Arg Glu
305                 310                 315                 320
Ala Arg Glu Glu Trp Glu Arg Gln Cys Gly Glu Ala Ala Arg Ala Lys
                325                 330                 335
Glu Gly Glu Ala Gly Ser Arg Gly Lys Lys Glu Glu Val Ala Ala
            340                 345                 350
Gln Ser Ser Thr Asp Ala Ser Thr Ser Ala Leu Ser Ser Glu Asp Glu
            355                 360                 365
Ala Ala Ala Ala Leu Leu Arg His Arg Gln Ser Thr Ala Arg Arg Arg
            370                 375                 380
Ser Ile Ser Pro Ser Ala Ser Arg Thr His Ser Ser Ser Ala Ser Ser
385                 390                 395                 400
Ser His Pro Ala Pro Ser Arg Ala Glu Glu Pro Gln Glu Gly Val Glu
            405                 410                 415
Thr Leu Thr Trp His Pro Ser Asp Arg Val Ser Lys Leu Ala Ile Ala
            420                 425                 430
Ile Cys Glu Ala Lys Asp Leu Leu Thr Ser Asn Gly Lys Lys Pro Val
            435                 440                 445
Thr Phe Pro Glu Asn Val Thr Phe Ala Asn Phe Ile Asp Tyr Leu Leu
            450                 455                 460
Val Pro Thr Leu Val Tyr Glu Leu Tyr Pro Arg Thr Asp Ser Ile
465                 470                 475                 480
Arg Pro Leu Tyr Ile Leu Glu Lys Thr Leu Ala Thr Phe Gly Thr Phe
                485                 490                 495
Ser Ile Leu Val Leu Ile Val Asp Ser Phe Ile Leu Pro Val Thr Ser
            500                 505                 510
Arg Thr Asp Thr Pro Leu Phe Gly Phe Val Leu Asp Leu Ala Leu Pro
            515                 520                 525
```

```
Phe Thr Leu Ala Tyr Leu Leu Ile Phe Tyr Val Ile Phe Glu Gly Val
    530                 535                 540

Cys Asn Gly Phe Ala Glu Leu Thr Arg Phe Ala Asp Arg Asn Phe Phe
545                 550                 555                 560

Asp Asp Trp Trp Asn Ser Cys Thr Phe Asp Glu Phe Ser Arg Lys Trp
                565                 570                 575

Asn Arg Pro Val His Ala Phe Leu Leu Arg His Val Tyr Ala Glu Thr
            580                 585                 590

Met Ala Ser Tyr Lys Leu Ser Lys Leu Ser Ala Ala Phe Val Thr Phe
        595                 600                 605

Leu Phe Ser Ala Cys Val His Glu Leu Val Met Ala Val Val Thr Lys
    610                 615                 620

Lys Leu Arg Leu Tyr Leu Phe Ser Met Gln Met Ala Gln Leu Pro Leu
625                 630                 635                 640

Ile Met Val Gly Arg Ala Lys Ile Phe Arg Lys Tyr Pro Ala Leu Gly
                645                 650                 655

Asn Leu Phe Phe Trp Leu Ala Leu Leu Ser Gly Phe Pro Leu Leu Gly
            660                 665                 670

Thr Leu Tyr Leu Arg Tyr
            675

<210> SEQ ID NO 11
<211> LENGTH: 1929
<212> TYPE: DNA
<213> ORGANISM: Rhodosporidium toruloides
<220> FEATURE:
<221> NAME/KEY: CDS
<222> LOCATION: (111)..(1778)

<400> SEQUENCE: 11
acccttacac ccgtatgtcc cgacgagcag cagcacgagc tctctcagga ccactgctga    60
ccctcgcacg ctcgcgcgca ctccaaaccc gcctcttcca gcccacaacc atg tcc     116
                                                        Met Ser
                                                            1 gtc tcg acg aac gct atc ttc aag ctc ccg acc gtc aag aac gag ccc    164
Val Ser Thr Asn Ala Ile Phe Lys Leu Pro Thr Val Lys Asn Glu Pro
        5                  10                  15 aac ttc aac tat gcg cca ggc agc ccc gag cgc gcg gct ctt aag aag    212
Asn Phe Asn Tyr Ala Pro Gly Ser Pro Glu Arg Ala Ala Leu Lys Lys
 20                  25                  30 gcc ctc gcc gag ctc gag gcc gcc gcg ccg ttc gaa gtg ccc gcc ttc    260
Ala Leu Ala Glu Leu Glu Ala Ala Ala Pro Phe Glu Val Pro Ala Phe
35                  40                  45                  50 gtc ggc ggc aag gag gtc aag gtc tcg ggc gag cgc acc gag cag cct    308
Val Gly Gly Lys Glu Val Lys Val Ser Gly Glu Arg Thr Glu Gln Pro
                55                  60                  65 atg ccc cac aac cac aag aag gcg ctc tgc acc ttc gga acc tcg act    356
Met Pro His Asn His Lys Lys Ala Leu Cys Thr Phe Gly Thr Ser Thr
            70                  75                  80 cct gag ctc gcc agc cag gct atc gag gct gcg ctc gct gcc cag cct    404
Pro Glu Leu Ala Ser Gln Ala Ile Glu Ala Ala Leu Ala Ala Gln Pro
        85                  90                  95 gag tgg gag gct atg ccc ttc aac gac cgc gcc gcc atc ttc ttg agg    452
Glu Trp Glu Ala Met Pro Phe Asn Asp Arg Ala Ala Ile Phe Leu Arg
    100                 105                 110 gct gcc gac ctg atc agc ggc aag tac cgt gcc aag atc tgc gct gct    500
Ala Ala Asp Leu Ile Ser Gly Lys Tyr Arg Ala Lys Ile Cys Ala Ala
115                 120                 125                 130
```

```
acc atg ctc ggc cag ggc aag aac gtc tgg cag gcc gag att gac gcc    548
Thr Met Leu Gly Gln Gly Lys Asn Val Trp Gln Ala Glu Ile Asp Ala
        135                 140                 145 gct gcc gag ctc gcc gac ttc ttc cgc ttc ggc gcc gct cag gtc gag    596
Ala Ala Glu Leu Ala Asp Phe Phe Arg Phe Gly Ala Ala Gln Val Glu
            150                 155                 160 cag ctc tac gcg atg cag ccc acc gag aac tcg cct ggc gtc tgg aac    644
Gln Leu Tyr Ala Met Gln Pro Thr Glu Asn Ser Pro Gly Val Trp Asn
                165                 170                 175 cgc acc gag tac cgc ccg ctt gag ggt ttc gtc ttt gct gtc acc ccc    692
Arg Thr Glu Tyr Arg Pro Leu Glu Gly Phe Val Phe Ala Val Thr Pro
    180                 185                 190 ttc aac ttc acc gct atc ggc ggc aac ctc gtc ggc gct ccc gcg ctc    740
Phe Asn Phe Thr Ala Ile Gly Gly Asn Leu Val Gly Ala Pro Ala Leu
195                 200                 205                 210 acc gga aac gtc ctc gtc tgg aag ccc tcg ccc atg gcg acc tac tcc    788
Thr Gly Asn Val Leu Val Trp Lys Pro Ser Pro Met Ala Thr Tyr Ser
                215                 220                 225 tcg tgg ctc gtc ttc cag atc ctc ctt gag gcc ggt ctc ccc aag aac    836
Ser Trp Leu Val Phe Gln Ile Leu Leu Glu Ala Gly Leu Pro Lys Asn
            230                 235                 240 gtc atc cag ttc ctc ccc tgc cca aac ggc gac gcg acc atc tcg ctc    884
Val Ile Gln Phe Leu Pro Cys Pro Asn Gly Asp Ala Thr Ile Ser Leu
        245                 250                 255 gtt gac cgc gtc ctc tcg cac cgc atg ttc gcc ggt ctc cac ttc act    932
Val Asp Arg Val Leu Ser His Arg Met Phe Ala Gly Leu His Phe Thr
    260                 265                 270 ggc tcg acc cac gtc ttc cgc cac ctc tgg cag aag atc ggc aac aac    980
Gly Ser Thr His Val Phe Arg His Leu Trp Gln Lys Ile Gly Asn Asn
275                 280                 285                 290 atc aac aac tac ctc agc tac ccc cgc atc gtc ggc gag acc ggc gga    1028
Ile Asn Asn Tyr Leu Ser Tyr Pro Arg Ile Val Gly Glu Thr Gly Gly
                295                 300                 305 aag aac ttc cag ctc gtc cac ccc tct gcc aac gtc cgc gct gct gtc    1076
Lys Asn Phe Gln Leu Val His Pro Ser Ala Asn Val Arg Ala Ala Val
            310                 315                 320 acc ggt gcc atc cgc ggt gcc ttc gag tac cag ggc cag aag tgc tcg    1124
Thr Gly Ala Ile Arg Gly Ala Phe Glu Tyr Gln Gly Gln Lys Cys Ser
        325                 330                 335 gct ctc tcg cgt ctt tac gtc ccg aag ggt ctg tgg gag ggc gag ggc    1172
Ala Leu Ser Arg Leu Tyr Val Pro Lys Gly Leu Trp Glu Gly Glu Gly
    340                 345                 350 aag ttc aag gag atc ctt ctc tcc gag gtt gcc aag atc act ctc ggc    1220
Lys Phe Lys Glu Ile Leu Leu Ser Glu Val Ala Lys Ile Thr Leu Gly
355                 360                 365                 370 ccc gtc acc gag ttt gag cac ttc atg ggt ccc gtc atc tcg cag gct    1268
Pro Val Thr Glu Phe Glu His Phe Met Gly Pro Val Ile Ser Gln Ala
                375                 380                 385 tcg ttc gac aag tgc ctc agc tac gtt gag aag gcc aag cag gca ggt    1316
Ser Phe Asp Lys Cys Leu Ser Tyr Val Glu Lys Ala Lys Gln Ala Gly
            390                 395                 400 ggc gag gtc ctc gcc ggc ggc aag ggc gac gcg tcg agc ggt tac tac    1364
Gly Glu Val Leu Ala Gly Gly Lys Gly Asp Ala Ser Ser Gly Tyr Tyr
        405                 410                 415 gtc gag ccg acc atc atc ctg acc aag gac cct cgc tcg cct acc atg    1412
Val Glu Pro Thr Ile Ile Leu Thr Lys Asp Pro Arg Ser Pro Thr Met
    420                 425                 430 gtc gac gag atc ttc ggc ccg gtc ctc act gtt tac atc tac gag gac    1460
Val Asp Glu Ile Phe Gly Pro Val Leu Thr Val Tyr Ile Tyr Glu Asp
```

```
                435                 440                 445                 450
gac cag ttc gag gag acg tgc aag ttg atc gac cag acg acg acg tac    1508
Asp Gln Phe Glu Glu Thr Cys Lys Leu Ile Asp Gln Thr Thr Thr Tyr
                        455                 460                 465 gcc ctc act ggc tgc atc ttc tcg gac gac cgt gcc gcg act gtc aag    1556
Ala Leu Thr Gly Cys Ile Phe Ser Asp Asp Arg Ala Ala Thr Val Lys
            470                 475                 480 gcc ggt gct ctc ctc cgc cac gct gcg ggt aac tac tac atc aac gac    1604
Ala Gly Ala Leu Leu Arg His Ala Ala Gly Asn Tyr Tyr Ile Asn Asp
                485                 490                 495 aag tcg acc ggt gct gtt gtc ggt gcc cag cct ttc ggt ggc gca cgc    1652
Lys Ser Thr Gly Ala Val Val Gly Ala Gln Pro Phe Gly Gly Ala Arg
500                 505                 510 gga tcg ggc acg aac gac aag gcg ggc tcg atg acg ttc ttc acc cgc    1700
Gly Ser Gly Thr Asn Asp Lys Ala Gly Ser Met Thr Phe Phe Thr Arg
515                 520                 525                 530 tgg tgc cag ccg cgg agt gtg aag gaa tcc ttc tgc ccg ccc gaa tct    1748
Trp Cys Gln Pro Arg Ser Val Lys Glu Ser Phe Cys Pro Pro Glu Ser
                535                 540                 545 ttc cct tac ccg tcg aac cag cgc gat taa atggaggagt tggggaggag      1798
Phe Pro Tyr Pro Ser Asn Gln Arg Asp
                550                 555 gaggacgtcg agggagctgg ggaggcggag gacgtcgagg aggagttggg gaggagtttg   1858
tcgaggagga ggagaagggt ttctcctcgc ctgtagttgt acaaaatcag cacgcctttg   1918
cttccaccgc c                                                       1929

<210> SEQ ID NO 12
<211> LENGTH: 555
<212> TYPE: PRT
<213> ORGANISM: Rhodosporidium toruloides

<400> SEQUENCE: 12

Met Ser Val Ser Thr Asn Ala Ile Phe Lys Leu Pro Thr Val Lys Asn
1               5                   10                  15

Glu Pro Asn Phe Asn Tyr Ala Pro Gly Ser Pro Glu Arg Ala Ala Leu
            20                  25                  30

Lys Lys Ala Leu Ala Glu Leu Glu Ala Ala Pro Phe Glu Val Pro
        35                  40                  45

Ala Phe Val Gly Gly Lys Glu Val Lys Val Ser Gly Glu Arg Thr Glu
    50                  55                  60

Gln Pro Met Pro His Asn His Lys Lys Ala Leu Cys Thr Phe Gly Thr
65                  70                  75                  80

Ser Thr Pro Glu Leu Ala Ser Gln Ala Ile Glu Ala Ala Leu Ala Ala
                85                  90                  95

Gln Pro Glu Trp Glu Ala Met Pro Phe Asn Asp Arg Ala Ala Ile Phe
            100                 105                 110

Leu Arg Ala Ala Asp Leu Ile Ser Gly Lys Tyr Arg Ala Lys Ile Cys
        115                 120                 125

Ala Ala Thr Met Leu Gly Gln Gly Lys Asn Val Trp Gln Ala Glu Ile
    130                 135                 140

Asp Ala Ala Ala Glu Leu Ala Asp Phe Phe Arg Phe Gly Ala Ala Gln
145                 150                 155                 160

Val Glu Gln Leu Tyr Ala Met Gln Pro Thr Glu Asn Ser Pro Gly Val
                165                 170                 175

Trp Asn Arg Thr Glu Tyr Arg Pro Leu Glu Gly Phe Val Phe Ala Val
            180                 185                 190
```

Thr Pro Phe Asn Phe Thr Ala Ile Gly Gly Asn Leu Val Gly Ala Pro
            195                 200                 205

Ala Leu Thr Gly Asn Val Leu Val Trp Lys Pro Ser Pro Met Ala Thr
210                 215                 220

Tyr Ser Ser Trp Leu Val Phe Gln Ile Leu Leu Glu Ala Gly Leu Pro
225                 230                 235                 240

Lys Asn Val Ile Gln Phe Leu Pro Cys Pro Asn Gly Asp Ala Thr Ile
            245                 250                 255

Ser Leu Val Asp Arg Val Leu Ser His Arg Met Phe Ala Gly Leu His
            260                 265                 270

Phe Thr Gly Ser Thr His Val Phe Arg His Leu Trp Gln Lys Ile Gly
            275                 280                 285

Asn Asn Ile Asn Asn Tyr Leu Ser Tyr Pro Arg Ile Val Gly Glu Thr
290                 295                 300

Gly Gly Lys Asn Phe Gln Leu Val His Pro Ser Ala Asn Val Arg Ala
305                 310                 315                 320

Ala Val Thr Gly Ala Ile Arg Gly Ala Phe Glu Tyr Gln Gly Gln Lys
            325                 330                 335

Cys Ser Ala Leu Ser Arg Leu Tyr Val Pro Lys Gly Leu Trp Glu Gly
            340                 345                 350

Glu Gly Lys Phe Lys Glu Ile Leu Leu Ser Glu Val Ala Lys Ile Thr
            355                 360                 365

Leu Gly Pro Val Thr Glu Phe Glu His Phe Met Gly Pro Val Ile Ser
370                 375                 380

Gln Ala Ser Phe Asp Lys Cys Leu Ser Tyr Val Glu Lys Ala Lys Gln
385                 390                 395                 400

Ala Gly Gly Glu Val Leu Ala Gly Gly Lys Gly Asp Ala Ser Ser Gly
            405                 410                 415

Tyr Tyr Val Glu Pro Thr Ile Ile Leu Thr Lys Asp Pro Arg Ser Pro
            420                 425                 430

Thr Met Val Asp Glu Ile Phe Gly Pro Val Leu Thr Val Tyr Ile Tyr
            435                 440                 445

Glu Asp Asp Gln Phe Glu Glu Thr Cys Lys Leu Ile Asp Gln Thr Thr
450                 455                 460

Thr Tyr Ala Leu Thr Gly Cys Ile Phe Ser Asp Asp Arg Ala Ala Thr
465                 470                 475                 480

Val Lys Ala Gly Ala Leu Leu Arg His Ala Ala Gly Asn Tyr Tyr Ile
            485                 490                 495

Asn Asp Lys Ser Thr Gly Ala Val Val Gly Ala Gln Pro Phe Gly Gly
            500                 505                 510

Ala Arg Gly Ser Gly Thr Asn Asp Lys Ala Gly Ser Met Thr Phe Phe
            515                 520                 525

Thr Arg Trp Cys Gln Pro Arg Ser Val Lys Glu Ser Phe Cys Pro Pro
530                 535                 540

Glu Ser Phe Pro Tyr Pro Ser Asn Gln Arg Asp
545                 550                 555

<210> SEQ ID NO 13
<211> LENGTH: 1542
<212> TYPE: DNA
<213> ORGANISM: Marinobacter aquaeolei
<220> FEATURE:
<221> NAME/KEY: CDS
<222> LOCATION: (1)..(1542)

-continued

<400> SEQUENCE: 13

| | | | | | | | | | | | | | | | | |
|---|---|---|---|---|---|---|---|---|---|---|---|---|---|---|---|---|
| atg | gcc | atc | cag | cag | gtc | cac | cac | gcc | gac | acc | tcg | tcg | tcg | aag | gtc | 48 |
| Met | Ala | Ile | Gln | Gln | Val | His | His | Ala | Asp | Thr | Ser | Ser | Ser | Lys | Val | |
| 1 | | | | 5 | | | | | 10 | | | | | 15 | | |

| ctc | ggc | cag | ctc | cgc | ggc | aag | cgc | gtc | ctc | atc | acc | ggc | acc | acc | ggc | 96 |
|---|---|---|---|---|---|---|---|---|---|---|---|---|---|---|---|---|
| Leu | Gly | Gln | Leu | Arg | Gly | Lys | Arg | Val | Leu | Ile | Thr | Gly | Thr | Thr | Gly | |
| | | 20 | | | | | 25 | | | | | 30 | | | | |

| ttc | ctc | ggc | aag | gtc | gtc | ctc | gag | cgc | ctc | atc | cgc | gcc | gtc | ccg | gac | 144 |
|---|---|---|---|---|---|---|---|---|---|---|---|---|---|---|---|---|
| Phe | Leu | Gly | Lys | Val | Val | Leu | Glu | Arg | Leu | Ile | Arg | Ala | Val | Pro | Asp | |
| | 35 | | | | | 40 | | | | | 45 | | | | | |

| atc | ggc | gcc | atc | tac | ctc | ctc | atc | cgc | ggc | aac | aag | cgc | cac | ccg | gac | 192 |
|---|---|---|---|---|---|---|---|---|---|---|---|---|---|---|---|---|
| Ile | Gly | Ala | Ile | Tyr | Leu | Leu | Ile | Arg | Gly | Asn | Lys | Arg | His | Pro | Asp | |
| 50 | | | | | 55 | | | | | 60 | | | | | | |

| gcc | cgc | tcg | cgc | ttc | ctc | gag | gag | atc | gcc | acc | tcg | tcg | gtc | ttc | gac | 240 |
|---|---|---|---|---|---|---|---|---|---|---|---|---|---|---|---|---|
| Ala | Arg | Ser | Arg | Phe | Leu | Glu | Glu | Ile | Ala | Thr | Ser | Ser | Val | Phe | Asp | |
| 65 | | | | | 70 | | | | | 75 | | | | | 80 | |

| cgc | ctc | cgc | gag | gcc | gac | tcg | gag | ggc | ttc | gac | gcc | ttc | ctc | gag | gag | 288 |
|---|---|---|---|---|---|---|---|---|---|---|---|---|---|---|---|---|
| Arg | Leu | Arg | Glu | Ala | Asp | Ser | Glu | Gly | Phe | Asp | Ala | Phe | Leu | Glu | Glu | |
| | | | | 85 | | | | | 90 | | | | | 95 | | |

| cgc | atc | cac | tgc | gtc | acc | ggc | gag | gtc | acc | gag | gcc | ggc | ttc | ggc | atc | 336 |
|---|---|---|---|---|---|---|---|---|---|---|---|---|---|---|---|---|
| Arg | Ile | His | Cys | Val | Thr | Gly | Glu | Val | Thr | Glu | Ala | Gly | Phe | Gly | Ile | |
| | | | 100 | | | | | 105 | | | | | 110 | | | |

| ggc | cag | gag | gac | tac | cgc | aag | ctc | gcc | acc | gag | ctc | gac | gcc | gtc | atc | 384 |
|---|---|---|---|---|---|---|---|---|---|---|---|---|---|---|---|---|
| Gly | Gln | Glu | Asp | Tyr | Arg | Lys | Leu | Ala | Thr | Glu | Leu | Asp | Ala | Val | Ile | |
| | | 115 | | | | | 120 | | | | | 125 | | | | |

| aac | tcg | gcc | gcc | tcg | gtc | aac | ttc | cgc | gag | gag | ctc | gac | aag | gcc | ctc | 432 |
|---|---|---|---|---|---|---|---|---|---|---|---|---|---|---|---|---|
| Asn | Ser | Ala | Ala | Ser | Val | Asn | Phe | Arg | Glu | Glu | Leu | Asp | Lys | Ala | Leu | |
| | 130 | | | | | 135 | | | | | 140 | | | | | |

| gcc | atc | aac | acc | ctc | tgc | ctc | cgc | aac | atc | gcc | ggc | atg | gtc | gac | ctc | 480 |
|---|---|---|---|---|---|---|---|---|---|---|---|---|---|---|---|---|
| Ala | Ile | Asn | Thr | Leu | Cys | Leu | Arg | Asn | Ile | Ala | Gly | Met | Val | Asp | Leu | |
| 145 | | | | | 150 | | | | | 155 | | | | | 160 | |

| aac | ccg | aag | ctc | gcc | gtc | ctc | cag | gtc | tcg | acc | tgc | tac | gtc | aac | ggc | 528 |
|---|---|---|---|---|---|---|---|---|---|---|---|---|---|---|---|---|
| Asn | Pro | Lys | Leu | Ala | Val | Leu | Gln | Val | Ser | Thr | Cys | Tyr | Val | Asn | Gly | |
| | | | | 165 | | | | | 170 | | | | | 175 | | |

| atg | aac | tcg | ggc | cag | gtc | acc | gag | tcg | gtc | atc | aag | ccg | gcc | ggt | gag | 576 |
|---|---|---|---|---|---|---|---|---|---|---|---|---|---|---|---|---|
| Met | Asn | Ser | Gly | Gln | Val | Thr | Glu | Ser | Val | Ile | Lys | Pro | Ala | Gly | Glu | |
| | | | 180 | | | | | 185 | | | | | 190 | | | |

| gcg | gtc | ccg | cgc | tcg | ccg | gac | ggc | ttc | tac | gag | atc | gag | gag | ctc | gtc | 624 |
|---|---|---|---|---|---|---|---|---|---|---|---|---|---|---|---|---|
| Ala | Val | Pro | Arg | Ser | Pro | Asp | Gly | Phe | Tyr | Glu | Ile | Glu | Glu | Leu | Val | |
| | | 195 | | | | | 200 | | | | | 205 | | | | |

| cgc | ctc | ctc | cag | gac | aag | atc | gag | gac | gtc | cag | gcc | cgc | tac | tcg | ggc | 672 |
|---|---|---|---|---|---|---|---|---|---|---|---|---|---|---|---|---|
| Arg | Leu | Leu | Gln | Asp | Lys | Ile | Glu | Asp | Val | Gln | Ala | Arg | Tyr | Ser | Gly | |
| | 210 | | | | | 215 | | | | | 220 | | | | | |

| aag | gtc | ctc | gag | cgc | aag | ctc | gtc | gac | ctc | ggc | atc | cgc | gag | gcc | aac | 720 |
|---|---|---|---|---|---|---|---|---|---|---|---|---|---|---|---|---|
| Lys | Val | Leu | Glu | Arg | Lys | Leu | Val | Asp | Leu | Gly | Ile | Arg | Glu | Ala | Asn | |
| 225 | | | | | 230 | | | | | 235 | | | | | 240 | |

| cgc | tac | ggc | tgg | tcg | gac | acc | tac | acc | ttc | acc | aag | tgg | ctc | ggc | gag | 768 |
|---|---|---|---|---|---|---|---|---|---|---|---|---|---|---|---|---|
| Arg | Tyr | Gly | Trp | Ser | Asp | Thr | Tyr | Thr | Phe | Thr | Lys | Trp | Leu | Gly | Glu | |
| | | | | 245 | | | | | 250 | | | | | 255 | | |

| cag | ctc | ctt | atg | aag | gcc | ctc | aac | ggc | cgc | acc | ctc | acc | atc | ctc | cgc | 816 |
|---|---|---|---|---|---|---|---|---|---|---|---|---|---|---|---|---|
| Gln | Leu | Leu | Met | Lys | Ala | Leu | Asn | Gly | Arg | Thr | Leu | Thr | Ile | Leu | Arg | |
| | | | 260 | | | | | 265 | | | | | 270 | | | |

| ccg | tcg | atc | atc | gag | tcg | gcc | ctc | gag | gag | ccg | gcc | ccc | ggc | tgg | atc | 864 |
|---|---|---|---|---|---|---|---|---|---|---|---|---|---|---|---|---|
| Pro | Ser | Ile | Ile | Glu | Ser | Ala | Leu | Glu | Glu | Pro | Ala | Pro | Gly | Trp | Ile | |
| | | 275 | | | | | 280 | | | | | 285 | | | | |

| gag | ggc | gtc | aag | gtc | gcc | gac | gcc | atc | atc | ctc | gcc | tac | gcc | cgc | gag | 912 |
|---|---|---|---|---|---|---|---|---|---|---|---|---|---|---|---|---|
| Glu | Gly | Val | Lys | Val | Ala | Asp | Ala | Ile | Ile | Leu | Ala | Tyr | Ala | Arg | Glu | |
| | 290 | | | | | 295 | | | | | 300 | | | | | |

| aag | gtc | acc | ctc | ttc | ccc | ggc | aag | cgc | tcg | ggc | atc | atc | gac | gtc | atc | 960 |

```
Lys Val Thr Leu Phe Pro Gly Lys Arg Ser Gly Ile Ile Asp Val Ile
305                 310                 315                 320 ccg gtc gac ctc gtc gcc aac tcg atc atc ctc tcg ctc gcc gag gcc      1008
Pro Val Asp Leu Val Ala Asn Ser Ile Ile Leu Ser Leu Ala Glu Ala
                    325                 330                 335 ctc ggc gag ccg ggc cgc cgc cgc atc tac cag tgc tgc tcg ggc ggc      1056
Leu Gly Glu Pro Gly Arg Arg Arg Ile Tyr Gln Cys Cys Ser Gly Gly
                340                 345                 350 ggc aac ccg atc tcg ctc ggc gag ttc atc gac cac ctc atg gcc gag      1104
Gly Asn Pro Ile Ser Leu Gly Glu Phe Ile Asp His Leu Met Ala Glu
            355                 360                 365 tcg aag gcc aac tac gcc gcc tac gac cac ctc ttc tac cgc cag ccg      1152
Ser Lys Ala Asn Tyr Ala Ala Tyr Asp His Leu Phe Tyr Arg Gln Pro
        370                 375                 380 tcg aag ccg ttc ctc gcc gtc aac cgc gcc ctc ttc gac ctc gtc atc      1200
Ser Lys Pro Phe Leu Ala Val Asn Arg Ala Leu Phe Asp Leu Val Ile
385                 390                 395                 400 tcg ggc gtc cgc ctc ccg ctc tcg ctc acc gac cgc gtc ctc aag ctc      1248
Ser Gly Val Arg Leu Pro Leu Ser Leu Thr Asp Arg Val Leu Lys Leu
                405                 410                 415 ctc ggc aac tcg cgc gac ctc aag atg ctc cgc aac ctc gac acc acc      1296
Leu Gly Asn Ser Arg Asp Leu Lys Met Leu Arg Asn Leu Asp Thr Thr
                    420                 425                 430 cag tcg ctc gcc acc atc ttc ggc ttc tac acc gcc ccc gac tac atc      1344
Gln Ser Leu Ala Thr Ile Phe Gly Phe Tyr Thr Ala Pro Asp Tyr Ile
                435                 440                 445 ttc cgc aac gac gag ctc atg gcc ctc gcg aac cgc atg ggc gag gtc      1392
Phe Arg Asn Asp Glu Leu Met Ala Leu Ala Asn Arg Met Gly Glu Val
            450                 455                 460 gac aag ggc ctc ttc ccg gtc gac gcc cgc ctc atc gac tgg gag ctc      1440
Asp Lys Gly Leu Phe Pro Val Asp Ala Arg Leu Ile Asp Trp Glu Leu
465                 470                 475                 480 tac ctc cgc aag atc cac ctc gcc ggc ctc aac cgc tac gcc ctc aag      1488
Tyr Leu Arg Lys Ile His Leu Ala Gly Leu Asn Arg Tyr Ala Leu Lys
                485                 490                 495 gag cgc aag gtc tac tcg ctc aag act gcc cgc cag cgc aag aag gcc      1536
Glu Arg Lys Val Tyr Ser Leu Lys Thr Ala Arg Gln Arg Lys Lys Ala
                500                 505                 510 gcc tag                                                               1542
Ala

<210> SEQ ID NO 14
<211> LENGTH: 513
<212> TYPE: PRT
<213> ORGANISM: Marinobacter aquaeolei

<400> SEQUENCE: 14

Met Ala Ile Gln Gln Val His His Ala Asp Thr Ser Ser Ser Lys Val
1               5                   10                  15

Leu Gly Gln Leu Arg Gly Lys Arg Val Leu Ile Thr Gly Thr Thr Gly
                20                  25                  30

Phe Leu Gly Lys Val Val Leu Glu Arg Leu Ile Arg Ala Val Pro Asp
            35                  40                  45

Ile Gly Ala Ile Tyr Leu Leu Ile Arg Gly Asn Lys Arg His Pro Asp
        50                  55                  60

Ala Arg Ser Arg Phe Leu Glu Glu Ile Ala Thr Ser Ser Val Phe Asp
65                  70                  75                  80

Arg Leu Arg Glu Ala Asp Ser Glu Gly Phe Asp Ala Phe Leu Glu Glu
                85                  90                  95
```

```
Arg Ile His Cys Val Thr Gly Glu Val Thr Glu Ala Gly Phe Gly Ile
             100                 105                 110

Gly Gln Glu Asp Tyr Arg Lys Leu Ala Thr Glu Leu Asp Ala Val Ile
             115                 120                 125

Asn Ser Ala Ala Ser Val Asn Phe Arg Glu Leu Asp Lys Ala Leu
             130                 135                 140

Ala Ile Asn Thr Leu Cys Leu Arg Asn Ile Ala Gly Met Val Asp Leu
145                  150                 155                 160

Asn Pro Lys Leu Ala Val Leu Gln Val Ser Thr Cys Tyr Val Asn Gly
             165                 170                 175

Met Asn Ser Gly Gln Val Thr Glu Ser Val Ile Lys Pro Ala Gly Glu
             180                 185                 190

Ala Val Pro Arg Ser Pro Asp Gly Phe Tyr Glu Ile Glu Glu Leu Val
             195                 200                 205

Arg Leu Leu Gln Asp Lys Ile Glu Asp Val Gln Ala Arg Tyr Ser Gly
             210                 215                 220

Lys Val Leu Glu Arg Lys Leu Val Asp Leu Gly Ile Arg Glu Ala Asn
225                  230                 235                 240

Arg Tyr Gly Trp Ser Asp Thr Tyr Thr Phe Thr Lys Trp Leu Gly Glu
             245                 250                 255

Gln Leu Leu Met Lys Ala Leu Asn Gly Arg Thr Leu Thr Ile Leu Arg
             260                 265                 270

Pro Ser Ile Ile Glu Ser Ala Leu Glu Glu Pro Ala Pro Gly Trp Ile
             275                 280                 285

Glu Gly Val Lys Val Ala Asp Ala Ile Ile Leu Ala Tyr Ala Arg Glu
             290                 295                 300

Lys Val Thr Leu Phe Pro Gly Lys Arg Ser Gly Ile Ile Asp Val Ile
305                  310                 315                 320

Pro Val Asp Leu Val Ala Asn Ser Ile Ile Leu Ser Leu Ala Glu Ala
             325                 330                 335

Leu Gly Glu Pro Gly Arg Arg Ile Tyr Gln Cys Cys Ser Gly Gly
             340                 345                 350

Gly Asn Pro Ile Ser Leu Gly Glu Phe Ile Asp His Leu Met Ala Glu
             355                 360                 365

Ser Lys Ala Asn Tyr Ala Ala Tyr Asp His Leu Phe Tyr Arg Gln Pro
             370                 375                 380

Ser Lys Pro Phe Leu Ala Val Asn Arg Ala Leu Phe Asp Leu Val Ile
385                  390                 395                 400

Ser Gly Val Arg Leu Pro Leu Ser Leu Thr Asp Arg Val Leu Lys Leu
             405                 410                 415

Leu Gly Asn Ser Arg Asp Leu Lys Met Leu Arg Asn Leu Asp Thr Thr
             420                 425                 430

Gln Ser Leu Ala Thr Ile Phe Gly Phe Tyr Thr Ala Pro Asp Tyr Ile
             435                 440                 445

Phe Arg Asn Asp Glu Leu Met Ala Leu Ala Asn Arg Met Gly Glu Val
             450                 455                 460

Asp Lys Gly Leu Phe Pro Val Asp Ala Arg Leu Ile Asp Trp Glu Leu
465                  470                 475                 480

Tyr Leu Arg Lys Ile His Leu Ala Gly Leu Asn Arg Tyr Ala Leu Lys
             485                 490                 495

Glu Arg Lys Val Tyr Ser Leu Lys Thr Ala Arg Gln Arg Lys Lys Ala
             500                 505                 510
```

Ala

<210> SEQ ID NO 15
<211> LENGTH: 517
<212> TYPE: DNA
<213> ORGANISM: Rhodosporidium toruloides

<400> SEQUENCE: 15

```
cacgcctctg tgactcggta cggagagaga gagcgttggg ttgggttggg gattgtggcg      60
agcgaagggc gacccagcag ccagggagag ggagttggtc tggatgcaaa ccatgcgcat     120
ctcctctcgc agttgaatcg ttttcccgc tctgccctcg ctctctcttc cttctgctct     180
ttactcgctc acgaacaaca acgagccaca cagcgtgagc acacaccgct gcactcactc     240
gctgtcacgg accgcagctc acccttatcg tcactccctc tcccaccgca cagcctcact     300
ccctctctcg ctctccctca caagcacaac acacggcaca ctcgcacgca cactcgcacg     360
caatggccac cgtcaacgag aagcagcccc ccaccgacgc gccctcgcg cacgagaccg      420
ccatccaccg cgtgcgtccc catccctccc actgtcttcc tcgtgaaacc cgctcacccg     480
ttcgcaagca cacacgcagg tgtcggacta ccccgtg                              517
```

<210> SEQ ID NO 16
<211> LENGTH: 1429
<212> TYPE: DNA
<213> ORGANISM: Rhodosporidium toruloides

<400> SEQUENCE: 16

```
ctgcagaact acgccctctc acccaact tccgactcga ccggcggtac gagcacgacc       60
tacttctact gcctgccatc gacatccggg cgggtcgctg cctaccctgt gcgttctgcg     120
ccctccctcg tctcgggagg cagtgtctga cagaagcttt gcgcgcagta ccccgtcaag     180
atgcaactct acgcaacgtt cggcacagaa gtcgccaagc tccgcgcatc gccgcctcaa     240
gctctcgcgc tgcccgacgg tgtcgtctat tacgaggcgg agaagctcga gttgccggct     300
tgccagcgg cggtcaaggt tgaggtggag acggagaagg cgggagtagc ggggaggac       360
aatgaggcga agggtgagat ggtgctggtg gagactctta cggtggagca ggaggagatt     420
gaattgggct cgggagtcgt gcagattgag gagtcgttgc tcgtcaagct ggaggtcagc     480
ggctgatcct tccgttcgtt gcaaggatcg tctgcatgtt tcgcttctct caatgacaca     540
acctggagag cgctcccgtc agcgagaatc gaggacattc cgcagctcgt gagcaagcgg     600
aggtgcgagg ctcccctcgaa agctgcgcct cttcagacgg cttgttctct cctgctctgg    660
tgggctggcc tgacatgtaa tgtgctccgc cgcaagtccg tcgtcggtct caattcgacg     720
ttgaaagggc atagcgcaag gaagaaccct ctgcggacat gcagaattac tggctcgcct    780
gctccttcgt ctactggaat aagtcctgtc tcgttaaagc cccaacgtcg tttttcgacg    840
tttgtaaggc gcaagaggtg ctatgggcta cgcaggaagc tgagaggaca tagaagtcgg     900
gggaggaacg gcgcagagcg gcagttgcgg aagcatgagg aaagcgagac ggtccagcat     960
ctgcagcgcc aatccgcaat ctcctggttg agcctgcacc ggaagcgtcg gaacagtatg    1020
cgcagagtcg aacgcaagta agaaagacgc accctcacac tcgcttactt cgagccatac    1080
aacggatcaa agctgcgcgt atctcggctt gtaagggccg gaaagcaacc tcggagatgg    1140
acacgtcaca tcaccaactt atcgatctcg gccgtcgacg tcgcagagag ggcgagagaa    1200
gcggtgaagg agggaaacaa ccccctcgaga gcatgatccg accgaatctg cagcgcagga    1260
agccgttaca agcccgcctc gagcgcaggt cgggtccagc cggggacga aacgcgcgag     1320
```
gctgattcgt gagcgaagga agccgcatcg acaagttcgc tccccttttgc cctctttccc        1380 atcacccgtt ctcgccttac ccgctcagaa caacaccaga tcactcaca                     1429

<210> SEQ ID NO 17
<211> LENGTH: 1130
<212> TYPE: DNA
<213> ORGANISM: Rhodosporidium toruloides

<400> SEQUENCE: 17
gcacgcgaag cggtagaagc aatgaagcga ggcgagagcg agagaggcag ggcttcagcc          60
atgtccagct gatcggctgt aacgtcgcgc cgggccagtc tgttgaattt gttgcgtcgc         120
ctgagcgtaa tagaagtgca gtagtctact ccgcatgccg agaacgtcga agagcgcgaa         180
gtagggagtc gagggaagcg agggtggcaa acacagcaac gacaagcggt tccgcttcgc         240
tcaaaagctc gttgacgttg tttttgacgtt ttgaagacag tacaacagca gcaagaggcg        300
tgcgaagcgt tggtggcgag agcagcgaca aggaggaggag aatgagggag tggtggcgag        360
ggctcgcaaa cgggcgtacg cctcgaatgg agacgtgcga gtcgttcttc gacgtccgag         420
ggatgccgag cgccgagacg gagcacgcaa cgagcgagag gagagcagcc gcgcaaggtg         480
attcgagtgg cgcaagcgga ggacgacgag gagacggacg agggaggagg agggatggcg         540
agcgagcatc ggacggcggg gcgcgagaga cggcgtgagg agccgggtgt ggagagtttg         600
aggaggcgcg ggatgcgaag tggctgggtg tgcggagtga gcggtggcaa agagcgcact         660
tagagtctag agcgaggcag tagtagtaga gctgtatgaa tgaatacaaa gtgtgaatac         720
aacagtttgt aatgcgattc tgagcttgga cgtgtgcgcg cgagagggcg acttgcaagc         780
cagcgcccgc tcgctcttct tccttctgca cctcgcgtca accctcgcat ctcacaccta         840
cactcgcatt caaagtgcgt acactctccc acgacacacg gggacggcgc acaccaccgc         900
gcgtcgcttg aacggcgtcg ccacttcgag ccgtcactga cttcgtcctc gtcctccctc         960
ctctactctc ttgtactgta ctgtgtactg ggggggatag atgggcaagg aaaagggaca        1020
cgtcaacgtc gtcgttatcg gtacgttcag cgtcgtcgag gcgagtctgg cgaggaggag        1080
gacgtcgagc tgacctcgcc ccgtcctccc gcgcaggcca cgtcgactcc                   1130

<210> SEQ ID NO 18
<211> LENGTH: 21
<212> TYPE: DNA
<213> ORGANISM: Rhodosporidium toruloides

<400> SEQUENCE: 18
ccgccaataa cctcacctca g                                                    21

<210> SEQ ID NO 19
<211> LENGTH: 21
<212> TYPE: DNA
<213> ORGANISM: Rhodosporidium toruloides

<400> SEQUENCE: 19
ggcgatggga gcgtagaata c                                                    21

<210> SEQ ID NO 20
<211> LENGTH: 29
<212> TYPE: DNA
<213> ORGANISM: Rhodosporidium toruloides

<400> SEQUENCE: 20

-continued aaagagctca ctcactggcc tcctcgttc                              29

<210> SEQ ID NO 21
<211> LENGTH: 30
<212> TYPE: DNA
<213> ORGANISM: Rhodosporidium toruloides

<400> SEQUENCE: 21
aaaggatcca cgttgagagc ggagagggaa                             30

<210> SEQ ID NO 22
<211> LENGTH: 30
<212> TYPE: DNA
<213> ORGANISM: Rhodosporidium toruloides

<400> SEQUENCE: 22
tttaagcttg gaccaacgac tgcagaccat                             30

<210> SEQ ID NO 23
<211> LENGTH: 30
<212> TYPE: DNA
<213> ORGANISM: Rhodosporidium toruloides

<400> SEQUENCE: 23
tttaggcctg cccaacccga gaatgagctt                             30

<210> SEQ ID NO 24
<211> LENGTH: 28
<212> TYPE: DNA
<213> ORGANISM: Rhodosporidium toruloides

<400> SEQUENCE: 24
aaagagctca ttgaccctgc gtgtatgc                               28

<210> SEQ ID NO 25
<211> LENGTH: 30
<212> TYPE: DNA
<213> ORGANISM: Rhodosporidium toruloides

<400> SEQUENCE: 25
aaaggatccg tcttgagtgc tccgacgaag                             30

<210> SEQ ID NO 26
<211> LENGTH: 21
<212> TYPE: DNA
<213> ORGANISM: Rhodosporidium toruloides

<400> SEQUENCE: 26
tcgtcacgtt cttgttcagc g                                      21

<210> SEQ ID NO 27
<211> LENGTH: 29
<212> TYPE: DNA
<213> ORGANISM: Rhodosporidium toruloides

<400> SEQUENCE: 27
tttaggcctc gcctctacct cactcacgt                              29

<210> SEQ ID NO 28
<211> LENGTH: 30
<212> TYPE: DNA
<213> ORGANISM: Rhodosporidium toruloides

<400> SEQUENCE: 28
aaagagctcg cggaacagga gaacaaggag                                              30

<210> SEQ ID NO 29
<211> LENGTH: 30
<212> TYPE: DNA
<213> ORGANISM: Rhodosporidium toruloides

<400> SEQUENCE: 29
aaaggatccg ctcacgtcaa cactcccaaa                                              30

<210> SEQ ID NO 30
<211> LENGTH: 30
<212> TYPE: DNA
<213> ORGANISM: Rhodosporidium toruloides

<400> SEQUENCE: 30
tttaagctta gaaccactcg accgtcttca                                              30

<210> SEQ ID NO 31
<211> LENGTH: 29
<212> TYPE: DNA
<213> ORGANISM: Rhodosporidium toruloides

<400> SEQUENCE: 31
tttaggcctc tatcgacctc tcccaagcc                                               29

<210> SEQ ID NO 32
<211> LENGTH: 28
<212> TYPE: DNA
<213> ORGANISM: Rhodosporidium toruloides

<400> SEQUENCE: 32
tttaggcctc cagatcaggg tgagtcgt                                                28

<210> SEQ ID NO 33
<211> LENGTH: 27
<212> TYPE: DNA
<213> ORGANISM: Rhodosporidium toruloides

<400> SEQUENCE: 33
tttaagcttc ttgtggttgt ggggcat                                                 27

<210> SEQ ID NO 34
<211> LENGTH: 29
<212> TYPE: DNA
<213> ORGANISM: Rhodosporidium toruloides

<400> SEQUENCE: 34
aaaggatcct cactggctgc atcttctcg                                               29

<210> SEQ ID NO 35
<211> LENGTH: 20
<212> TYPE: DNA
<213> ORGANISM: Rhodosporidium toruloides

<400> SEQUENCE: 35
gtgtgcgatg actgtgtggt                                                         20

<210> SEQ ID NO 36
<211> LENGTH: 23
<212> TYPE: DNA
<213> ORGANISM: Rhodosporidium toruloides

```
<400> SEQUENCE: 36
ctgtagagga gctgcaggat caa                                          23

<210> SEQ ID NO 37
<211> LENGTH: 23
<212> TYPE: DNA
<213> ORGANISM: Rhodosporidium toruloides

<400> SEQUENCE: 37
cgagcttgat gaatccttttt cgt                                         23

<210> SEQ ID NO 38
<211> LENGTH: 21
<212> TYPE: DNA
<213> ORGANISM: Rhodosporidium toruloides

<400> SEQUENCE: 38
tgcagctccc ttctttcgct c                                            21

<210> SEQ ID NO 39
<211> LENGTH: 21
<212> TYPE: DNA
<213> ORGANISM: Rhodosporidium toruloides

<400> SEQUENCE: 39
atgctgtgcg agacgagaac c                                            21

<210> SEQ ID NO 40
<211> LENGTH: 21
<212> TYPE: DNA
<213> ORGANISM: Rhodosporidium toruloides

<400> SEQUENCE: 40
ctcgcaccca ctcttcttcc g                                            21

<210> SEQ ID NO 41
<211> LENGTH: 21
<212> TYPE: DNA
<213> ORGANISM: Rhodosporidium toruloides

<400> SEQUENCE: 41
ttccgatccg caaacctcgt c                                            21

<210> SEQ ID NO 42
<211> LENGTH: 21
<212> TYPE: DNA
<213> ORGANISM: Rhodosporidium toruloides

<400> SEQUENCE: 42
aaccaggaca cgatgggctt g                                            21

<210> SEQ ID NO 43
<211> LENGTH: 21
<212> TYPE: DNA
<213> ORGANISM: Rhodosporidium toruloides

<400> SEQUENCE: 43
tccttctcag tcgcgccaat g                                            21

<210> SEQ ID NO 44
<211> LENGTH: 21
<212> TYPE: DNA
<213> ORGANISM: Rhodosporidium toruloides
```

<400> SEQUENCE: 44
catgttcgcc ggtctccact t                                        21

<210> SEQ ID NO 45
<211> LENGTH: 21
<212> TYPE: DNA
<213> ORGANISM: Rhodosporidium toruloides

<400> SEQUENCE: 45
cctgcttggc cttctcaacg t                                        21

<210> SEQ ID NO 46
<211> LENGTH: 23
<212> TYPE: DNA
<213> ORGANISM: Rhodosporidium toruloides

<400> SEQUENCE: 46
tttccatggg ccagcaggcg acg                                      23

<210> SEQ ID NO 47
<211> LENGTH: 29
<212> TYPE: DNA
<213> ORGANISM: Rhodosporidium toruloides

<400> SEQUENCE: 47
tttgatatcg tccgttgcga ggaggtcag                                29

<210> SEQ ID NO 48
<211> LENGTH: 27
<212> TYPE: DNA
<213> ORGANISM: Rhodosporidium toruloides

<400> SEQUENCE: 48
ttttcatgag cacagtacgg aggcgca                                  27

<210> SEQ ID NO 49
<211> LENGTH: 32
<212> TYPE: DNA
<213> ORGANISM: Rhodosporidium toruloides

<400> SEQUENCE: 49
tttgtttaaa caggcgtaca gggtgggtca gc                            32

<210> SEQ ID NO 50
<211> LENGTH: 26
<212> TYPE: DNA
<213> ORGANISM: Rhodosporidium toruloides

<400> SEQUENCE: 50
tttccatggc ctcgctagac ccgcca                                   26

<210> SEQ ID NO 51
<211> LENGTH: 28
<212> TYPE: DNA
<213> ORGANISM: Rhodosporidium toruloides

<400> SEQUENCE: 51
tttgatatct gcgccctgag ctcagtac                                 28

<210> SEQ ID NO 52
<211> LENGTH: 29
<212> TYPE: DNA

<210> SEQ ID NO 52
<211> LENGTH: 29
<212> TYPE: DNA
<213> ORGANISM: Rhodosporidium toruloides

<400> SEQUENCE: 52
ttttcatgac cgtctcgacg aacgctatc                                29

<210> SEQ ID NO 53
<211> LENGTH: 30
<212> TYPE: DNA
<213> ORGANISM: Rhodosporidium toruloides

<400> SEQUENCE: 53
tttgatatct ccatttaatc gcgctggttc                               30

<210> SEQ ID NO 54
<211> LENGTH: 45
<212> TYPE: DNA
<213> ORGANISM: Rhodosporidium toruloides

<400> SEQUENCE: 54
agattgtcgt ttcccgcctt cagttttta ctagtggacg gcttg               45

<210> SEQ ID NO 55
<211> LENGTH: 65
<212> TYPE: DNA
<213> ORGANISM: Rhodosporidium toruloides

<400> SEQUENCE: 55
gtcgcacccc aaacgatgct gaaggctcgc aaacatgcta attcggggga tctggatttt    60
agtac                                                              65

<210> SEQ ID NO 56
<211> LENGTH: 57
<212> TYPE: DNA
<213> ORGANISM: Rhodosporidium toruloides

<400> SEQUENCE: 56
gcgagccttc agcatcgttt ggggtgcgac ctagtcacgc ctctgtgact cggtacg       57

<210> SEQ ID NO 57
<211> LENGTH: 65
<212> TYPE: DNA
<213> ORGANISM: Rhodosporidium toruloides

<400> SEQUENCE: 57
caatcaagat gtcgttgtgc tagtgtacgc aaacatgcta attcggggga tctggatttt    60
agtac                                                              65

<210> SEQ ID NO 58
<211> LENGTH: 54
<212> TYPE: DNA
<213> ORGANISM: Rhodosporidium toruloides

<400> SEQUENCE: 58
gcgtacacta gcacaacgac atcttgattg ctagtgcacg cgaagcggta gaag         54

<210> SEQ ID NO 59
<211> LENGTH: 45
<212> TYPE: DNA
<213> ORGANISM: Rhodosporidium toruloides

<400> SEQUENCE: 59
cgatactctc aaggtcagct cgaattgttt aaacatgcta attcg               45

<210> SEQ ID NO 60
<211> LENGTH: 2596
<212> TYPE: DNA
<213> ORGANISM: Rhodosporidium toruloides
<220> FEATURE:
<221> NAME/KEY: CDS
<222> LOCATION: (308)..(2509)

<400> SEQUENCE: 60

```
tctgcgcgag attcgcaact ggacgctcgt cgtcgccggc gaggtcgggg acgagtggcc      60
ggcagctgct cgcttctctt cctcgctcca acacaccgca gaacgtcgac ttcgcacttg     120
gatcgacgtt ggacagtcac agacaccaga ccctcgtcat cttcatctgc ctcgacacgc     180
ccgcacaccc ggctaccctc cttgcactct cacacttcac acagcgtcgc ctagccagtc     240
gccgcgcaac cacactcgca caccagcccc ctcgaaaccg catacccca ccttccctct      300
```

| tcacacg atg ccg act ccc ctc gcc gac acg cct acg ccc ccg acg ccc | 349 |
|---|---|
| Met Pro Thr Pro Leu Ala Asp Thr Pro Thr Pro Pro Thr Pro | |
| 1 5 10 | |

| atg gag acg atc gca aag gag cgc ttg aac ccg ccg ttc gac ctg cgc | 397 |
|---|---|
| Met Glu Thr Ile Ala Lys Glu Arg Leu Asn Pro Pro Phe Asp Leu Arg | |
| 15 20 25 30 | |

| cgc atg acc tac gcc atg ggc gac gga gag aag gag gtc aag ctg cgc | 445 |
|---|---|
| Arg Met Thr Tyr Ala Met Gly Asp Gly Glu Lys Glu Val Lys Leu Arg | |
| 35 40 45 | |

| gag aag cac atg atg gag atc cag cgg aat ccg ctc ttc cgc ctc gac | 493 |
|---|---|
| Glu Lys His Met Met Glu Ile Gln Arg Asn Pro Leu Phe Arg Leu Asp | |
| 50 55 60 | |

| gac atc cac gac ttg aca aag gac cag ctc cgc gag cgt acc atg gct | 541 |
|---|---|
| Asp Ile His Asp Leu Thr Lys Asp Gln Leu Arg Glu Arg Thr Met Ala | |
| 65 70 75 | |

| aag ttc tca aca atg gtg tcg tac gta tcg aac gag cga atc gac gag | 589 |
|---|---|
| Lys Phe Ser Thr Met Val Ser Tyr Val Ser Asn Glu Arg Ile Asp Glu | |
| 80 85 90 | |

| ttc cag aag cga atg aac gtc gtc tcc ctc gcc gac cct ggg ttc tgg | 637 |
|---|---|
| Phe Gln Lys Arg Met Asn Val Val Ser Leu Ala Asp Pro Gly Phe Trp | |
| 95 100 105 110 | |

| act cga ttt ggc gtc cat ttc ggt ttg ttc ctc ggc gcc atc cgg tca | 685 |
|---|---|
| Thr Arg Phe Gly Val His Phe Gly Leu Phe Leu Gly Ala Ile Arg Ser | |
| 115 120 125 | |

| ggc gca acc gcc aac cag atg agc tac tgg atg tcg aag ggc ctc ctc | 733 |
|---|---|
| Gly Ala Thr Ala Asn Gln Met Ser Tyr Trp Met Ser Lys Gly Leu Leu | |
| 130 135 140 | |

| ggc ttg aac ggc atg gtc ggc tgc ttc ggc atg acg gaa ctc gcg cac | 781 |
|---|---|
| Gly Leu Asn Gly Met Val Gly Cys Phe Gly Met Thr Glu Leu Ala His | |
| 145 150 155 | |

| ggc tca aac gtc gcc gga ctc gag acg acc gcg act ttt gac gag cag | 829 |
|---|---|
| Gly Ser Asn Val Ala Gly Leu Glu Thr Thr Ala Thr Phe Asp Glu Gln | |
| 160 165 170 | |

| acg gac gag ttt gtg att cac acg ccg agc gtc tcg gct acc aag tgg | 877 |
|---|---|
| Thr Asp Glu Phe Val Ile His Thr Pro Ser Val Ser Ala Thr Lys Trp | |
| 175 180 185 190 | |

| tgg att ggc ggc gcc gcc cac tcc gcc acg cac tgc tcc gtc ttc gcc | 925 |
|---|---|
| Trp Ile Gly Gly Ala Ala His Ser Ala Thr His Cys Ser Val Phe Ala | |
| 195 200 205 | |

| caa ctg atc gtc aaa ggc caa gtc tac ggc acg aag acc ttc atc gta | 973 |
|---|---|
| Gln Leu Ile Val Lys Gly Gln Val Tyr Gly Thr Lys Thr Phe Ile Val | |
| 210 215 220 | |

| ccc ctc cgc gaa ccg aag acg tac cag ctc ctg ccc gga gtc gcg att | 1021 |
|---|---|

```
Pro Leu Arg Glu Pro Lys Thr Tyr Gln Leu Leu Pro Gly Val Ala Ile
        225                 230                 235 ggc gat att ggg aag aag atg ggc agg gat ggg atc gat aat ggc tgg    1069
Gly Asp Ile Gly Lys Lys Met Gly Arg Asp Gly Ile Asp Asn Gly Trp
    240                 245                 250 atc caa ttc acc aac gtc cgc atc ccc cgc gcc tac atg ctc atg aag    1117
Ile Gln Phe Thr Asn Val Arg Ile Pro Arg Ala Tyr Met Leu Met Lys
255                 260                 265                 270 cac act caa gtc acg cgc gac ggc gag gtc cgc gag ccg ccc ctc gca    1165
His Thr Gln Val Thr Arg Asp Gly Glu Val Arg Glu Pro Pro Leu Ala
                275                 280                 285 cag ctc acg tac ggc gcg ctc ctc caa ggc cgg acg gcg atg gtt gcc    1213
Gln Leu Thr Tyr Gly Ala Leu Leu Gln Gly Arg Thr Ala Met Val Ala
        290                 295                 300 gac gct gcc aac gtc gcc aag aaa gct ttg acc att gcg att cgg tat    1261
Asp Ala Ala Asn Val Ala Lys Lys Ala Leu Thr Ile Ala Ile Arg Tyr
    305                 310                 315 gcg gcg gtc agg agg caa ttc aag gtc ggc gag aac aag ctc gag tcg    1309
Ala Ala Val Arg Arg Gln Phe Lys Val Gly Glu Asn Lys Leu Glu Ser
320                 325                 330 cag ctc ctc gac tac ccg atc cac cag cgc cgc ttg ccg ctc ctc        1357
Gln Leu Leu Asp Tyr Pro Ile His Gln Arg Arg Leu Leu Pro Leu Leu
335                 340                 345                 350 tcg cag gcc gtc gcg atg ggc ttc acc tcg tac cgc atg acc gct ctc    1405
Ser Gln Ala Val Ala Met Gly Phe Thr Ser Tyr Arg Met Thr Ala Leu
        355                 360                 365 ttc gag gaa atg agc ggc caa ctc gag tcg ctc ggg tcc gac tcg gac    1453
Phe Glu Glu Met Ser Gly Gln Leu Glu Ser Leu Gly Ser Asp Ser Asp
    370                 375                 380 gaa gcc gag act aag gag gtc ctc gag aaa ctc aag gag acg cat gcg    1501
Glu Ala Glu Thr Lys Glu Val Leu Glu Lys Leu Lys Glu Thr His Ala
385                 390                 395 acg agt gcg ggc ctc aag gcg ttt tgc acg tgg aac gcg ctc gag acg    1549
Thr Ser Ala Gly Leu Lys Ala Phe Cys Thr Trp Asn Ala Leu Glu Thr
        400                 405                 410 atc gag aag tgt cgg gcg tcg ctc ggt gga cac ggc tac tcg gcg tac    1597
Ile Glu Lys Cys Arg Ala Ser Leu Gly Gly His Gly Tyr Ser Ala Tyr
415                 420                 425                 430 tcg ggc ttg ccg ggc atg tac gcg gac cag gcg gtt cag tgc acc tgg    1645
Ser Gly Leu Pro Gly Met Tyr Ala Asp Gln Ala Val Gln Cys Thr Trp
            435                 440                 445 gag ggc gac aac acc atc ctc acg ctc cag tcc ggc cgc tcg ctg gtc    1693
Glu Gly Asp Asn Thr Ile Leu Thr Leu Gln Ser Gly Arg Ser Leu Val
        450                 455                 460 tcg tcg tac gcc gac gcc gtc aag ggc cag aag ctt ccc ggc ggc acc    1741
Ser Ser Tyr Ala Asp Ala Val Lys Gly Gln Lys Leu Pro Gly Gly Thr
    465                 470                 475 gcg tac ctg aac ggc ctc ccc ggc gtc ctg acc gcc tca tgc ccg tcg    1789
Ala Tyr Leu Asn Gly Leu Pro Gly Val Leu Thr Ala Ser Cys Pro Ser
480                 485                 490 gac gag gcg act ctc gac ctc aag acc ctc gag gcg ggc tgg gac acc    1837
Asp Glu Ala Thr Leu Asp Leu Lys Thr Leu Glu Ala Gly Trp Asp Thr
495                 500                 505                 510 gtc tct gcc aac gtc gtc cga cag gcg tac gaa aag ttc gag ggc gcg    1885
Val Ser Ala Asn Val Val Arg Gln Ala Tyr Glu Lys Phe Glu Gly Ala
            515                 520                 525 atg aag agt ggg aag gga agg gag gag gcg ctc gag ttg tgc tcg cag    1933
Met Lys Ser Gly Lys Gly Arg Glu Glu Ala Leu Glu Leu Cys Ser Gln
        530                 535                 540
```

```
gag cgg ttc gtt gcc gcg cgg gtg cac acc gct ggc tac atg ttc cgc       1981
Glu Arg Phe Val Ala Ala Arg Val His Thr Ala Gly Tyr Met Phe Arg
        545                 550                 555 atg ttc cac gag gcg ctc gtc gag ctc gcc aag gac gag cca aag gac       2029
Met Phe His Glu Ala Leu Val Glu Leu Ala Lys Asp Glu Pro Lys Asp
    560                 565                 570 aac ggc gtc atc aag acg ctc gac gac atc tgc cgc ctg tac ggc tgc       2077
Asn Gly Val Ile Lys Thr Leu Asp Asp Ile Cys Arg Leu Tyr Gly Cys
575                 580                 585                 590 tgg gct att gag gag aac gcc gcg cag ttc ctc aag tac aag ttc ttc       2125
Trp Ala Ile Glu Glu Asn Ala Ala Gln Phe Leu Lys Tyr Lys Phe Phe
                595                 600                 605 acc ccc aag cag atg gac atc atc tcc aac gag gtc acg agc ttg tgc       2173
Thr Pro Lys Gln Met Asp Ile Ile Ser Asn Glu Val Thr Ser Leu Cys
            610                 615                 620 gcc gag ctc cgc aag tgc gca gtc ttg ctc acc gac agc ttt ggc ttc       2221
Ala Glu Leu Arg Lys Cys Ala Val Leu Leu Thr Asp Ser Phe Gly Phe
        625                 630                 635 acc gac cac atc atc aac tcg cca ttc gga cgg tac gat ggc aac gtc       2269
Thr Asp His Ile Ile Asn Ser Pro Phe Gly Arg Tyr Asp Gly Asn Val
    640                 645                 650 tac gag tcg tac tac aac cag gtc aag gcg gcg aac ccg cac aac ccc       2317
Tyr Glu Ser Tyr Tyr Asn Gln Val Lys Ala Ala Asn Pro His Asn Pro
655                 660                 665                 670 gtc gcg ccg tac ttc gag cgc gtg atc cgg cct ctg atc gag cgc gag       2365
Val Ala Pro Tyr Phe Glu Arg Val Ile Arg Pro Leu Ile Glu Arg Glu
                675                 680                 685 ccg ctc gag ctc ggc gac gac gcc gac tcg atg gag ctc gac gac gag       2413
Pro Leu Glu Leu Gly Asp Asp Ala Asp Ser Met Glu Leu Asp Asp Glu
            690                 695                 700 att gcc gag atc cag gct gag cgg gag gag gag aag ggc gag gct gag       2461
Ile Ala Glu Ile Gln Ala Glu Arg Glu Glu Glu Lys Gly Glu Ala Glu
        705                 710                 715 acg gcg gac gag gca gag aag gag ttg aag aag cct gcc gag gag tga       2509
Thr Ala Asp Glu Ala Glu Lys Glu Leu Lys Lys Pro Ala Glu Glu
    720                 725                 730 tccgcctctc gccacgcatg tgtccctata ccgtgtacta gtgtctattc ctcgagctgc     2569
aactgtcgac aacaaagtat tccatcc                                         2596
```

<210> SEQ ID NO 61
<211> LENGTH: 733
<212> TYPE: PRT
<213> ORGANISM: Rhodosporidium toruloides

<400> SEQUENCE: 61

```
Met Pro Thr Pro Leu Ala Asp Thr Pro Thr Pro Pro Thr Pro Met Glu
1               5                   10                  15

Thr Ile Ala Lys Glu Arg Leu Asn Pro Pro Phe Asp Leu Arg Arg Met
            20                  25                  30

Thr Tyr Ala Met Gly Asp Gly Glu Lys Glu Val Lys Leu Arg Glu Lys
        35                  40                  45

His Met Met Glu Ile Gln Arg Asn Pro Leu Phe Arg Leu Asp Asp Ile
    50                  55                  60

His Asp Leu Thr Lys Asp Gln Leu Arg Glu Thr Met Ala Lys Phe
65                  70                  75                  80

Ser Thr Met Val Ser Tyr Val Ser Asn Glu Arg Ile Asp Glu Phe Gln
                85                  90                  95

Lys Arg Met Asn Val Val Ser Leu Ala Asp Pro Gly Phe Trp Thr Arg
```

```
                100                 105                 110
Phe Gly Val His Phe Gly Leu Phe Leu Gly Ala Ile Arg Ser Gly Ala
            115                 120                 125

Thr Ala Asn Gln Met Ser Tyr Trp Met Ser Lys Gly Leu Leu Gly Leu
            130                 135                 140

Asn Gly Met Val Gly Cys Phe Gly Met Thr Glu Leu Ala His Gly Ser
145                 150                 155                 160

Asn Val Ala Gly Leu Glu Thr Thr Ala Thr Phe Asp Glu Gln Thr Asp
                165                 170                 175

Glu Phe Val Ile His Thr Pro Ser Val Ser Ala Thr Lys Trp Trp Ile
            180                 185                 190

Gly Gly Ala Ala His Ser Ala Thr His Cys Ser Val Phe Ala Gln Leu
            195                 200                 205

Ile Val Lys Gly Gln Val Tyr Gly Thr Lys Thr Phe Ile Val Pro Leu
            210                 215                 220

Arg Glu Pro Lys Thr Tyr Gln Leu Leu Pro Gly Val Ala Ile Gly Asp
225                 230                 235                 240

Ile Gly Lys Lys Met Gly Arg Asp Gly Ile Asp Asn Gly Trp Ile Gln
                245                 250                 255

Phe Thr Asn Val Arg Ile Pro Arg Ala Tyr Met Leu Met Lys His Thr
            260                 265                 270

Gln Val Thr Arg Asp Gly Glu Val Arg Glu Pro Pro Leu Ala Gln Leu
            275                 280                 285

Thr Tyr Gly Ala Leu Leu Gln Gly Arg Thr Ala Met Val Ala Asp Ala
            290                 295                 300

Ala Asn Val Ala Lys Lys Ala Leu Thr Ile Ala Ile Arg Tyr Ala Ala
305                 310                 315                 320

Val Arg Arg Gln Phe Lys Val Gly Glu Asn Lys Leu Glu Ser Gln Leu
                325                 330                 335

Leu Asp Tyr Pro Ile His Gln Arg Arg Leu Leu Pro Leu Leu Ser Gln
            340                 345                 350

Ala Val Ala Met Gly Phe Thr Ser Tyr Arg Met Thr Ala Leu Phe Glu
            355                 360                 365

Glu Met Ser Gly Gln Leu Glu Ser Leu Gly Ser Asp Ser Asp Glu Ala
            370                 375                 380

Glu Thr Lys Glu Val Leu Glu Lys Leu Lys Glu Thr His Ala Thr Ser
385                 390                 395                 400

Ala Gly Leu Lys Ala Phe Cys Thr Trp Asn Ala Leu Glu Thr Ile Glu
                405                 410                 415

Lys Cys Arg Ala Ser Leu Gly Gly His Gly Tyr Ser Ala Tyr Ser Gly
            420                 425                 430

Leu Pro Gly Met Tyr Ala Asp Gln Ala Val Gln Cys Thr Trp Glu Gly
            435                 440                 445

Asp Asn Thr Ile Leu Thr Leu Gln Ser Gly Arg Ser Leu Val Ser Ser
            450                 455                 460

Tyr Ala Asp Ala Val Lys Gly Gln Lys Leu Pro Gly Gly Thr Ala Tyr
465                 470                 475                 480

Leu Asn Gly Leu Pro Gly Val Leu Thr Ala Ser Cys Pro Ser Asp Glu
                485                 490                 495

Ala Thr Leu Asp Leu Lys Thr Leu Glu Ala Gly Trp Asp Thr Val Ser
            500                 505                 510

Ala Asn Val Val Arg Gln Ala Tyr Glu Lys Phe Glu Gly Ala Met Lys
            515                 520                 525
```

```
Ser Gly Lys Gly Arg Glu Glu Ala Leu Glu Leu Cys Ser Gln Glu Arg
        530                 535                 540

Phe Val Ala Ala Arg Val His Thr Ala Gly Tyr Met Phe Arg Met Phe
545                 550                 555                 560

His Glu Ala Leu Val Glu Leu Ala Lys Asp Glu Pro Lys Asp Asn Gly
                565                 570                 575

Val Ile Lys Thr Leu Asp Asp Ile Cys Arg Leu Tyr Gly Cys Trp Ala
            580                 585                 590

Ile Glu Glu Asn Ala Ala Gln Phe Leu Lys Tyr Lys Phe Phe Thr Pro
        595                 600                 605

Lys Gln Met Asp Ile Ile Ser Asn Glu Val Thr Ser Leu Cys Ala Glu
    610                 615                 620

Leu Arg Lys Cys Ala Val Leu Leu Thr Asp Ser Phe Gly Phe Thr Asp
625                 630                 635                 640

His Ile Ile Asn Ser Pro Phe Gly Arg Tyr Asp Gly Asn Val Tyr Glu
                645                 650                 655

Ser Tyr Tyr Asn Gln Val Lys Ala Ala Asn Pro His Asn Pro Val Ala
            660                 665                 670

Pro Tyr Phe Glu Arg Val Ile Arg Pro Leu Ile Glu Arg Glu Pro Leu
        675                 680                 685

Glu Leu Gly Asp Asp Ala Asp Ser Met Glu Leu Asp Asp Glu Ile Ala
    690                 695                 700

Glu Ile Gln Ala Glu Arg Glu Glu Lys Gly Glu Ala Glu Thr Ala
705                 710                 715                 720

Asp Glu Ala Glu Lys Glu Leu Lys Lys Pro Ala Glu Glu
                725                 730

<210> SEQ ID NO 62
<211> LENGTH: 3327
<212> TYPE: DNA
<213> ORGANISM: Rhodosporidium toruloides

<400> SEQUENCE: 62
atgccgactc ccctcgccga cacgcctacg ccccgacgc ccatggagac gatcgcaaag   60
gagcgcttga acccgccgtt cgacctgcgc cgcatgacct acgccatggg cgacggagag  120
aagggtgcgt agcggcttac ttcttctcgc cggctttctc tttccctccg aagcttccgc  180
tttgaggaca gcacgctgac attgtgtgca cacgcagagg tcaagctgcg cgagaagcac  240
atgatggaga tccagcggaa tccgctcttc cgcctcgacg acatccacga cttgacaaag  300
gaccagctcc gcgagcgtac catggctaag ttgtgcgttc agctcattag actatgcgaa  360
caggcgaaag cgagggaccg ccgggcgaga cggtcctgcg tcttttcgct cactcttcag  420
gacttcccgg acttcgtgcg ctgtcgctga ctttcctccg cacatataca gctcaacaat  480
ggtgtcgtac gtatcgaacg agcgaatcga cgagttccag aaggtgcgcc cctcgtcctc  540
ctcgatttcc tcccgtcgcg cccggctgat cctctcctcc tcgcagcgaa tgaacgtcgt  600
ctccctcgcc gaccctgggt tctggactcg atttgtgagt gcgcactcat tccacctcgc  660
aggaagtcga agctgaccct cttacgtttc gcagggcgt acgttgaccc caggctgctt   720
cctggagacc gggcgatgat gctgactgct cttgtaatat ttccaagtcc atttcggttt  780
gtgggagtct cttttttatc gctctctcaa gctcccggga cttaccagtc gttttcggat  840
tcacagtcct cggcgccatc cggtcaggcg caaccgccaa ccagatggtc cgtcggctct  900
cattctctac tgcacggtac taaactgacg ctgtccgtcc tgcagagcta ctggatgtcg  960
```

```
aagggcctcc tcggcttgaa cggcatggtc ggctgcttcg gcatggtgcg cccgctcttc    1020
ctccccctcc tctcttcctt catccctatc agagctcgcg ctaacccctc atgcgcagac    1080
ggaactcgcg cacggctcaa acgtcgccgg actcgagacg accgcgactt ttgacgagca    1140
gacggacgag tttgtgattc acacgccgag cgtctcggct accaagtggt ggattggcgg    1200
tgcgttcgct tccgcctacc tttaggtgtc gaagagacgg tcgaactgac cttcgcaccc    1260
tcgcttccgc gcgcaggcgc cgcccactcc gccacgcact gctccgtctt cgcccaactg    1320
atcgtcaaag gccaagtcta cggcacgaag accttcatcg tacccctccg cgaaccgaag    1380
acgtaccagc tcctgcccgg agtcgcgatt ggcgatattg gaagaagat gggcagggat     1440 gggatcgata atggctggat gtgagtcgcc aactcgctcc attctagagc tgtgaaggat    1500
gcgacgctgc ggactgcacg gcgctgggtg atttcgatgt ggcgacctct tcgctgaccc    1560
tcggtctcca cgcacagcca attcaccaac gtccgcatcc cccgcgccta catgctcatg    1620
aagcacactc aagtcacgcg cgacggcgag gtccgcgagc cgcccctcgc acagctcacg    1680
tacggcgcgc tcctccaagg ccggacggcg atggttgccg acgctgccaa cgtcgccaag    1740
aaagctttga ccattgcgat tcggtatgcg gcggtcagga ggcaattcaa ggtcggcgag    1800
aacaaggtga gtccgcgcga acactgtggc ggaggtcttg cgctgacatt cacacgatcc    1860
cacagctcga gtcgcagctc ctcgactacc cgatccacca gcgccgcctc ttgccgctcc    1920
tctcgcaggc cgtcgcgatg ggcttcacct cgtaccgcat gaccgctctc ttcgaggaaa    1980
tgagcggcca actcgagtcg ctcgggtccg actcggacga agccgagact aaggaggtcc    2040
tcgagaaact caaggagacg catgcgacga gtgcgggcct caaggcgttt tgcacgtgga    2100
acgcgctcga gacgatcgag aagtgtcggg cgtcgctcgg tggacacggc tactcggcgt    2160
actcgggctt gccgggcatg tacgcggacc aggcggttca gtgcacctgg gagggcgaca    2220
acgtgcgtgc ccgcggcttt ccctcgagcg actccgtcga aacttggaca ctcacgctcc    2280
ccgcccgcag accatcctca cgctccagtc cggccgctcg ctggtctcgt cgtacgccga    2340
cgccgtcaag ggccagaagc ttccggcgg caccgcgtac ctgaacggcc tccccggcgt     2400
cctgaccgcc tcatgcccgt cggacgaggc gactctcgac ctcaagaccc tcgaggcggg    2460
ctgggacacc gtctctgcca acgtcgtccg acaggcgtac gaaaagttcg agggcgcgat    2520
gaagagtggg aagggaaggg aggaggcgct cgagttgtgc tcgcaggagc ggttcgttgc    2580
cgcgcgggtg cacaccgctg gctacatgtt ccggtgcgtc gcgctccttc acccctctc    2640 tagctctcga ctgacgcacc ccgacgcaca gcatgttcca cgaggcgctc gtcgagctcg    2700
ccaaggacga gccaaaggac aacggcgtca tcaagacgct cgacgacatc tgccgcctgt    2760
acggctgctg ggctattgag gagaacgccg cgcagttcct caagtacaag ttcttcaccc    2820
ccaagcagat ggacatcatc tccaacgagg tcggtcgcgg agactttcg tcaatcacga     2880 ggcagtcgct cacgcggttt cgtgcgcgtg caggtcacga gcttgtgcgc cgagctccgc    2940
aagtgcgcag tcttgctcac cgacagcttt ggcttcaccg accacatcgt gcgtcgcgca    3000
atgtctctcg tctacgcgct tcccaagctg acgtctcgcc tctcacggca gatcaactcg    3060
ccattcggac ggtacgatgg caacgtctac gagtcgtact acaaccaggt caaggcggcg    3120
aacccgcaca ccccgtcgc gccgtacttc gagcgcgtga tccggcctct gatcgagcgc    3180
```

```
gagccgctcg agctcggcga cgacgccgac tcgatggagc tcgacgacga gattgccgag    3240
atccaggctg agcgggagga ggagaagggc gaggctgaga cggcggacga ggcagagaag    3300
gagttgaaga agcctgccga ggagtga                                        3327
```

PRODUCTION OF FATTY ALCOHOLS IN RHODOSPORIDIUM

CROSS REFERENCE TO RELATED APPLICATION(S)

This application is a 35 U.S.C. § 371 National Stage of International Patent Application No. PCT/SG2018/050045, filed Jan. 29, 2018, designating the United States and claiming priority to U.S. provisional application No. 62/455,669, filed on Feb. 7, 2017. Each of these applications is incorporated by reference in its entirety.

SEQUENCE LISTING

The present application is being filed along with a Sequence Listing in electronic format. The Sequence Listing is entitled 2577258PCTSequenceListing.txt, created on 24 Jan. 2018 and is 112 kb in size. The information in the electronic format of the Sequence Listing is incorporated herein by reference in its entirety.

BACKGROUND OF THE INVENTION

The present invention relates to the field of fungal production fatty alcohols. More specifically, the present invention relates to the production of fatty alcohols in *Rhodosporidium*.

The publications and other materials used herein to illuminate the background of the invention or provide additional details respecting the practice, are incorporated by reference, and for convenience are respectively grouped in the Bibliography.

The term "lipid" is scientifically used to define fatty acids and their naturally-occurring derivatives (esters or amides) (Ratledge and Wilkinson, 1988a) as compared to its solubility property-related definition in general textbooks (Gunstone et al., 2012). Although the dominant oil and fat supplier in the world is derived from agricultural products, animal and marine sources, an increasing space is required for the potential production of fuels and chemical materials from microorganisms due to the depletion of oil resources and global warming. Furthermore, value-added single cell oil (SCO) produced from sustainable feedstock led to the comparably economic consideration of microbial factory with cheap plant products.

Lipid-producing microorganisms that can accumulate more than 20% or more of their biomass as lipids are termed as oleaginous, and there are very limited number of oleaginous microorganisms, e.g. only 25 oleaginous yeasts among 600 different yeast species (Ratledge and Wilkinson, 1988b). Triacyglycerides (TAGs) and steryl esters (SEs) are the major neutral lipids that represent the most important storage form of energy for eukaryotic cells (Beopoulos et al., 2012; Coleman and Lee, 2004; Czabany et al., 2007; Lung and Weselake, 2006; Sorger and Daum, 2003). Acyl-CoA: diacyglycerol acyltransferase (DGAT, EC 2.3.1.20), a transmembrane enzyme, acts in the final and committed step of TAG biosynthesis (FIG. 1), which has been proposed to be the rate-limiting enzyme in lipid accumulation (Yen et al., 2008). TAG can also be formed by an acyl-CoA-independent pathway, in which the phospholipid:diacylglycerol acyltransferase (PDAT, EC 2.3.1.158) is responsible for TAG biosynthesis using phosphatidylcholine as the acyl donor (Dahlqvist et al., 2000; Yoon et al., 2012). Recently, another two groups of DGAT, a bifunctional DGAT/wax ester synthase (ADP1) and a soluble form of DGAT, have been found in *Acinetobacter calcoaceticus* and peanut cotyledons for biosynthesis of wax (Kalscheuer and Steinbuchel, 2003) and 3-acetyl-1,2-diacyl-sn-glycerols (acTAG, an unusual TAG) (Chi et al., 2014), respectively. DGAT1 and DGAT2 are two of the enzymes DGATs responsible for the main part of TAG biosynthesis. Interestingly, DGAT2 family members don not show DNA or protein sequence similarities with DGAT1, and a comparative genomics study suggests that the DGAT1 and DGAT2 gene families are separated through evolution (Turchetto-Zolet et al., 2011).

*Rhodosporidium toruloides* (alias *Rhodotorula glutinis* or *Rhodotorula gracilis*), a member of Pucciniomycotina subphylum in the Basidiomycota, has been considered as an oleaginous and carotenogenic yeast (Ratledge and Wynn, 2002; Sampaio et al., 2003). *R. toruloides* is able to be cultured to extremely high cell density (>100 g/l dry cell mass) and accumulate more than 60% biomass as triglycerides, making it a good host for the production of oil for biodiesel and many other applications from biomass (Liu et al., 2009; Turcotte and Kosaric, 1988; Zhao et al., 2010). Moreover, *R. toruloides* can accumulate high amount of carotenoids. Recently, the carotenoid biosynthesis pathway and enzymes has been clarified in our lab (our submitted manuscript), which made it possible for either metabolic engineering to improve the yields of certain carotenoid compositions or application of the pigmentation as an easily traceable genetic marker as other carotenogenic fungi (Youssar and Avalos, 2007).

As widely used in versatile industrial products, oleochemicals are a class of lipid-derived aliphatic molecules (Biermann et al., 2011), which was dominantly produced from inexpensive lipid sources such as plant oils and animal fats recently (Pfleger et al., 2015). One alternative route for the bioconversion of the cheap oleochemical feedstocks to oleochemicals is to develop microbial biocatalysts through metabolic engineering (Keasling, 2010). Fatty alcohol, an important raw materials and consumer product with 2-3 times more expensive than free fatty acids and biodiesel (Pfleger et al., 2015), can be widely applied in detergent, lubricant, plastics and cosmetics industrials (Biermann et al., 2011; Noweck and Grafahrend, 2000). Similar as other oleochemicals, fatty alcohols are traditionally produced by chemical hydration method (Carlsson et al., 2011). Recently, the rising environmental concerns of chemical production method resulted in the enzymatic production of fatty alcohols in genetically engineering microbial hosts, where fatty acid acyl-CoA reductases (FARs) catalyze the reduction of different acyl-CoA molecules to the corresponding medium/long-chain alcohols (C8-C18). Two classes of FARs, alcohol- and aldehyde-forming, have been identified in many organisms. Recently, microbial production of fatty alcohols through metabolic engineering has been successfully achieved in *Escherichia coli* (Haushalter et al., 2015; Liu et al., 2013a; Youngquist et al., 2013; Zheng et al., 2012) and *Saccharomyces cerevisiae* (Tang and Chen, 2015). Very recently, oleaginous yeasts *R. toruloides* was successfully developed for the production of fatty alcohols by metabolic engineering, where the highest titer ever reported to date (8 g/L) was achieved by fed-batch fermentation (Fillet et al., 2015).

It is desired to develop oleaginous yeast with increased production of fatty alcohols.

SUMMARY OF THE INVENTION

The present invention relates to the field of fungal production of fatty alcohols. More specifically, the present invention relates to the production of fatty alcohols in *Rhodosporidium*.

Thus, in one aspect, the present invention provides a genetically modified host cell having down-regulation of four host cell triacylglycerol (TAG) synthases. In some embodiments, the host cell TAG synthases are type 1 acyl-CoA:diacylglycerol acyltransferase (Dga1), type 2 phospholipid:diacylglycerol acyltransferase (Lro1), acyl-CoA:sterol acyltransferase (steryl ester synthase, Are1), and type 3 soluble acyltransferase (Dga3). In some embodiments, the genetically modified host cell further has an overexpression of a heterologous fatty acyl-CoA reductase (FAR1; sometimes also referred to herein as FAR). In some embodiments, the coding sequence for FAR1 is codon modified for expression in the host cell. In some embodiments, the genetically modified host cell contains multiple copies of FAR1. In some embodiments, each copy of FAR1 is under control of the same or different promoters. In some embodiments, the genetically modified host cell further has down regulation of a host cell acyl-CoA oxidase 1 (Pox1).

In some embodiments, the genetically modified host cell comprises nucleic acid constructs, each comprising a nucleic acid sequence for down-regulating each of the TAG synthases described herein. In some embodiments, the genetically modified host cell comprises knocked-out host cell TAG synthases described herein. In some embodiments, the genetically modified host cell comprises a nucleic acid construct comprising a nucleic acid sequence for down-regulating a host cell Pox1. In some embodiments, the genetically modified host cell comprises a knocked-out host cell Pox1. In some embodiments, the genetically modified host cell comprises a nucleic acid construct comprising a promoter operatively linked to a heterologous nucleic acid sequence encoding FAR1. In some embodiments, the nucleic acid construct comprises multiple copies of FAR1 operatively linked to the same or different promoters. In some embodiments, the nucleic acid construct comprises three copies of FAR1 operatively linked to different promoters.

In some embodiments, the host cell is a cell of a *Rhodosporidium* species or a *Rhodotorula* species. In some embodiments, the host cell is a cell of a strain of *Rhodosporidium toruloides*. In some embodiments, the host cell is *R. toruloides* strain ATCC 10657.

In a second aspect, the present invention provides a method for producing fatty alcohols. In some embodiments, the method comprises growing the genetically modified host cells described herein in or on a suitable medium for growth of the genetically modified host cell and for production of fatty alcohols. In some embodiments, the genetically modified host cells are cultured in a culture medium described herein. In some embodiments, the genetically modified host cells are grown in a conical flask containing a culture medium described herein. In some embodiments the genetically modified host cells are cultured in the conical flasks at a temperature as described herein. In some embodiments, the conical flasks are shaken at a rate as described herein. In some embodiments, the genetically modified host cells are grown in a bioreactor containing a culture medium described herein.

BRIEF DESCRIPTION OF THE FIGURES

FIG. 2A: Schematic diagram of DGAT encoding genes. FIG. 2B: Southern blot analysis of DGAT gene deletion mutants.

FIG. 3A: Phylogenic tree of DGATs from various species. Abbreviation of species: Ac, *Acinetobacter calcoaceticus*; Ah, *Arachis hypogaea* (peanut); At, *Arabidopsis thaliana*; Hs, *Homo sapiens*; Pv, *Phaseolus vulgaris*; Rc, *Ricinus communis* (castor bean); Rt, *Rhodosporidium toruloides*; Sc, *Saccharomyces cerevisiae*; Yl, *Yarrowia lipolytica*; Vf, *Vernicia fordii* (Tung tree). FIG. 3B: Predicted transmembrane domains of Dga1, Lro1, Are1 and Dga3 from *R. toruloides*. The TMHMM web tools of the Center for Biological Sequence Analysis, Technical University of Denmark TMHMM Server plots the probability of the *R. toruloides* DGATs forming a transmembrane helix (0-1.0 on the y-axis).

FIG. 5A: Cell dry biomass of *R. toruloides* wild type (WT) and DGAT single and multiple gene deletion mutants. FIG. 5B: Relative lipid yields in *R. toruloides* WT and DGAT mutant strains. Lipid yield in WT strain was normalized to 100%. FIG. 5C: Fatty acid profiles in *R. toruloides* WT and DGAT mutant strains. (D) Lipid profiling of DGAT mutants through thin-layer chromatography. Cells were cultured in GJ2013 medium for 5 days with rotary shaking. The loading amount of lipids for TLC separation is 100 μg. All tests were performed by biological triplicates. Abbreviation of DGAT mutants: dl—Δdga1Δlro1; da—Δdga1Δare1; dla—Δdga1Δlro1Δare1; dlad—Δdga1Δlro1Δare1Δdga3. Abbreviation of lipid components: SE—sterol ester; TAG—triacylglycerol; FFA—free fatty acids; DAG—diacylglycerol; MAG: monoacylglycerol; PL—polar lipids.

Figure 8A:
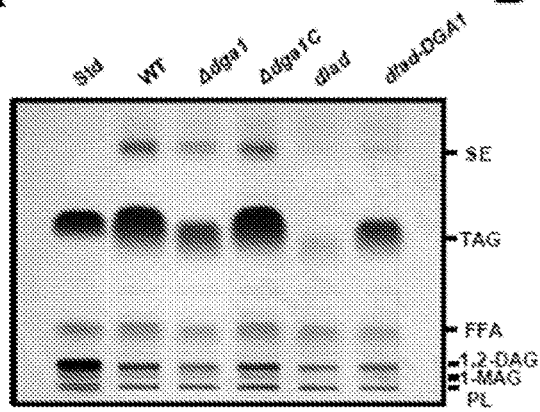
Figure 8B:
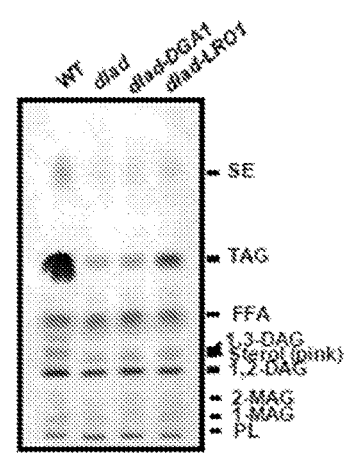
Figure 8C:
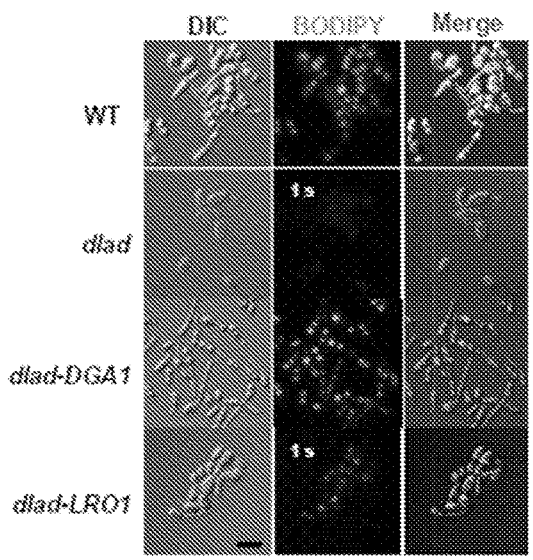
Figure 8D:
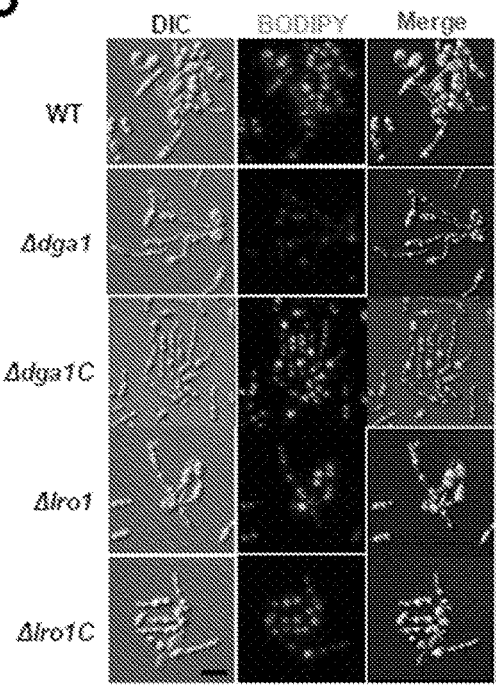

FIGS. 8A-8D show the overexpression of DGA1 and LRO1 in the null mutants. FIG. 8A: Effects of overexpression of DGA1 in Δdga1 (ΔdgaIC) and quadruple mutant dlad (dlad-DGA1) on lipid production. FIG. 8B: Effects of overexpression of LRO1 in quadruple mutant dlad (dlad-LRO1) on lipid production. FIG. 8C: Effects of overexpression of DGA1 and LRO1 in the quadruple mutant dlad on the formation of lipid bodies. FIG. 8D: Effects of Dga1 and Lro1 on the formation of lipid body. All cells cultured in MinRL3 medium for 5 days was used for the lipid extraction, TLC separation and microscopic observation. The loading amount of lipids for TLC separation is 100 μg. The exposure time for DIC and BODIPY staining fluorescent microscopy was 1/15 and 1/4 second, respectively, except the extension exposure time of 1 second on dlad series mutants as shown in the figure. Bar represents 10 μm. Abbreviations of DGAT mutants: dlad—Δdga1Δlro1Δare1Δdga3; dlad-DGA1—Δdga1Δlro1Δare1Δdga3-$P_{GPD1}$::DGA1:: $T35S^{CAR2}$; dlad-LRO1—Δdga1Δlro1Δare1Δdga3-$P_{GPD1}$::LRO1::$T35S^{CAR2}$; Δdga1C—Δdga1-$P_{GPD1}$::DGA1::$T35S^{CAR2}$; ΔLRO1C—Δlro1-$P_{GPD1}$::LRO1::$T35S^{CAR2}$. Abbreviations of lipid components: SE—sterol ester; TAG—triacylglycerol; FFA—free fatty acids; DAG—diacylglycerol; MAG: monoacylglycerol; PL—polar lipids. Abbreviations of Microscopy mode: DIC—differential interference contrast microscopy; BODIPY—fluorescent microscopy with excitation and emission wavelength of 488 and 509 nm, respectively (eGFP channel).

Figure 9:
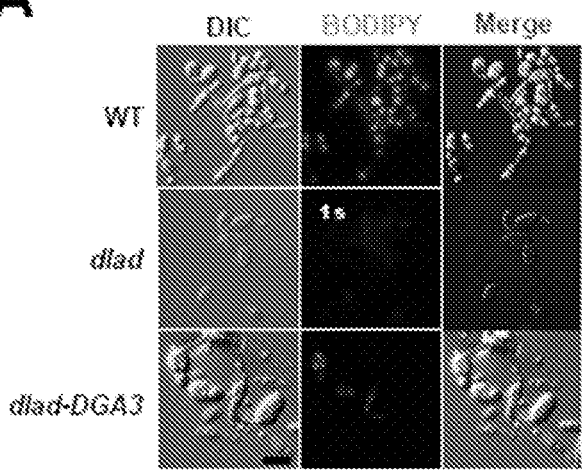
Figure 9:
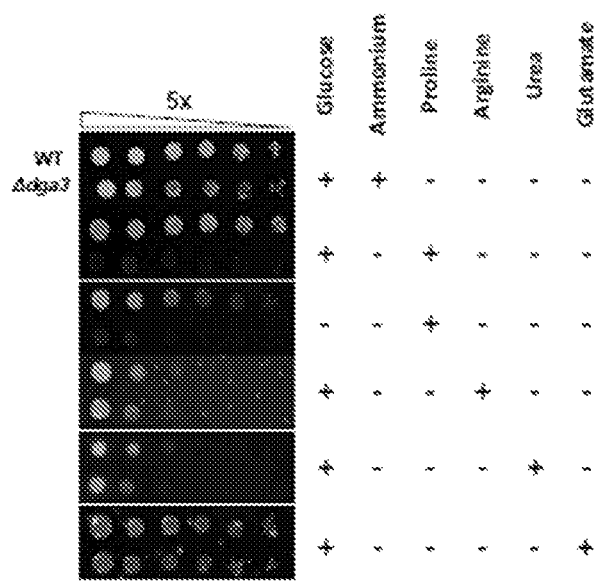
Figure 9:
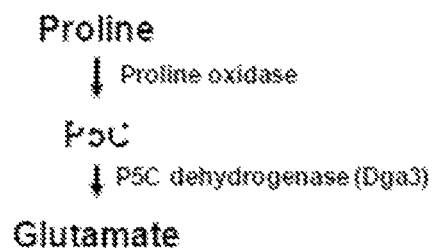

FIGS. 9A-9C show that Dga3 is a bifunctional enzyme, acyltransferase and $Δ^1$-pyrroline-5-carboxylate dehydrogenase. FIG. 9A: Effects of Dga3 on the formation of lipid body. DGA3 was constitutively expressed under the strong promoter GPD1 and reintroduced back into the quadruple mutant dlad. The exposure time for DIC and BODIPY staining fluorescent microscopy was 1/15 and 1/4 second, respectively, except the extension exposure time of 1 second on dlad series mutants as shown in the figure. Bar represents 10 μm. Abbreviations of DGAT mutants: dlad—Δdga1Δlro1Δare1Δdga3; dlad-DGA3—Δdga1Δlro1Δare1Δdga3-$P_{GPD1}$::DGA3::$T35S^{CAR2}$. (B) Drop assay of cell growth by serial dilution. A minimum medium (YNB) was used by supplementation of different carbon and nitrogen sources. FIG. 9B: In vitro enzyme assay of $Δ^1$-pyrroline-5-carboxylate dehydrogenase. FIG. 9C: Proline metabolism pathway.

Figure 10:
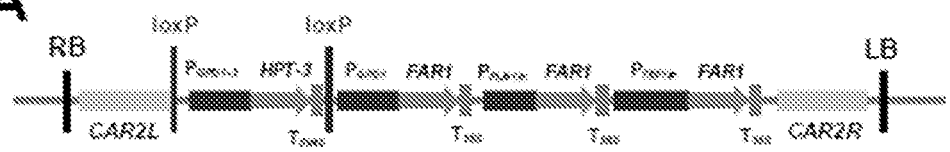
Figure 10:
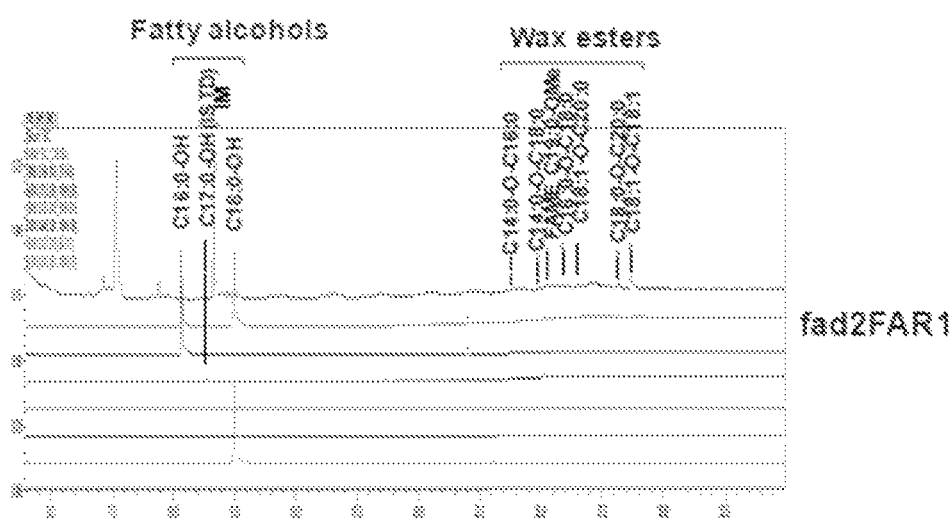
Figure 10:
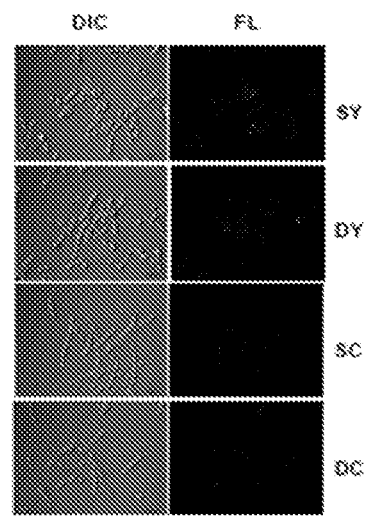

FIGS. 10A-10C show metabolic engineering of R. toruloides to produce fatty alcohols. FIG. 10A: Triple gene overexpression cassette (FAR1×3) in plasmid pKCGPT-FAR1. FIG. 10B: GC-MS separation and qualitative analysis of fatty alcohols and wax esters. FIG. 10C: Microscopic observation of lipid body formation through BODIPY staining. The best fatty alcohol producer dladpFAR1 was cultured in different media for 5 days, stained with BODIPY and observed under microscopy.

Figure 11A:
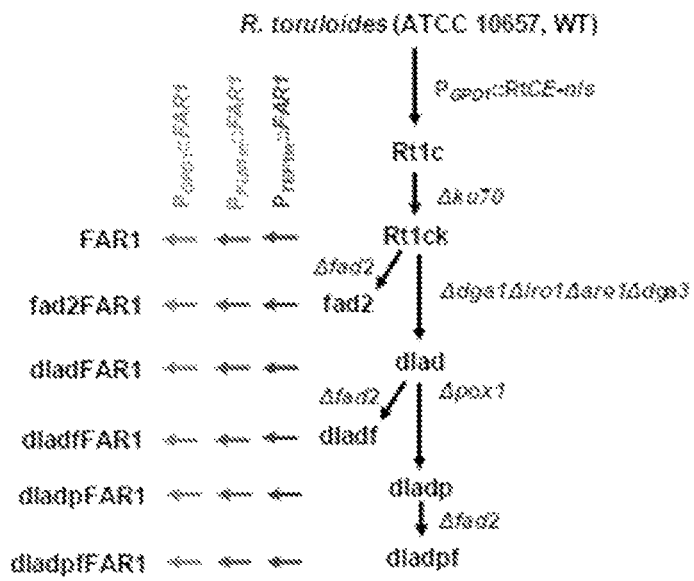
Figure 11B:
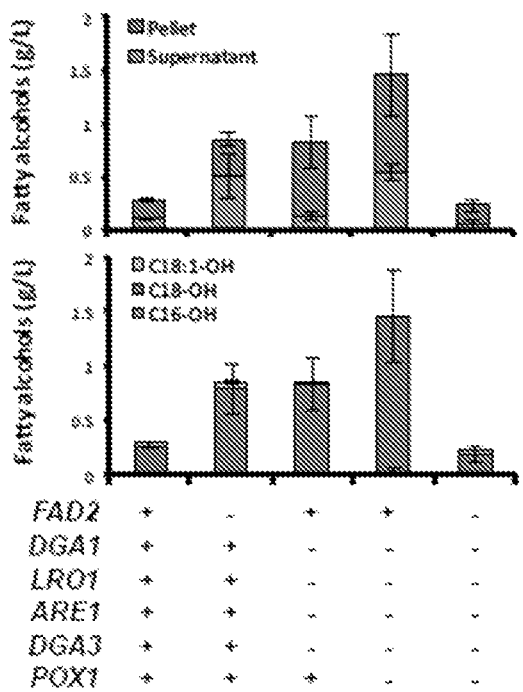

FIGS. 11A and 11B show metabolic engineering of fatty alcohol production in R. toruloides. FIG. 11A: Schematic diagram of metabolic engineering route for the production of fatty alcohol in R. toruloides. FIG. 11B: Fatty alcohol titers in different engineering mutants. All cells were cultured in GJm3 medium by shaking flask fermentation at 28° C., 280 rpm for 5 days. Abbreviations: RtCE-nls—Codon-optimized gene encoding a fusion protein of bacteriophage P1 Cre recombinase (C), human estrogen receptor α (E) and Simian virus 40 large antigen nuclear localization signal sequence (nls), this gene was regulated under the binding of estrogen and used for the excision of selection marker cassette by Cre/loxP recombination technique. Δku70—Deletion of KU70 gene to generate an elevated homologous recombination strain by defects in non-homologous end joining pathway. Δfad2—Deletion of Δ12,15 bifunctional fatty acid desaturase gene. Δdga1Δlro1Δare1Δdga3—Quadruple DGAT gene deletion mutant (lipid-less). Δpox1—Deletion of peroxisomal acyl-CoA oxisase 1 gene to block the degradation of fatty acids through β-oxidation pathway.

Figure 12A:
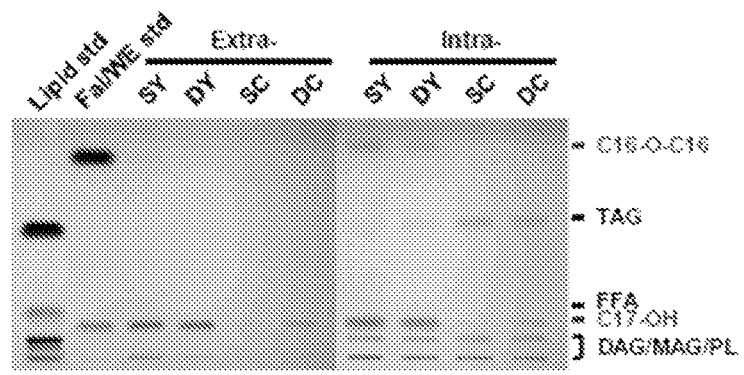
Figure 12B:
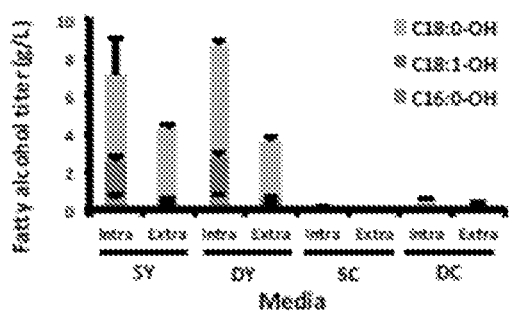

FIGS. 12A and 12B show an optimization of fatty alcohol production. FIG. 12A: TLC separation of extracted fatty alcohols from inside and outside of the cells (Intra- and Extra-, respectively). Lipid std is a mixture of TAG (10 mg/ml), 1,3-DAG, 1,2-DAG, 1-MAG and free fatty acids (each 1 mg/ml) as indicated in FIG. 8A. Fal/WE std is a mixture of palmityl palmitate (carbon 32 wax ester) and hexadecanol (carbon 17 fatty alcohol), each of 5 mg/ml. The amount of sample loading is 5 μl each and developing system is hexane:ethyl ether:acetic acid=80:20:1. FIG. 12B: Quantitation and profiling of extracted fatty alcohols after cultured in media with different carbon and nitrogen sources. SY—sucrose/yeast extract, DY—glucose/yeast extract, SC—sucrose/corn steep liquid, DY—glucose/corn steep liquid. C18:0-OH, C18:1-OH and C16:0-OH represents stearyl alcohol, oleyl alcohol and palmityl alcohol, respectively.

DETAILED DESCRIPTION

The present invention relates to the field of fungal production of α-eleosteric acid. More specifically, the present invention relates to the production of α-eleosteric acid in *Rhodosporidium*.

Unless defined otherwise, all technical and scientific terms used herein have the same meaning as is commonly understood by one of skill in the art to which the invention belongs.

The term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term "about" or "approximately" depends on the particular system under study, and can be readily appreciated by one of ordinary skill in the art.

A "control" or "control fungus" or "control fungal cell" provides a reference point for measuring changes in phenotype of a subject fungus or fungal cell in which genetic alteration, such as transformation, has been effected as to a polynucleotide of interest. A subject fungus or fungal cell may be descended from a fungus or fungal cell so altered and will comprise the alteration.

A control fungus or fungal cell may comprise, for example: (a) a wild-type fungus or fungal cell, i.e., of the same genotype as the starting material for the genetic alteration which resulted in the subject fungus or fungal cell; (b) a fungus or fungal cell of the same genotype as the starting material but which has been transformed with a null construct (i.e., with a construct which has no known effect on the trait of interest, such as a construct comprising a marker gene); (c) a fungus or fungal cell genetically identical to the subject fungus or fungal cell but which is not exposed to conditions or stimuli that would induce expression of the polynucleotide of interest or (d) the subject fungus or fungal cell itself, under conditions in which the polynucleotide of interest is not expressed.

"Constitutive promoter" refers to a promoter which is capable of causing a gene to be expressed in most cell types at most. A "strong constitutive promoter" refers to a constitutive promoter that drives the expression of a mRNA to the top 10% of any mRNA species in any given cell.

A "dsRNA" or "RNAi molecule," as used herein in the context of RNAi, refers to a compound, which is capable of down-regulating or reducing the expression of a gene or the activity of the product of such gene to an extent sufficient to achieve a desired biological or physiological effect. The term "dsRNA" or "RNAi molecule," as used herein, refers to one or more of a dsRNA, siRNA, shRNA, ihpRNA, synthetic shRNA, miRNA.

The term "down regulated," as it refers to genes inhibited by the subject RNAi method, refers to a diminishment in the level of expression of a gene(s) in the presence of one or more RNAi construct(s) when compared to the level in the absence of such RNAi construct(s). The term "down regulated" is used herein to indicate that the target gene expression is lowered by 1-100%. For example, the expression may be reduced by about 5%, 10%, 15%, 20%, 25%, 30%, 35%, 40%, 45%, 50%, 55%, 60%, 65%, 70%, 75%, 80%, 85%, 90%, 95%, or 99%.

The term "expression" with respect to a gene sequence refers to transcription of the gene and, as appropriate, translation of the resulting mRNA transcript to a protein. Thus, as will be clear from the context, expression of a protein coding sequence results from transcription and translation of the coding sequence.

As used herein, "gene" refers to a nucleic acid sequence that encompasses a 5' promoter region associated with the expression of the gene product, any intron and exon regions and 3' or 5' untranslated regions associated with the expression of the gene product.

As used herein, "genotype" refers to the genetic constitution of a cell or organism.

The term "heterologous" or "exogenous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous or exogenous protein indicates that the protein comprises two or more subsequences that are not found in the same relationship to each other in nature (e.g., a fusion protein).

"Inducible promoter" refers to a promoter which is capable of directly or indirectly activating transcription of one or more DNA sequences or genes in response to an inducer. The inducer can be a chemical agent such as a protein, metabolite, growth regulator, herbicide or phenolic compound or a physiological stress, such as that imposed directly by heat, cold, salt or toxic elements or indirectly through the action of a pathogen or disease agent such as a virus or other biological or physical agent or environmental condition.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Knock-out" or "knockout" as used herein refers to a gene that is or has been made inoperative. Knock-out or gene knock-out refers to an inhibition or substantial suppression of endogenous gene expression either by a transgenic or a non-transgenic approach. For example, knock-outs can be achieved by a variety of approaches including transposons, retrotransposons, deletions, substitutions, mutagenesis of the endogenous coding sequence and/or a regulatory sequence such that the expression is substantially suppressed; and any other methodology that suppresses the activity of the target of interest.

"Operable linkage" or "operably linked" or "operatively linked" as used herein is understood as meaning, for example, the sequential arrangement of a promoter and the nucleic acid to be expressed and, if appropriate, further regulatory elements such as, for example, a terminator, in such a way that each of the regulatory elements can fulfill its function in the recombinant expression of the nucleic acid to make dsRNA. This does not necessarily require direct linkage in the chemical sense. Genetic control sequences such as, for example, enhancer sequences, can also exert their function on the target sequence from positions which are somewhat distant, or indeed from other DNA molecules (cis or trans localization). Preferred arrangements are those in which the nucleic acid sequence to be expressed recombinantly is positioned downstream of the sequence which acts as promoter, so that the two sequences are covalently bonded with one another. Regulatory or control sequences may be positioned on the 5' side of the nucleotide sequence or on the 3' side of the nucleotide sequence as is well known in the art.

"Over-expression" or "overexpression" refers to the production of a gene product in transgenic organisms that exceeds levels of production in normal, control or non-transformed organisms.

As used herein, "phenotype" refers to the detectable characteristics of a cell or organism, which characteristics are the manifestation of gene expression.

The terms "polynucleotide," "nucleic acid" and "nucleic acid molecule" are used interchangeably herein to refer to a polymer of nucleotides which may be a natural or synthetic linear and sequential array of nucleotides and/or nucleosides, including deoxyribonucleic acid, ribonucleic acid, and derivatives thereof. It includes chromosomal DNA, self-replicating plasmids, infectious polymers of DNA or RNA and DNA or RNA that performs a primarily structural role. Unless otherwise indicated, nucleic acids or polynucleotide are written left to right in 5' to 3' orientation, Nucleotides are referred to by their commonly accepted single-letter codes. Numeric ranges are inclusive of the numbers defining the range.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. Amino acids may be referred to by their commonly known three-letter or one-letter symbols. Amino acid sequences are written left to right in amino to carboxy orientation, respectively. Numeric ranges are inclusive of the numbers defining the range.

"Promoter" refers to a nucleic acid fragment capable of controlling transcription of another nucleic acid fragment.

"Promoter functional in a fungus" is a promoter capable of controlling transcription in fungal cells whether or not its origin is from a fungal cell.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature. The terms "recombinant DNA construct" and "recombinant construct" are used interchangeably herein. A suppression DNA construct, used herein, is a type of recombinant DNA construct. In several embodiments described herein, a recombinant DNA construct may also be considered an "over expression DNA construct."

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transformation" as used herein refers to both stable transformation and transient transformation.

A "transformed cell" is any cell into which a nucleic acid fragment (e.g., a recombinant DNA construct) has been introduced.

"Transgenic fungus" includes reference to a fungus which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct. "Transgenic fungus" also includes reference to fungi which comprise more than one heterologous polynucleotide within their genome. A "transgenic fungus" encompasses all descendants which continue to harbor the foreign DNA.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) *CABIOS.* 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Alternatively, the Clustal W method of alignment may be used. The Clustal W method of alignment (described by Higgins and Sharp, CABIOS. 5:151-153 (1989); Higgins, D. G. et al., Comput. Appl. Biosci. 8:189-191 (1992)) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB. After alignment of the sequences using the Clustal W program, it is possible to obtain "percent identity" and "divergence" values by viewing the "sequence distances" table in the same program.

The term "under stringent conditions" means that two sequences hybridize under moderately or highly stringent conditions. More specifically, moderately stringent conditions can be readily determined by those having ordinary skill in the art, e.g., depending on the length of DNA. The basic conditions are set forth by Sambrook et al., *Molecular Cloning: A Laboratory Manual*, third edition, chapters 6 and 7, Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50° C. (or other similar hybridization solutions, such as Stark's solution, in about 50% formamide at about 42° C.) and washing conditions of, for example, about 40-60° C., 0.5-6×SSC, 0.1% SDS. Preferably, moderately stringent conditions include hybridization (and washing) at about 50° C. and 6×SSC. Highly stringent conditions can also be readily determined by those skilled in the art, e.g., depending on the length of DNA.

Generally, such conditions include hybridization and/or washing at higher temperature and/or lower salt concentration (such as hybridization at about 65° C., 6×SSC to 0.2×SSC, preferably 6×SSC, more preferably 2×SSC, most preferably 0.2×SSC), compared to the moderately stringent conditions. For example, highly stringent conditions may include hybridization as defined above, and washing at approximately 65-68° C., 0.2×SSC, 0.1% SDS. SSPE (1×SSPE is 0.15 M NaCl, 10 mM $NaH_2PO_4$, and 1.25 mM EDTA, pH 7.4) can be substituted for SSC (1×SSC is 0.15 M NaCl and 15 mM sodium citrate) in the hybridization and washing buffers; washing is performed for 15 minutes after hybridization is completed.

It is also possible to use a commercially available hybridization kit which uses no radioactive substance as a probe. Specific examples include hybridization with an ECL direct labeling & detection system (Amersham). Stringent conditions include, for example, hybridization at 42° C. for 4 hours using the hybridization buffer included in the kit, which is supplemented with 5% (w/v) Blocking reagent and 0.5 M NaCl, and washing twice in 0.4% SDS, 0.5×SSC at 55° C. for 20 minutes and once in 2×SSC at room temperature for 5 minutes.

Thus, in one aspect, the present invention provides a genetically modified host cell having down-regulation of four host cell triacylglycerol (TAG) synthases. In some embodiments, the host cell TAG synthases are type 1 acyl-CoA:diacylglycerol acyltransferase (Dga1), type 2 phospholipid:diacylglycerol acyltransferase (Lro1), acyl-CoA:sterol acyltransferase (steryl ester synthase, Are1), and type 3 soluble acyltransferase (Dga3). In some embodiments, the genetically modified host cell further has an overexpression of a heterologous fatty acyl-CoA reductase (FAR1). In some embodiments, the coding sequence for FAR1 is codon modified for expression in the host cell. In some embodiments, the genetically modified host cell contains multiple copies of FAR1. In some embodiments, each copy of FAR1 is under control of the same or different promoters. In some embodiments, the genetically modified host cell further has down regulation of a host cell acyl-CoA oxidase 1 (Pox1).

In some embodiments, the genetically modified host cell comprises nucleic acid constructs, each comprising a nucleic acid sequence for down-regulating each of the TAG synthases described herein. In some embodiments, the genetically modified host cell comprises knocked-out host cell TAG synthases described herein. In some embodiments, the genetically modified host cell comprises a nucleic acid construct comprising a nucleic acid sequence for down-regulating a host cell Pox1. In some embodiments, the genetically modified host cell comprises a knocked-out host cell Pox1. In some embodiments, the genetically modified host cell comprises a nucleic acid construct comprising a promoter operatively linked to a heterologous nucleic acid sequence encoding FAR1. In some embodiments, the nucleic acid construct comprises multiple copies of FAR1 operatively linked to the same or different promoters, such as those described herein. In some embodiments, the nucleic acid construct comprises three copies of FAR1 operatively linked to different promoters, such as those described herein.

In some embodiments, the invention provides a genetically modified fungal cell useful for producing fatty alcohols that comprises (a) a nucleic acid construct that overexpresses a heterologous fatty acyl-CoA reductase (FAR1); (b) either (i) a nucleic acid construct for down-regulating a host cell type 1 acyl-CoA:diacylglycerol acyltransferase (Dga1) or (ii) a knocked-out host cell Dga1 gene or a combination of (i) and (ii); (c) either (i) a nucleic acid construct for down-regulating a host cell type 2 phospholipid:diacylglycerol acyltransferase (Lro1) or (ii) a knocked-out host cell Lro1 gene or a combination of (i) and (ii); (d) either (i) a nucleic acid construct for down-regulating a host cell acyl-CoA:sterol acyltransferase (steryl ester synthase, Are1) or (ii) a knocked-out host cell Are1 gene or a combination of (i) and (ii); and (e) either (i) a nucleic acid construct for down-regulating a host cell type 3 soluble acyltransferase (Dga3) or (ii) a knocked-out host cell Dga3 gene or a combination of (i) and (ii). In some embodiments, the genetically modified fungal cell further comprises (f) either (i) a nucleic acid construct for down-regulating a host cell acyl-CoA oxidase 1 (Pox1) or (ii) a knocked-out host cell Pox1 gene or a combination of (i) and (ii). In some embodiments, the genetic background of the genetically modified host cells is $FAD^+$, $FAR1^+$, $\Delta dga1$, $\Delta lro1$, $\Delta are1$, $\Delta dga3$ and optionally $\Delta pox1$.

In some embodiments, the heterologous FAR1 coding sequence(s) is (are) operatively linked to a strong constitutive promoter. In some embodiments, suitable strong constitutive promoters are described in WO 2012/169969, incorporated by reference herein in its entirety, which describes several polynucleotide sequences derived from the upstream region of glyceraldehyde phosphate dehydrogenase gene (GPD1), translation initiation factor gene (TEF), and putative stearoyl-CoA-delta 9-desaturase gene (FAD1) of selected fungal species that are able to function as a strong promoter of gene expression in Pucciniomycotina and Ustilaginomycotina subphyla, including *Rhodosporidium*. In some embodiments, suitable strong constitutive promoters are described in WO 2014/142747, incorporated by reference herein in its entirety, which describes several polynucleotide sequences that function as strong promoters of gene expression in *Rhodosporidium, Rhodotorula, Sporobolomyces, Pseudozyma* and *Ustilago* genera. In some embodiments, suitable strong constitutive promoters are described in U.S. patent application No. 62/292,030 filed on 5 Feb. 2016, incorporated herein by reference it its entirety, which describes intron-containing promoters that are capable of driving strong expression of RNA or proteins in species of the *Rhodosporidium* or *Rhodotorula* genera.

In some embodiments, the strong constitutive promoter is the $RtPLN1_{in}$ promoter. In some embodiments the $RtPLN1_{in}$ promoter comprises the sequence set forth in SEQ ID NO:15. In some embodiments, the strong constitutive promoter is the RtGPD1 promoter. In some embodiments the RtGPD1 promoter comprises the sequence set forth in SEQ ID NO:16. In some embodiments, the strong constitutive promoter is the $RtTEF1_{in}$ promoter. In some embodiments, the $RtTEF1_{in}$ promoter comprises the sequence set forth in SEQ ID NO:17. In some embodiments, each copy of the FAR1 coding sequence is overexpressed by the same strong constitutive promoter, such as those described herein. In some embodiments, each copy of FAR1 coding sequences is overexpressed by the strong constitutive $RtPLN1_{in}$ promoter (SEQ ID NO:15). In some embodiments, each copy of the FAR1 coding sequence is overexpressed by the strong constitutive RtGPD1 promoter (SEQ ID NO: 16). In some embodiments, each copy of the FAR1 coding sequence is overexpressed by the strong constitutive $RtTEF1_{in}$ promoter (SEQ ID NO: 17).

In some embodiments, multiple copies of the FAR1 gene are present in the genetically modified host cell. In some embodiments, three copies of the FAR1 gene are present in the genetically modified host cell. In some embodiments, each copy of the FAR1 gene is operatively linked to a different strong constitutive promoter, such as those described herein. In some embodiments the different promoters are selected from by the strong constitutive $RtPLN1_{in}$ promoter (SEQ ID NO:15), the strong constitutive RtGPD1 promoter (SEQ ID NO:16), or the strong constitutive $RtTEF1_{in}$ promoter (SEQ ID NO: 17).

In some embodiments, the heterologous FAR1 is derived from *Marinobacter aquaeolei*. In some embodiments, the coding sequence is codon optimized for the host fungal cell. In some embodiments, the FAR1 derived from *M. aquaeoleii* has the sequence set forth in SEQ ID NO: 14. In some embodiments, the coding sequence for the FAR1 derived from *M. aquaeolei* is set forth in SEQ ID NO:13. In some embodiments, heterologous FAR1 is a fatty acyl-CoA reductase derived from any fungal species and codon optimized for strong expression in *Rhodosporidium* species.

In some embodiments, the host cell type 1 acyl-CoA: diacylglycerol acyltransferase (Dga1) has the amino acid sequence set forth in SEQ ID NO:6. In some embodiments, Dga1 is encoded by the nucleotide sequence set forth in SEQ ID NO:5. In some embodiments, the genomic sequence for Dga1 is set forth in SEQ ID NO: 1.

In some embodiments, the host cell type 2 phospholipid: diacylglycerol acyltransferase (Lro1) has the amino acid sequence set forth in SEQ ID NO:8. In some embodiments, Lro1 is encoded by the nucleotide sequence set forth in SEQ ID NO:7 In some embodiments, the genomic sequence for Lro1 is set forth in SEQ ID NO:2.

In some embodiments, the host cell acyl-CoA:sterol acyltransferase (steryl ester synthase, Are1) has the amino acid sequence set forth in SEQ ID NO: 10. In some embodiments, Are1 is encoded by the nucleotide sequence set forth in SEQ ID NO:9. In some embodiments, the genomic sequence for Are1 is set forth in SEQ ID NO:3.

In some embodiments, the host cell type 3 soluble acyltransferase (Dga3) has the amino acid sequence set forth in SEQ ID NO: 12. In some embodiments, Dga3 is encoded by the nucleotide sequence set forth in SEQ ID NO: 11. In some embodiments, the genomic sequence for Dga3 is set forth in SEQ ID NO:4.

In some embodiments, the host cell acyl-CoA oxidase 1 (Pox1) has the amino acid sequence set forth in SEQ ID NO:61. In some embodiments, Pox1 is encoded by the nucleotide sequence set forth in SEQ ID NO:60. In some embodiments, the genomic sequence for Pox1 is set forth in SEQ ID NO:62.

In some embodiments, the expression of the host cell type 1 acyl-CoA:diacylglycerol acyltransferase (Dga1) gene or production of its protein is reduced (down-regulated) or knocked-out by anti-sense expression, co-suppression, dsRNA, ribozymes, microRNA, RNAi, genome editing, targeted promoter inactivation, site-directed mutagenesis and knock-outs. In some embodiments, the expression of the host cell type 2 phospholipid:diacylglycerol acyltransferase (Lro1) gene or production of its protein is reduced (down-regulated) or knocked-out by anti-sense expression, co-suppression, dsRNA, ribozymes, microRNA, RNAi, genome editing, targeted promoter inactivation, site-directed mutagenesis and knock-outs. In some embodiments, the expression of the host cell acyl-CoA:sterol acyltransferase (steryl ester synthase, Are1) gene or production of its protein is reduced (down-regulated) or knocked-out by anti-sense expression, co-suppression, dsRNA, ribozymes, microRNA, RNAi, genome editing, targeted promoter inactivation, site-directed mutagenesis and knock-outs. In some embodiments, the expression of the host cell type 3 soluble acyltransferase (Dga3) gene or production of its protein is reduced (down-regulated) or knocked-out by anti-sense expression, co-suppression, dsRNA, ribozymes, microRNA, RNAi, genome editing, targeted promoter inactivation, site-directed mutagenesis and knock-outs.

Such techniques are described in U.S. Pat. No. 7,312,323 and references cited therein. For example, reduction might be accomplished, for example, with transformation of a fungal host cell to comprise a promoter and other 5' and/or 3' regulatory regions described herein linked to an antisense nucleotide sequence, hairpin, RNA interfering molecule, double stranded RNA, microRNA or other nucleic acid molecule, such that tissue-preferred expression of the molecule interferes with translation of the mRNA of the native DNA sequence or otherwise inhibits expression of the native target gene in fungal cells. For further description of RNAi techniques or microRNA techniques, see, e.g., U.S. Pat. Nos. 5,034,323; 6,326,527; 6,452,067; 6,573,099; 6,753, 139; and 6,777,588. See also International Publication Nos. WO 97/01952, WO 98/36083, WO 98/53083, WO 99/32619 and WO 01/75164; and U.S. Patent Application Publication Nos. 2003/0175965, 2003/0175783, 2003/0180945, 2004/ 0214330, 2005/0244858, 2005/0277610, 2006/0130176, 2007/0265220, 2008/0313773, 2009/0094711, 2009/ 0215860, 2009/0308041, 2010/0058498 and 2011/0091975. See also International Publication No. WO 2016/159887. RNAi molecules or microRNA molecules (referred to collectively herein as RNAi molecules) can be prepared by the skilled artisan using techniques well known in the art, including techniques for the selection and testing of RNAi molecules and microRNA molecules that are useful for down regulating a target gene. See, for example, Wesley et al. (2001)], Mysara et al. (2011), and Yan et al. (2012).

Knockouts of the genes described herein are accomplished using conventional techniques well known to skilled artisan, for example, by using homologous recombination which may be enhanced by the use of a non-homologous end-joining (NHEJ) mutant (Koh et al., 2014) or by using the CRISPR-CAS9 system (Ran et al., 2013).

In some embodiments, the host cell is a cell of a *Rhodosporidium* species or a *Rhodotorula* species. In some embodiments, the host cell is a cell of a strain of *Rhodosporidium toruloides*. In some embodiments, a nucleic acid construct is stably integrated in the genome of the fungal cell. In other embodiments, the fungal cell is part of a composition also comprising a culture medium. In some embodiments, the host cell is *R. toruloides* strain ATCC 10657.

In a second aspect, the present invention provides a method for producing fatty alcohols. In some embodiments, the method comprises growing the genetically modified host cells described herein in or on a suitable medium for growth of the genetically modified host cell and for production of the desired terpene described herein. In some embodiments, the genetically modified host cells are cultured in a culture medium described herein. In some embodiments, the genetically modified host cells are grown in a conical flask containing a culture medium described herein. In some embodiments the genetically modified host cells are cultured in the conical flasks at about 20° C. to about 32° C., preferably at about 25° C. to about 30° C., more preferably at about 28° C. In some embodiments, the conical flasks are shaken at about 100 rpm to about 300 rpm, preferably at about 150 rpm to about 300 rpm, more preferably about 250 rpm to about 280 rpm, more preferable about 280 rpm. In some embodiments, the medium is GJm3 or DYM1.

In some embodiments, the GJm3 medium comprises per litre: 70 g glucose, 2.5 g yeast extract, 0.4 g $KH_2PO_4$, 1.5 g $MgSO_4.7H_2O$, and 10 ml trace element solution. In some embodiments, the trace element solution comprises per litre: 4.0 g $CaCl_2.2H_2O$, 0.55 g $FeSO_4.7H_2O$, 0.52 g citric acid.$H_2O$, 0.1 g $ZnSO_4.7H_2O$, 0.076 g $MnSO_4.H_2O$, and 0.1 ml smoked $H_2SO_4$. In some embodiments the pH of the GJm3 medium is from about 5.5 to about 6.5, preferably from about 5.8 to about 6.2, more preferably about 6.0. In some embodiments, the DYM1 medium comprises per litre: 100 g glucose, 22.5 g yeast extract, 0.75 g $K_2HPO_4$, 0.7 g $NH_4NO_3$, 0.4 g $MgSO_4.7H_2O$, and 0.4 g $CaCl_2.2H_2O$. In some embodiments the pH of the DYM1 medium is from about 4.5 to about 5.5, preferably from about 4.8 to about 5.2, more preferably about 5.0.

In some embodiments, the genetically modified host cells are grown in a bioreactor containing a culture medium described herein. In some embodiments, the culture medium is the DYM1 medium described herein. In some embodiments, the genetically modified host cells from a seed culture in YPD broth (1% yeast extract, 2% peptone, 2% glucose) are inoculated into a bioreactor at a dilution rate of about 1% to about 30%, preferably about 5% to about 20%, more preferably about 10%. In some embodiments, the fermentation medium is kept at about 20° C. to about 32° C., preferably at about 25° C. to about 30° C., more preferably at about 30° C. In some embodiments, the fermentation medium is kept at a pH of about 4.5 to about 5.5, preferably about 4.8 to about 5.2, more preferably about 5. In some embodiments, the pH is maintained by the addition of 12.5% NH$_4$OH solution. In some embodiments, the fermentation medium is kept at a pO$_2$ of about 10% to about 50%, preferably about 10% to about 40%, more preferably about 30%. In some embodiments, the pO$_2$ is sustained above 30% of air saturation by adapting the stirrer speed. In some embodiments, the bioreactor is aerated at about 2.5 L/min to about 4 L/min, preferably from about 2.8 L/min to about 3.2 L/min, more preferably about 3 L/min (1.5 vvm). In some embodiments, glucose concentration in the medium was kept at about 40 g/L to about 60 g/L by feeding glucose (about 800 g/L). In some embodiments, glucose feeding was stopped after 100 h to about 140 h, preferably about 110 h to about t130 h, more preferably about 120 h of cultivation to achieve its full consumption.

In some embodiments, fatty alcohols can be produced having from 4-6 carbons to as many as 22-26 carbons, including the commercially important lauryl (C14:0), stearyl (C18:0) and oleyl (C18:1) alcohols. In some embodiments, the amount of fatty alcohols produced in shaking flask cultures in accordance with the present invention ranges in the amount of about 1.5 g/L to about 2.5 g/L, typically about 2.0 g/L. In some embodiments, the amount of fatty alcohols produced in 2 L bioreactor cultures in accordance with the present invention ranges in the amount of about 11.0 g/L to about 13.0 g/L, typically about 12.0 g/L.

In preparing nucleic acid constructs for use in the present invention, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions may be involved.

Nucleic acids of the present invention may also be synthesized, either completely or in part, especially where it is desirable to provide fungi-preferred sequences, by methods known in the art. Thus, all or a portion of the nucleic acids of the present invention may be synthesized using codons preferred by a selected host. Species-preferred codons may be determined, for example, from the codons used most frequently in the proteins expressed in a particular host species. Other modifications of the nucleotide sequences may result in mutants having slightly altered activity.

One or more nucleic acid constructs may be introduced directly into a fungal cell using techniques such as electroporation, DNA particle bombardment. Alternatively, the nucleic acid constructs may be combined with suitable T-DNA flanking regions and introduced into an *Agrobacterium tumefaciens* host, which will deliver the gene cassette into the fungal genome. Thus, any method, which provides for effective transformation/transfection of fungi may be employed. See, for example, U.S. Pat. Nos. 7,241,937, 7,273,966 and 7,291,765 and U.S. Patent Application Publication Nos. 2007/0231905 and 2008/0010704 and references cited therein. See also, International Published Application Nos. WO 2005/103271 and WO 2008/094127 and references cited therein. See also International Publication No. WO 2016/159887.

The transformed fungi are transferred to standard growing media (e.g., solid or liquid nutrient media, grain, vermiculite, compost, peat, wood, wood sawdust, straw, etc.) and grown or cultivated in a manner known to the skilled artisan.

After the polynucleotide is stably incorporated into transformed fungi, it can be transferred to other fungi by sexual crossing. Any of a number of standard breeding techniques can be used, depending upon the species to be crossed.

It may be useful to generate a number of individual transformed fungi with any recombinant construct in order to recover fungi free from any positional effects. It may also be preferable to select fungi that contain more than one copy of the introduced polynucleotide construct such that high levels of expression of the recombinant molecule are obtained.

It may be desirable to produce fungal lines that are homozygous for a particular gene if possible in the particular species. In some species this is accomplished by the use monosporous cultures. By using these techniques, it is possible to produce a haploid line that carries the inserted gene and then to double the chromosome number either spontaneously or by the use of colchicine. This gives rise to a fungus that is homozygous for the inserted gene, which can be easily assayed for if the inserted gene carries with it a suitable selection marker gene for detection of fungi carrying that gene. Alternatively, fungi may be self-fertilized, leading to the production of a mixture of spores that consists of, in the simplest case, three types, homozygous (25%), heterozygous (50%) and null (25%) for the inserted gene. Although it is relatively easy to score null fungi from those that contain the gene, it is possible in practice to score the homozygous from heterozygous fungi by Southern blot analysis in which careful attention is paid to the loading of exactly equivalent amounts of DNA from the mixed population, and scoring heterozygotes by the intensity of the signal from a probe specific for the inserted gene. It is advisable to verify the results of the Southern blot analysis by allowing each independent transformant to self-fertilize, since additional evidence for homozygosity can be obtained by the simple fact that if the fungi was homozygous for the inserted gene, all of the subsequent fungal lines from the selfed individual will contain the gene, while if the fungus was heterozygous for the gene, the generation grown from the selfed seed will contain null fungal lines. Therefore, with simple selfing one can select homozygous fungal lines that can also be confirmed by Southern blot analysis.

Creation of homozygous parental lines makes possible the production of hybrid fungus and spores that will contain a modified protein component. Transgenic homozygous parental lines are maintained with each parent containing either the first or second recombinant DNA sequence operably linked to a promoter. Also incorporated in this scheme are the advantages of growing a hybrid crop, including the combining of more valuable traits and hybrid vigor.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which are offered by way of illustration and are not intended to limit the invention in any manner. Standard techniques well known in the art or the techniques specifically described below were utilized.

Example 1

Materials and Methods

Strains, Media, and Culture Conditions:

*R. toruloides* strain ATCC 10657 was obtained from ATCC (USA). *R. toruloides* was cultured at 28° C. in YPD broth (1% yeast extract, 2% peptone, 2% glucose, w/v) or on potato-dextrose agar (PDA). *A. tumefaciens* strain AGL2 (Cai et al., 2009) was cultured at 28° C. in either liquid or solid 2YT medium (1.6% tryptone, 1% yeast extract, 0.5% NaCl). *Escherichia coli* XL1-Blue was cultured in Luria-Bertani (LB) broth or on LB agar and used for routine DNA manipulations.

Lipid accumulation medium MinRL2 was prepared as reported previously (Liu et al., 2015). Lipid accumulation medium GJm3 was prepared as described previously (Jin et al., 2013) with some modifications. Briefly, GJm3 medium (per litre) contains 70 g glucose, 2.5 g yeast extract, 0.4 g $KH_2PO_4$, 1.5 g $MgSO_4.7H_2O$, 10 ml trace element solution, pH6.0. Trace element solution (per litre): 4.0 g $CaCl_2.2H_2O$, 0.55 g $FeSO_4.7H_2O$, 0.52 g citric acid.$H_2O$, 0.1 g $ZnSO_4.7H_2O$, 0.076 g $MnSO_4.H2O$, 0.1 ml smoked $H_2SO_4$.

Fatty alcohol production medium SC, SY, DC and DY modified from the PSC medium (Fillet et al., 2015). SC (PSC) medium contains (per litre) 100 g sucrose, 22.5 g corn steep liquid, 0.75 g $K_2HPO_4$, 0.7 g $NH_4NO_3$, 0.4 g $MgSO_4.7H_2O$, 0.4 g $CaCl_2.2H_2O$, pH5.0. SY medium is similar as SC medium except the replacement of corn steep liquid by yeast extract. DC and DY medium is similar as SC and SY medium, respectively, except the replacement of sucrose by glucose.

Bioinformatics: Putative *R. toruloides* homologues were identified through BLAST search (NCBI, USA) of the *Rhodotorula glutinis* ATCC 204091 genome database (whole-genome shotgun project PID-59971 by Mississippi State University) (Paul et al., 2014). The phylogenic tree was constructed by MEGA version 6 program (http colon slash slash www dot megasoftware dot net slash) using Neighbor-Joining algorithm and tested by Bootstrapping. The structural organization of the DGAT genes was determined after alignment of genomic DNA and cDNA sequences. Transmembrane structures were predicted using the transmembrane prediction server TMHMM-2.0 (http colon slash slash www dot cbs dot dtu dot dk slash services slash TMHMM/) with the complete protein sequences.

Plasmid Constructs:

Microorganisms and plasmids used are listed in Table 1.

TABLE 1

Microorganisms and Plasmids

| Plasmid/Strain | Plasmid/genotype | Reference |
| --- | --- | --- |
| Plasmids | | |
| pKO1 | Binary vector used for gene deletion constructs | Herein |
| pKODGA1 | Deletion of DGA1 | Herein |
| pKOLRO1 | Deletion of LRO1 | Herein |
| pKOARE1 | Deletion of ARE1 | Herein |
| pKODGA3 | Deletion of DGA3 | Herein |
| pKC2DGA1 | Overexpression of DGA1 driven under GPD1 promoter | Herein |
| pKC2LRO1 | Overexpression of LRO1 driven under GPD1 promoter | Herein |
| pKC2ARE1 | Overexpression of ARE1 driven under GPD1 promoter | Herein |
| pKC2DGA3 | Overexpression of DGA3 driven under GPD1 promoter | Herein |
| pKC2DL | Overexpression of DGA1 and LRO1 driven under GPD1 promoter | Herein |
| pGEX-6P-1 | GST-fusion protein expression system | GE Healthcare |
| pGEXDGA3 | *E. coli* expression of GST-Dga3 fusion protein | Herein |
| pKC2FAR1 | Overexpression of RtFAR1 driven under GPD1 promoter | Herein |
| pKT13FAR1 | Overexpression of RtFAR1 driven under TEF1in promoter | Herein |

TABLE 1-continued

Microorganisms and Plasmids

| Plasmid/Strain | Plasmid/genotype | Reference |
|---|---|---|
| pKP4FAR1 | Overexpression of RtFAR1 driven under PLN1in promoter | Herein |
| pKPGPTFAR1 | Overexpression of RtFAR1 (3×) driven under GPD1, TEFlin and PLN1in promoter | Herein |
| *E. coli* strains | | |
| XL1-Blue | recA1 endA1 gyrA96 thi-1 hsdR17 supE44 relA1 lac [F' proAB lacI$^q$ZΔM15 Tn10 (Tet$^r$)], plasmid cloning host | Agilent |
| BL21 (DE3) | F$^-$ ompT gal dcm Ion hsdS$_B$(r$_B^-$ m$_B^-$) λ(DE3 [ladI lacUV5-T7 gene 1 ind1 sam7 nin5]), protein expression host | Novagen |
| BL21(DE3)/pGEX DGA3 | *E. coli* engineering strain with heterologous expression of GST-Dga3 fusion protein | Herein |
| *A. tumefaciens* strain | | |
| AGL1 | T-DNA host | (Lazo et at, 1991) |
| *R. toruloides* strains | | |
| ATCC 10657 | MATA, source strain | ATCC |
| Rt1ck | MATA Δku70::hpt$^R$-ex:loxP, wild-type | (Koh et at, 2014) |
| Δdga1 | MATA Δku70Δdga1::hpt$^R$ | Herein |
| Δlo1/ | MATA Δku70Δlro1::hpt$^R$ | Herein |
| Δare1 | MATA Δku70Δare1:hpt$^R$ | Herein |
| Δdga3 | MATA Δku70Δdga3::hpt$^R$ | Herein |
| dl | MATA Δku70Δdga1Δlro1::hpt$^R$ | Herein |
| da | MATA Δku70Δdga1Δare1::hpt$^R$ | Herein |
| dla | MATA Δku70Δdga1Δlro1Δare1::hpt$^R$ | Herein |
| dlad | MATA Δku70Δdga1Δlro1Δare1Δdga3::hpt$^R$ | Herein |
| ΔdgalC | MATA Δku70Δdga1::hpt$^R$-ex Δcar2::P$_{GPD1}$-DGA1-T$_{35S}$ | Herein |
| Δlro1C | MATA Δku70Δlro1::hpt$^R$-ex Δcar2::P$_{GPD1}$-LRO1-T$_{35S}$ | Herein |
| dlad-DGA1 | MATA Δku70Δdga1Δlro1Δare1Δdga3::hpt$^R$-ex Δcar2::P$_{GPD1}$-DGA1-T$_{35S}$ | Herein |
| dlad-LRO1 | MATA Δku70Δdga1Δlro1Δare1Δdga3::hpt$^R$-ex Δcar2::P$_{GPD1}$-LRO1-T$_{35S}$ | Herein |
| dlad-ARE1 | MATA Δku70Δdga1Δlro1Δare1Δdga3::hpt$^R$-ex:loxP P$_{GPD1}$-ARE1-T$_{35S}$:: CAR2 | Herein |
| dlad-DGA3 | MATA Δku70Δdga1Δlro1Δare1Δdga3::hpt$^R$-ex Δcar2::P$_{GPD1}$-DGA3-T$_{35S}$ | Herein |
| dlad-DL | MATA Δku70Δdga1Δlro1Δare1Δdga3::hpt$^R$-ex Δcar2::P$_{GPD1}$-DGA1-T$_{35S}$-P$_{GPD1}$-LRO1-T$_{35S}$ | Herein |
| FAR1 | MATA Δku70::hpt$^R$-ex Δcar2::P$_{GPD1}$-RtFAR1-T$_{35S}$-P$_{PLN1in}$-FAR1-T$_{35S}$-P$_{TEF1in}$-FAR1-T$_{35S}$ | Herein |
| fad2FAR1 | MATA Δku70Δfad2::hpt$^R$-ex Δcar2::P$_{GPD1}$-RtFAR1-T$_{35S}$-P$_{PLN1in}$-FAR1-T$_{35S}$-P$_{TEF1in}$-FAR1-T$_{35S}$ | Herein |
| dladFAR1 | MATA Δku70Δdga1Δlro1Δare1Δdga3::hpt$^R$-ex Δcar2::P$_{GPD1}$-RtFAR1-T$_{35S}$-P$_{PLN1in}$-FAR1-T$_{35S}$-P$_{TEF1in}$-FAR1-T$_{35S}$ | Herein |
| dladpFAR1 | MATA Δku70Δdga1Δlro1Δare1Δdga3Δpox1::hpt$^R$-ex Δcar2::P$_{GPD1}$-RtFAR1-T$_{35S}$-P$_{PLN1in}$-FAR1-T$_{35S}$-P$_{TEF1in}$-FAR1-T$_{35S}$ | Herein |
| dladpfFAR1 | MATA Δku70Δdga1Δlro1Δare1Δdga3Δpox1Δfad2::hpt$^R$-ex Δcar2::P$_{GPD1}$-FAR1-T$_{35S}$-P$_{PLN1in}$-RtFAR1-T$_{35S}$-P$_{TEF1in}$-FAR1-T$_{35S}$ | Herein |

Notes:
hptR: hygromycin resistant gene cassette P$_{GPD1-3}$-HPT-3-T$_{35S}$
ex: excision of selection marker cassette hpt$^R$ Oligonucleotides used are listed in Table 2. All restriction and modification enzymes were from New England Biolabs (NEB, USA).

TABLE 2

Oligonucleotides

| Name | Sequence (5'-3') (SEQ ID NO:) | RE site* |
|---|---|---|
| Rt113 | CCGCCAATAACCTCACCTCAG (18) | |
| Rt114 | GGCGATGGGAGCGTAGAATAC (19) | |
| LRO1L-Sf | AAA*GAGCTC*ACTCACTGGCCTCCTCGTTC (20) | SacI |
| LRO1L-Br | AAA*GGATCC*ACGTTGAGAGCGGAGAGGGAA (21) | BamHI |
| LRO1R-Hf | TTT*AAGCTT*GGACCAACGACTGCAGACCAT (22) | HindIII |
| LRO1R-Str | TTT*AGGCCT*GCCCAACCCGAGAATGAGCTT (23) | StuI |
| ARE1L-Sf | AAA*GAGCTC*ATTGACCCTGCGTGTATGC (24) | SacI |

TABLE 2-continued

Oligonucleotides

| Name | Sequence (5'-3') (SEQ ID NO:) | RE site* |
|---|---|---|
| ARE1L-Br | AAAGGATCCGTCTTGAGTGCTCCGACGAAG (25) | BamHI |
| ARE1R-Hf | TCGTCACGTTCTTGTTCAGCG (26) | HindIII |
| ARE1R-Str | TTTAGGCCTCGCCTCTACCTCACTCACGT (27) | StuI |
| MFE1L-Sf | AAAGAGCTCGCGGAACAGGAGAACAAGGAG (28) | SacI |
| MFE1L-Br | AAAGGATCCGCTCACGTCAACACTCCCAAA (29) | BamHI |
| MFE1R-Hf | TTTAAGCTTAGAACCACTCGACCGTCTTCA (30) | HindIII |
| MFE1R-Str | TTTAGGCCTCTATCGACCTCTCCCAAGCC (31) | StuI |
| DGA3L-Stf | TTTAGGCCTCCAGATCAGGGTGAGTCGT (32) | StuI |
| DGA3L-Hr | TTTAAGCTTCTTGTGGTTGTGGGGCAT (33) | HindIII |
| DGA3R-Bf | AAAGGATCCTCACTGGCTGCATCTTCTCG (34) | BamHI |
| DGA3R-Sr | GTGTGCGATGACTGTGTGGT (35) | SacI |
| Rt123 | CTGTAGAGGAGCTGCAGGATCAA (36) | |
| Rt124 | CGAGCTTGATGAATCCTTTTCGT (37) | |
| LRO1f | TGCAGCTCCCTTCTTTCGCTC (38) | |
| LRO1r | ATGCTGTGCGAGACGAGAACC (39) | |
| ARE1f | CTCGCACCCACTCTTCTTCCG (40) | |
| ARE1r | TTCCGATCCGCAAACCTCGTC (41) | |
| MFE1f | AACCAGGACACGATGGGCTTG (42) | |
| MFE1r | TCCTTCTCAGTCGCGCCAATG (43) | |
| DGA3f | CATGTTCGCCGGTCTCCACTT (44) | |
| DGA3r | CCTGCTTGGCCTTCTCAACGT (45) | |
| Rt347Nf | TTTCCATGGGCCAGCAGGCGACG (46) | Exp DGA1 |
| Rt348Evr | TTTGATATCGTCCGTTGCGAGGAGGTCAG (47) | |
| Rt349Bsf | TTTTCATGAGCACAGTACGGAGGCGCA (48) | Exp LRO1 |
| Rt350Pmr | TTTGTTTAAACAGGCGTACAGGGTGGGTCAGC (49) | |
| Rt351Nf | TTTCCATGGCCTCGCTAGACCCGCCA (50) | Exp ARE1 |
| Rt352Evr | TTTGATATCTGCGCCCTGAGCTCAGTAC (51) | |
| Rt471Bsf | TTTTCATGACCGTCTCGACGAACGCTATC (52) | Exp DGA3 |
| Rt472Evr | TTTGATATCTCCATTTAATCGCGCTGGTTC (53) | |
| Rt550Gf1 | AGATTGTCGTTTCCCGCCTTCAGTTTTTTACTAGTGGACGGCTTG (54) | |
| Rt551Gr2 | GTCGCACCCCAAACGATGCTGAAGGCTCGCAAACATGCTAATTCGGGGGATCTGGATTTTAGTAC (55) | |
| Rt533F2f | GCGAGCCTTCAGCATCGTTTGGGGTGCGACCTAGTCACGCCTCTGTGACTCGGTACG (56) | |
| Rt534F2r | CAATCAAGATGTCGTTGTGCTAGTGTACGCAAACATGCTAATTCGGGGGATCTGGATTTTAGTAC (57) | |
| Rt552Tf5 | GCGTACACTAGCACAACGACATCTTGATTGCTAGTGCACGCGAAGCGGTAGAAG (58) | |
| Rt553Tr6 | CGATACTCTCAAGGTCAGCTCGAATTGTTTAAACATGCTAATTCG (59) | |

Note:
*Restriction enzyme recognition site

All gene disruption was performed by ATMT using the binary vectors where the entire coding regions were replaced by the hygromycin resistant gene expression cassette. For deletion of DGA1, a 2.8 kb 5'-phosphorylated DGA1 DNA fragment amplified using R. toruloides ATCC 10657 genomic DNA by oligos Rt113/114 was ligated to SacI (blunt-ended) and PmeI double digested pEX2 vector (Liu et al., 2011) to create the intermediate plasmid pEX2DGA1. pEX2DGA1 was double digested with SpeI (blunt-ended) and SmaI, and inserted with BamHI/HindIII-digested (blunt-ended) codon-optimized hygromycin selection cassette from pDXP795hptR ($P_{GPD1}$::hpt-3::$T_{nos}$) (Koh et al., 2014) to create the plasmid pKODGA1, where $P_{GPD1}$, hpt-3 and $T_{nos}$ represents the promoter of endogenic glyceraldehyde 3-phosphote dehydrogenase, the codon-optimized gene of hygromycin phosphotransferase and the terminator of A. tumefaciens nopaline synthase gene, respectively (Liu et al., 2013b). For deletion of LRO1, left and right homology flanking fragment (~0.9 kb each) was amplified with oligo pairs LRO1L-Sf/LRO1L-Br and LRO1R-Hf/LRO1R-Str, respectively. A four-fragment ligation was performed with SacI/PmeI-digested pEX2 vector, SacI/BamHI-digested left flanking fragment, BamHI/HindIII-digested codon-optimized hygromycin selection cassette and HindIII/StuI-digested right flanking fragment to create plasmid pKOLRO1. A similar strategy was applied to construct pKOARE1 and pKODGA3. For construction of pKOARE1, oligo pairs ARE1L-Sf/ARE1L-Br and ARE1R-Hf/ARE1R-Str and restriction enzymes SacI/BamHI and HindIII/StuI were used to amplify and digest the left and right flanking DNA fragments of ARE1 (0.9 kb each), respectively. pKODGA3 was constructed using oligo pairs DGA3L-Stf/DGA3L-Hr and DGA3R-Bf/DGA3R-Sr and restriction enzymes StuI/HindIII and BamHI/SacI.

For gene overexpressions, the entire open reading frame of DGA1, LRO1 and DGA3 was generated by reverse transcription-PCR using oligo pair Rt347Nf/Rt348Evr, Rt349Bsf/Rt350Pmr and Rt471Bsf/Rt472Evr, respectively. The 1.0 kb, 2.2 kb and 1.7 kb PCR products of DGA1, LRO1 and DGA3 were double digested with NcoI/EcoRV, BspHI/PmeI and BspHI/EcoRV, and cloned into the NcoI and EcoRV sites of pKCL2 (Liu et al., 2015) to create plasmid pKC2DGA1, pKC2LRO1 and pKC2DGA3, respectively.

For metabolic engineering of fatty alcohol prodution, the gene encoding M. aquaeolei VT8 fatty acid reductase (Maqu_2220, GenBank accession number YP_959486.1) (Hofvander et al., 2011) was codon-optimized based on the codon bias of R. toruloides and commercially synthesized (RtFAR1, Genscript, USA). The NcoI-EcoRV double digested RtFAR1 DNA fragment was firstly cloned to the same sites of vector pKCL2, pKCLT23 and pKCLP4 to create plasmid pKC2FAR1, pKCT2FAR1 and pKCP4FAR1 driven under the strong constitutive promoter of GPD1 (Liu et al., 2013b) (SEQ ID NO:16), translation elongation factor lac gene ($P_{TEF1in}$; SEQ ID NO:17) and the lipid production-correlated perilipin gene ($P_{PLN1in}$; SEQ ID NO:15), respectively. The fatty acid reductase expression cassette $P_{GPD1}$::RtFAR1::$T_{35S}$, $P_{TEF1in}$::RtFAR1::$T_{35S}$ and $P_{PLN1in}$::RtFAR1::$T_{35S}$ was amplified using the template of above plasmid and oligo pair Rt550Gf1/Rt551Gr2, Rt533F2f/Rt534F2r and Rt552Tf5/Rt553Tr6, respectively, where $T_{35S}$ represents the terminator of Cauliflower mosaic virus (CaMV) 35S gene. The final engineering plasmid pKCGPTFAR1 was created by assembly of above three RtFAR1 expression cassettes in the SpeI-PmeI-linearized vector pKCL2 by Gibson Assembly (NEBuilder kit, Bio-Rad laboraties, USA) and sequencing confirmed using BigDye Terminator chemistry (Applied Biosystem, ThermoFisher Scientific, USA).

Transformation and Fungal Colony PCR:

The binary vectors were electroporated into AGL1 and transformed to R. toruloides through Agrobacterium tumefaciens-mediated transformation (ATMT) as previously described (Liu et al., 2013b). For gene deletion analysis, positive T-DNA-tagging transformants were selected on YPD medium supplemented with 300 g/ml cefotaxime and 150 µg/ml hygromycin, and screening for candidate gene deletion mutants were initiated by fungal colony PCR (Liu et al., 2013b) and verified by Southern blot analysis. For in vivo gene expression analysis, the CAR2-locus integrated transformants were easily selected by visual screening for albino mutants on the selection agar medium as reported previously (Liu et al., 2015).

Extraction of Genomic DNA and Total RNA:

Genomic DNA and total RNA of R. toruloides were extracted as described previously (Liu et al., 2015). The concentrations of DNA or RNA samples were determined with NanoDrop® ND-1000 Spectrophotometer (Nanodrop Technologies, Wilmington, USA) and the integrity of the extracted nucleic acids were qualified by agarose gel electrophoresis.

Figure 1:
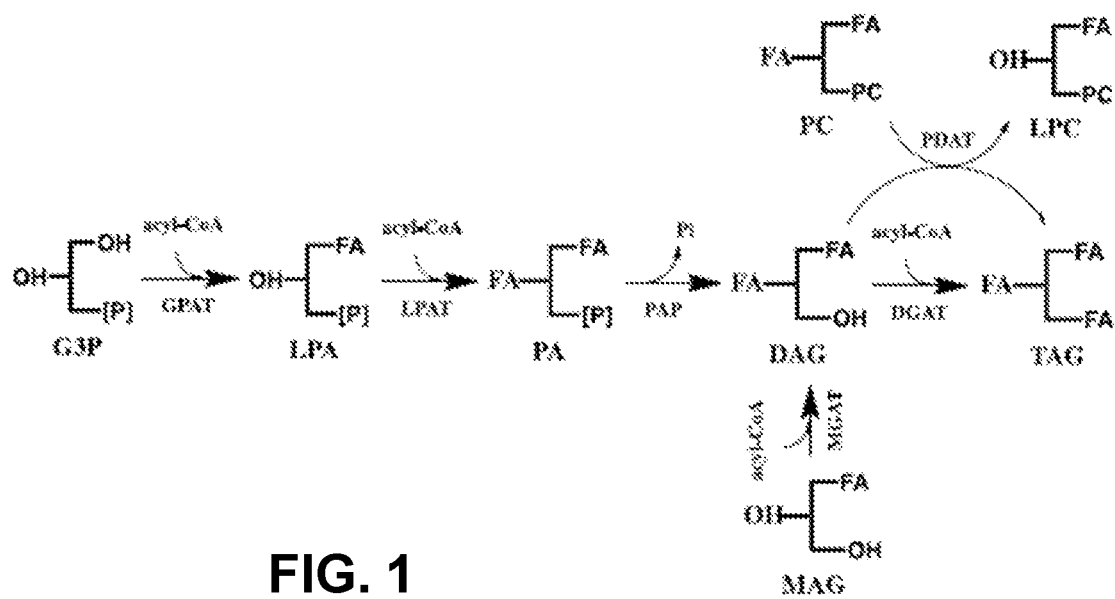
FIG. 1 shows a scheme of triacylglycerol biosynthesis pathway in fungi. Abbreviations: LPA, lysophosphatidic acid; PA, phosphatidic acid; LPC, lysophosphatidylcholine; PC, phosphatidylcholine; G3P, sn-glycerol-3-phosphate; MAG, sn-1-monoacylglycerol; DAG, sn-1,2-diacylglycerol; TAG, triacylglycerol; FA, fatty acid, LPAT, acyl-CoA:lysophosphatidic acid acyltransferase; PAP, phosphatidate phosphatase; DGAT, acyl-CoA:diacylglycerol acyltransferase; MGAT, acyl-CoA:monoacylglycerol acyltransferase; DGTA, diacylglycerol transacylase; PDAT, phospholipid:diacylglycerol acyltransferase.
Figure 2A:
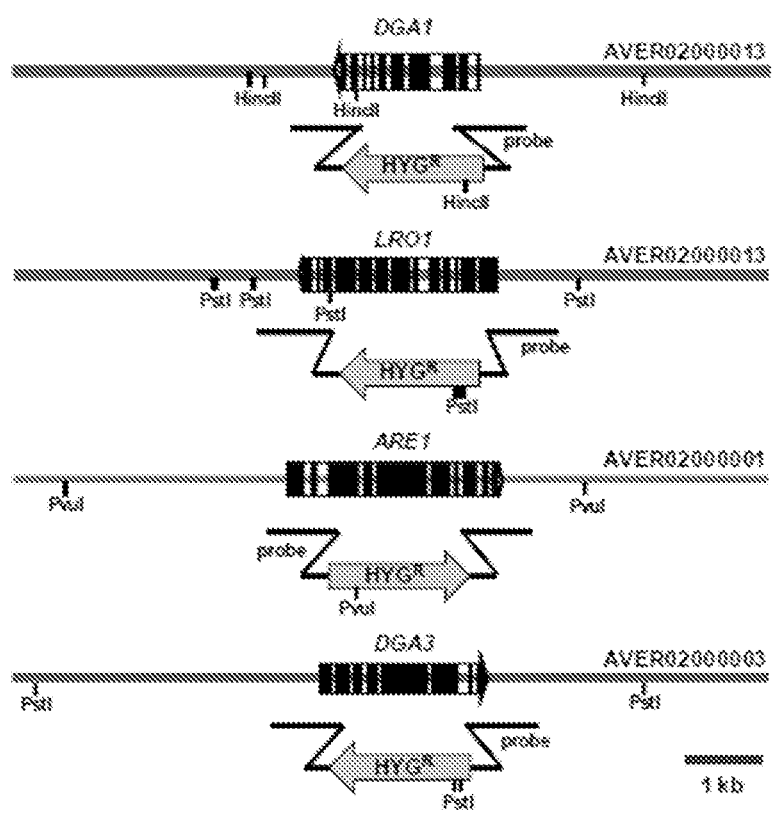
FIGS. 2A and 2B show DGAT encoding genes and deletions in *R. toruloides*.

Southern Blot Analysis:

For Southern blot analysis, genomic DNA (5 µg) was digested with appropriate restriction enzyme and separated by electrophoresis in 0.8% agarose gel. Southern hybridization was performed using DIG High Prime DNA Labeling and Detection Starter Kit according to manufacturer's instruction (Roche Diagnostics, Indiana, USA), and the DIG-labelled probe was the flanking DNA fragment as indicated in FIG. 2A.

Quantitative Reverse Transcription PCR:

To remove the trace DNA, total RNA was treated with DNase I (Roche Diagnostics) followed by precipitation with ethanol. cDNA was synthesized using the iScript™ Reverse Transcription Supermix for RT (Bio-Rad, USA) and real-time PCR was conducted in ABI PRISM 7900HT Sequence Detection System (Life Technologies, USA) using the ABI SYBR® Select Master Mix (Life Technologies, USA). Real-time PCR conditions were as follows: an initial 50° C. for 2 min and 95° C. denaturation step for 10 min followed by 40 cycles of denaturation at 95° C. for 15 s, annealing at 60° C. for 1 min. Triplicates were used for all qRT-PCR analyses. The data was acquired using the software SDS 2.4 (Applied Biosystems, Life Technologies, USA) and relative gene expression was calculated by RQ Manager software (version 1.2.1, Applied Biosystems) using the reference gene ACT1 (GenBank accession number KR183696) and $2^{-\Delta\Delta Ct}$ method.

Lipid Extraction:

Total crude lipid was extracted by acid-heating procedure as previously reported (Elsey et al., 2007) with some modifications. After calculating dry cell biomass, 10 mg cells were mixed with 500 µl 4 M HCl and lysed in a boiled water batch for 15 min. After frozen at −20° C. for 1 h, the cell lyses were mixed with 0.2 mg pentadecanoic acid (C15:0, internal standard for the subsequent GC analysis) and 1.0 ml of lipid extraction solvent (chloroform:methanol=2:1). The chloroform phase was removed to a new tube and crude lipid was gravimetrically quantified as the total lipid amounts after vacuum dry (Concentrator, Eppendorf, USA).

Thin Layer Chromatography:

The lipid composition of extracted lipids were separated and analyzed by TLC as reported previously by (Athenstaedt, 2011) with some modifications. Aliquots of the crude lipids (5 µL) were applied to Silica Gel 60 plates (Merck, Germany) by the CAMAG 5 Nano-Applicator (CAMAG, Muttenz, Switzerland) and chromatograms were developed in a two-step system, petrium ester/ethyl acetate/acetic acid (25:25:1, v/v/v) and petrium ester/ethyl acetate (49:1, v/v), and visualized using $MnCl_2$-methanol-sulfuric acid buffer (Athenstaedt, 2011). A mixture of oleic acid, sterol, tri-, di- and mono-acylglycerol from Sigma-Aldrich including oleic acid (Sigma catalog No.), sterol ( ), glyceryl trioleate (92860), 1,2-dioleoyl-sn-glycerol (D0138), glyceryl 1,3-distearate (D8269) and 1-oleoyl-rac-glycerol (M7765), was used as the lipid standard. The separated lipid classes were visualized by dipping the plates into solution into a solution of 10% (w/v) copper (II)-sulphate-pentahydrate in 8% (v/v) phosphoric acid, drying at 100° C. and heating at 170° C. until ashed spots appeared. Photographs were taken using a CAMAG TLC Scanner. The amounts of different lipid components were measured on the basis of the band intensity through a web-based TLC analysis software JustQuantify (version 2.0, Sweday, Södra Sandby, Sweden).

Lipid Staining and Fluorescent Microscopy:

The BODIPY (4,4-difluro-1,3,5,7-tetramethyl-4-bora-3a,4adiaza-s-indacene) was used for staining lipid bodies according to the method adapted from Nile Red staining as reported by Yang et al. (Yang et al., 2012) with some modifications. Briefly, BODIPY (Life Technologies, USA) was dissolved in DMSO to a final concentration of 0.1 mg/ml. A 200 µl aliquot of culture was washed twice with PBS and resuspended in 1 ml PBS supplemented with 6 µl 0.1 mg/ml BODIPY and stained in the dark for 10 min before visualization. Colonies were observed using a Nikon SMZ 800 fluorescence microscope equipped with Plan Apo WD70 objective (Nikon, Tokyo, Japan) and a GFP-L filter (GFP Band pass, Ex 480/40 DM 505 BA 510). Images were acquired with a Nikon DS-5M camera.

Cell Biomass Determination:

Cell biomass (dry cell weight) was determined by drying the water-washed cell pellet in a 70° C. oven until constant weight was reached.

Quantification of Residual Glucose:

Residual glucose in cell culture was quantified by HPLC (Shimadzu, Japan). Fermentation samples were filtered through a 0.2 µm membrane and run through a 300×7.0 mm Aminex HPX-87H column (Bio-Rad, USA) at a constant flow rate of 0.7 ml $min^{-1}$ using 5 mM sulfuric acid as the mobile phase. The column was maintained at 50° C. and glucose was detected with a Refractive Index Detector (Shimadzu, Japan). Concentration of residual glucose in the cell culture was determined using calibration curve built with the standard glucose aqueous solution.

Fatty Acid Composition Analysis:

Gas-lipid chromatography-Mass spectrometry (GCMS) was used for fatty acid profiling. Preparation of fatty acid methyl esters (FAMEs) and GCMS analyses were performed as described previously (Voelker and Davies, 1994) with some modifications. Lipids were dissolved in 300 µl petroleum ether-benzene (1:1, v/v), mixed with 0.4 M KOH in methanol, and keep room temperature for 2 hr. FAMEs were extracted after addition of 1 ml of water. 1 µl of FAMEs after 10-fold dilution in methanol was injected to a HP-88 fused silica capillary column (30-m length, 0.25-µm diameter, and 0.25-mm film thickness, Agilent J&W Scientific, Folsom, Calif., USA) and separated in a GCMS (QP2010, SHIMIDZU, Japan). The running conditions were typically 42.3 ml/min nitrogen flow, 150° C. for starting temperature (3 min), a 15-min ramp to 240° C., and holding at 240° C. for 7 min. The mass spectrometry peaks were identified by searching against Shimadzu NIST08 compound library and quantified as percentages of total fatty acids (% TFA).

Fatty Alcohol Production:

Lipid accumulation medium GJm3 was firstly used for fatty alcohol production unless indicated otherwise. Medium DYM1 was finally optimized for the production of fatty alcohol. Flask production was performed in 250 mL-flasks containing 50 mL of medium and cultured at 28° C., 280 rpm for 5 days. Fed-batch fermentation was performed in a Biostat® B fermentor (Sartorius AG, Göttingen, Germany) equipped with a 2-litre jacketed vessel. DYM1 medium (1.0 L) was added to the reactor and sterilized in autoclave (121° C., 20 min). Once the medium was cooled down culture conditions were set to 30° C., pH 5 and 3 L/min aeration (1.5 vvm). The reactor was inoculated with 100 mL from a seed culture in YPD broth. The pH was maintained by adding 12.5% $NH_4OH$ solution and $pO_2$ was sustained above 30% of air saturation by adapting the stirrer speed. Sugar concentration in the broth was kept at 40 to 60 g/L by feeding glucose (800 g/L). After 120 h of cultivation glucose feeding was stopped to achieve its full consumption.

Extraction, Identification and Quantification of Fatty Alcohol:

Fatty alcohol was extracted and identified as described previously (Fillet et al., 2015) with some modifications. Briefly, cell culture (1 ml) was transferred in an Ependorf centrifuge tube and centrifuged at 10,000 rpm for 3 min to separate the supernatant broth and cell pellet. The supernatant was mixed with 20 mg heptadecanal as the internal standard (ISTD) and extracted with 500 µL of ethyl acetate for three times. The organic phases were combined and dried with $Na_2SO_4$ power to obtain the extracellular fatty alcohols. To extract intracellular fatty alcohols, cell pellet was washed with PBS buffer and resuspended with above lipid extraction solvent (chloroform:methanol=2:1) and 20 mg heptadecanal (ISTD). Cellular lysis was achieved with the addition of 2 volume of glass beads (0.4 mm in diameter, Sigma-Aldrich) followed by twice bead beating (40 s/round, FastPrep-24™ 5G, MP Biochemicals, Eindhoven, Netherlands). The organic phase was extracted, dried with $Na_2SO_4$ power and regarded as the intracellular fatty alcohols.

Fatty alcohols were qualified and quantified using above GCMS system (QP2010, SHIMIDZU, Japan) equipped with the DB-5HT capillary column (30-m length, 0.25-µm diameter, 0.1-mm film thickness, Agilent J&W Scientific, Folsom, Calif., USA). The running conditions were 42.3 ml/min nitrogen flow, 150° C. for starting temperature (5 min), a 20-min ramp to 350° C., and holding at 350° C. for 10 min. Mass spectrometer were set to solvent delay (5 min), electron impact ionization (70 eV) and dwell time (100 ms). Chromatograms were registered by SCAN mode (mass range 50-500 m/z). The mass spectrometry peaks were identified by searching against Shimadzu NIST08 compound library and quantified by the internal standard (hexadecanol, C17-OH).

Microscopy:

A Nikon Eclipse 80i microscope equipped with a CFI Plan Apochromat objective lens (Nikon, Japan) was used for fluorescence and differential interference contrast (DIC) images of yeast cells, and images were acquired with a DS camera and ACT-2U software (Nikon, Japan). The BODIPY (4,4-difluro-1,3,5,7-tetramethyl-4-bora-3a,4adiaza-s-indacene) was used for staining lipid bodies according to the method adapted from Nile Red staining as reported by Yang et al. (Yang et al., 2012) with some modifications. Briefly, BODIPY (Life Technologies, USA) was dissolved in DMSO to a final concentration of 0.1 mg/ml. A 200 l aliquot of culture was washed twice with PBS and resuspended in 1 ml PBS supplemented with 6 μl 0.1 mg/ml BODIPY and stained in the dark for 10 min before visualization. A fluorescein filter under emission and excitation filter of 488 and 509 nm, was used to observe the fluorescence of yeast cells stained by BODIPY.

For electron microscopy, preparations were fixed with 1% glutaraldehyde and 1% OsO4 in 0.1 M Phosphate buffer (pH7.2). Fixed preparations were dehydrated through a graded ethanol series and embedded in Epon 812 resin. Sections were sequentially stained with 4% uranyl acetate and 0.4% lead citrate and viewed in a transmission electron microscopy (TEM, JEM-2010, JEOL, Japan)

Sequences:

The genomic nucleotide sequences of DGA1, LRO1, ARE1 and DGA3, are set forth in SEQ ID NO:1, SEQ ID NO:2, SEQ ID NO:3 and SEQ ID NO:4, respectively. The coding nucleotide sequences of DGA1, LRO1, ARE1, DGA3 and RtFAR1 are set forth in SEQ ID NO:5, SEQ ID NO:7, SEQ ID NO:9, SEQ ID NO:11 and SEQ ID NO:13, respectively. The amino acid sequences of DGA1, LRO1, ARE1, DGA3 and RtFAR1 are set forth in SEQ ID NO:6, SEQ ID NO:8, SEQ ID NO: 10, SEQ ID NO: 12 and SEQ ID NO: 14, respectively.

Example 2

Diacylglycerol Acyltransferases in R. toruloides

In oleaginous yeasts, diacylglycerol acyltransferases catalyse the last and committed step in lipid biosynthesis in R. toruloides, and are essential for further engineering process. To uncover the enzymes involved in this step in R. toruloides, homologous searches (tBLASTn, NCBI) were performed using DGATs from S. cerevisiae and Yarrowia lipolytica as the queries and the genome sequence of Rhodotorula glutinis ATCC 204091 (Paul et al., 2014) as the target. A unique R. toruloides ortholog of acyl-CoA-dependent diacylglycerol acyltransferase (EC 2.3.1.20) was found sharing 40% and 51% identity to S. cerevisiae Dga1p (GenBank accession number NP_014888.1) (Sorger and Daum, 2002) or Yarrowia lipolytica Dga1p (CAG80304.1) (Athenstaedt, 2011), respectively. The putative DGA1 coding sequence (CDS) spans 1,855 nt in the scaffold No. 13 (AEVR02000013) of genome. Transcriptome analyses revealed a transcript of 1,257-nt mRNA including a 33-nt 5'UTR and 177-nt 3'UTR (untranslated region) as identified by (data not shown). DGA1 gene is composed of 11 exons separated by 10 introns, encoding a 348-aa protein showing high homologous to other diacylglycerol O-acyltransferases with the signature DGAT motif (pfam03982), and the highest identity to the brown mold Wallemia sebi DGAT (XP_006957543.1, 66% identity in protein sequence).

TABLE 3

Gene Annotations

| Gene | Scaffold No. | CDS Length (nt) | Transcript length (nt) | 5'UTR (nt) | 3'UTR (nt) | Exon number | Protein (aa) |
|---|---|---|---|---|---|---|---|
| DGA1 | 13 | 1,855 | 1,257 | 33[a] | 177[a] | 11 | 348 |
| LRO1 | 15 | 3,024 | 2,336 | 53[a] | 72[a] | 15 | 736 |
| ARE1 | 1 | 2,788 | 2150 | 6[a] | 110[a] | 10 | 678 |
| DGA3 | 3 | 2,250 | 1,929 | 110 | 151[a] | 9 | 555 |
| RtFAR1 | —[b] | 1,549 | 1,549 | —[b] | —[b] | 1 | 513 |

[a]Transcriptomics data
[b]not available according to the synthesized gene

Phospholipid:diacylglycerol acyltransferase (EC 2.3.1.158) from either S. cerevisiae (Sc Lro1p, NP_014405.1) (Oelkers et al., 2000) or Yarrowia lipolytica (Y1 Lro1p, XP_504038.1) (Athenstaedt, 2011) have the same ortholog in R. toruloides that is also localized on scaffold #13, closely adjacent (~32.7 kb) to the putative DGA1 gene. The putative LRO1 spans 3,024 nt in the genome, transcripting a 2,336-nt mRNA including a 53-nt 5'UTR and 72-nt 3'UTR (transcriptome analysis). LRO1 gene is composed of 15 exons separated by 14 introns. LRO1 encodes a 736-aa protein showing highly homologous to other LCAT motif (pfam02450)-containing phosphatidylcholine-sterol O-acyltransferases with the highest identity to U. maydis Um00322 (XP_756469.1, 54% identity).

S. cerevisiae acyl-CoA:sterol acyltransferase (EC 2.3.1.26, Are1p and Are2p, YCR048W and YNR019W, GenBank acc. no. NP_009978.1 and NP_014416.1, respectively) have a single ortholog in R. toruloides (EGU12278.1, ARE1) localized on the scaffold No. 1. R. toruloides putative ARE1 CDS spans 2,788 nt in the genome, transcripting a 2,150-nt mRNA including a 6-nt 5'UTR and 110-nt 3'UTR (transcriptome analysis). ARE1 gene is composed of 10 exons that are separated by 9 introns, and the encoding 678-aa protein (Are1) has a signature MBOAT motif (membrane-bound O-acyltransferase family, pfam03062) and exhibits highly homologous to sterol O-acyltransferase from other Pucciniomycotina species, in which the highest identity is that from R. toruloides strain CECT 1137 and NP11 (BAN63763.1 and EMS22447.1, 96% and 95% identity, respectively).

In R. toruloides, a soluble DGAT located in the 10 S cytosolic TAG biosynthetic complex was found and functionally identified recently (Rani et al., 2013). However, only a partial sequence released (ABC41546.1, 221 aa in length) with truncation in its N-terminus. Here, the full length of soluble DGAT gene (termed as DGA3) was identified through homologous searches (BLASTn, NCBI). DGA3 spans 2,250 nt in the genome sequencing scaffold No. 3, transcripting a 1,929-nt mRNA that contains a 110-nt 5'UTR (RACE analysis) and 151-nt 3'UTR (transcriptome analysis). DGA3 gene is composed of 9 exons that are separated by 8 introns, and the encoding 555-aa protein (Dga3) exhibiting strongly homologous to aldehyde dehydrogenase family members (pfam00171) among which it shows the highest identity to R. toruloides NP11 (EMS23644.1, 98%). The reported partial protein sequence (ABC41546.1) is located in the C-terminus of Dga3, ranging from 335 aa to 555 aa. Five-aa differences between the partial sequence from R. glutinis MTCC 1151 (Gangar et al., 2001; Rani et al., 2013) and the full sequence from R. toruloides, where $Q_{335}$, $K_{336}$, $C_{337}$, $Y_{448}$ and $F_{453}$ in R. toruloides Dga3 as compared to $A_1$, $R_2$, $G_3$, $F_{114}$ and $Y_{119}$ in the partial sequence of Dga3 from R. glutinis MTCC 1151, respectively.

Figure 3A:
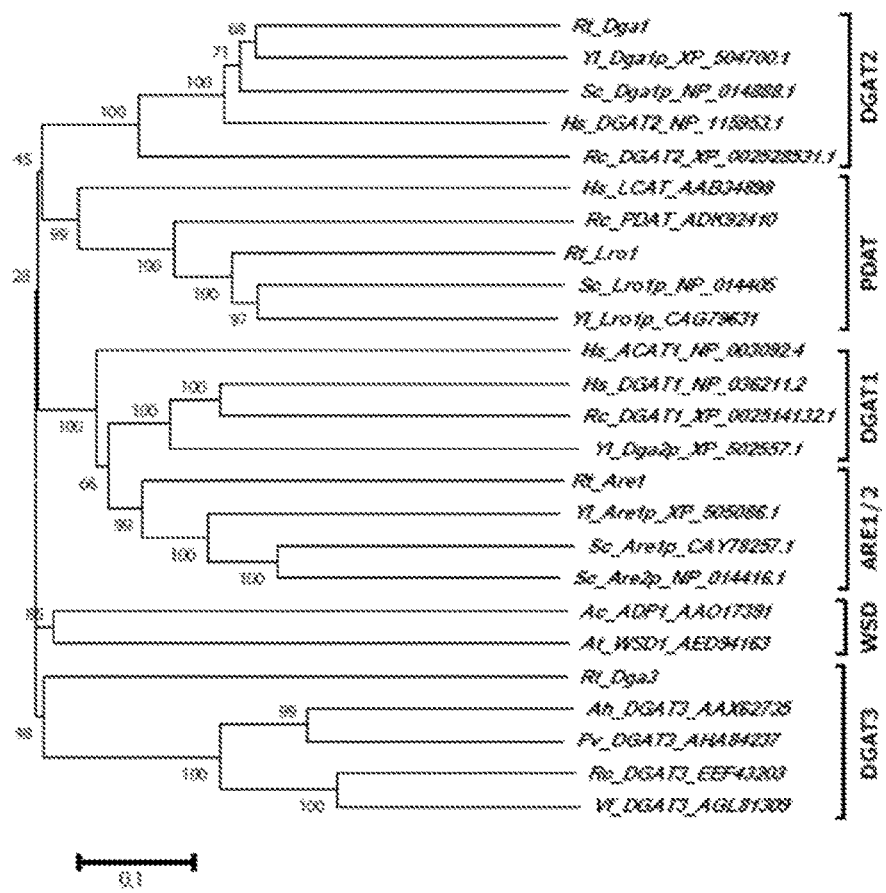
FIGS. 3A and 3B show a bioinformatic characterization of DGATs in *R. toruloides*.

A phylogenic tree of DGATs from various species was generated (FIG. 3A). The dendrogram has six main branches such as DGAT1, DGAT2, DGAT3, PDAT ARE1/2 and WSD, where Rt Dga1, Lro1 and Dga3 are clearly clustered into DGAT2, PDAT and DGAT3 group, respectively. R. toruloides genome sequence does not have any orthologs of Y. lipolytica Y1Dga2 or any other DGAT1 family members that was essential in TAG biosynthesis (Beopoulos et al., 2012) (FIG. 3A). Surprisingly, Rt Are1 shows weak homology to Y1 Dga2p and was clustered into the DGAT1 group rather than the Are1/2 group (FIG. 3A). Hence, it suggests the possible DGAT1 activity of Are1.

Figure 3B:
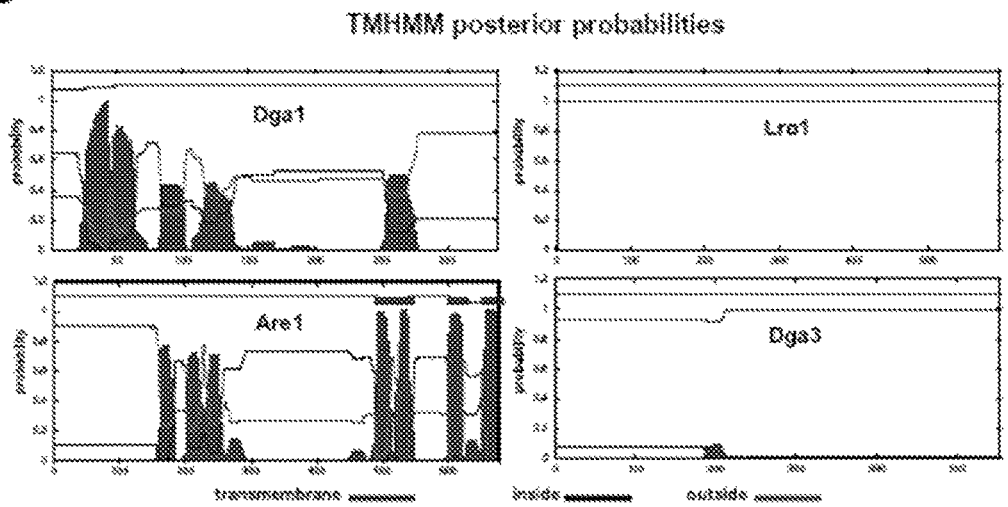

To further identify the DGATs in *R. toruloides*, the transmembrane structures were predicted. Obviously, Lro1 and Dga3 are soluble proteins, while Dga1 and Are1 are both transmembrane proteins with multiple transmembrane regions (FIG. 3B). Dga1 has two highly probable transmembrane regions, which agrees well with DGAT2 from other species (Turchetto-Zolet et al., 2011). Are1 has 7 highly probable transmembrane regions, exhibiting a conserved distribution on the protein chain as its ortholog in *S. cerevisiae* other than DGAT1 from other species (Turchetto-Zolet et al., 2011), which was further demonstrated as an acyl-CoA dependent steryl acyltransferase.

Example 3

Transcriptional Regulation of DGATs During Lipid Accumulation

Figure 4:
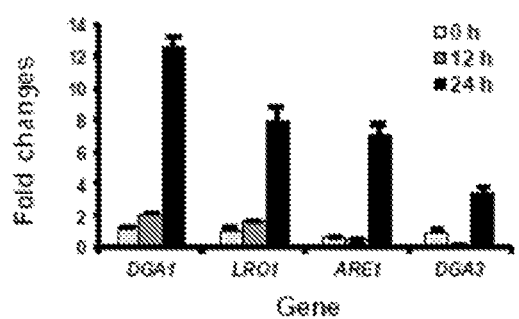
FIG. 4 shows the fold change in expression level of genes involved in lipid biosynthesis pathway between growth and lipid-inducing medium at different time points. *R. toruloides* Cells were cultured in YPD till exponential phase (OD~10, time-point 0 h) and cells were pelleted, water-washed and resuspended to YNBD (YNB w/o aa or ammonium sulfate plus 50 g/L glucose) for 24 h. Total RNAs at 0, 12 and 24 h were extracted, treated with DNaseI and cDNAs were synthesized as the template.

To investigate the transcriptional regulation of different DGATs in *R. toruloides* during lipid accumulation, nitrogen sources were depleted in the media and mRNA levels were quantified using qPCR analysis. Results showed that all DGAT mRNAs were significantly increased after 24 h starvation in nitrogen level (FIG. 4). Induction of DGA1 and LRO1 occurred after 12 h nitrogen starvation, while decreases in mRNA levels could be observed in ARE1 and DGA3 (FIG. 4). These suggest the transcriptional up-regulation of all DGAT genes during lipid accumulation.

Example 4

Lack of DGATs Lead to Serious Lipid Production Defects in *R. toruloides*

Figure 2B:
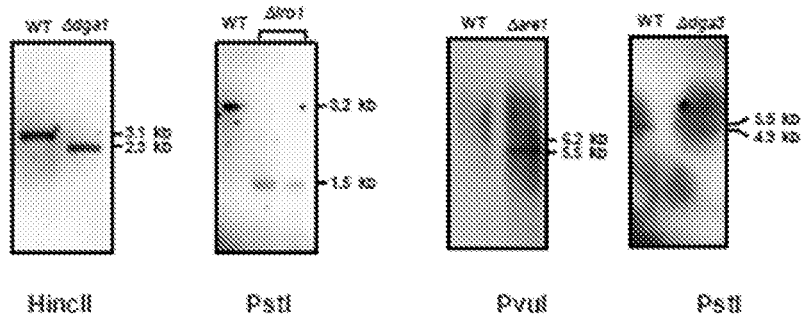
Figure 5A:
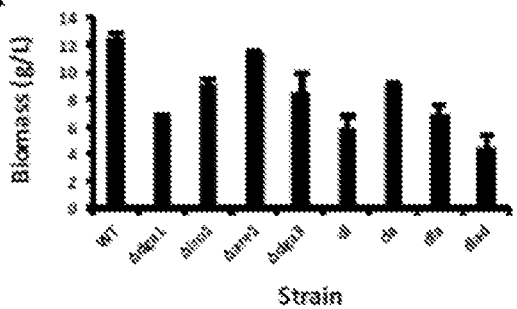
FIGS. 5A-5C show lipid profiles of DGAT mutants.
Figure 5B:
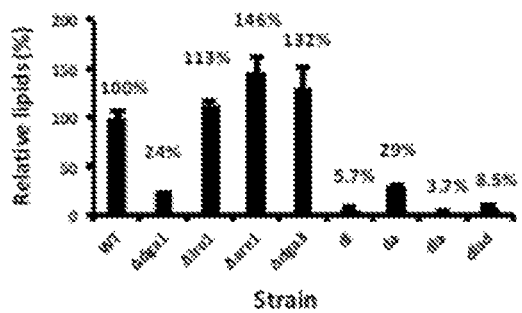

To further functionally identify the effects of *R. toruloides* acyltransferases on lipid accumulation and lipid storage, single gene deletion mutants (Δdga1, Δlro1, Δare1 and Δdga3) were generated through homologous recombination (FIG. 2A) and confirmed by Southern blot analyses (FIG. 2B). Lack of DGA1 or LRO1 led to serious cell growth defects (FIG. 5A). Lack of DGA1 resulted in dramatic decreases in lipid production by only 24% yields (FIG. 5B). However, lack of LRO1, ARE1 or DGA3 could improve lipid yields by 113%, 146% and 132%, respectively (FIG. 5B). Stacking deletions of DGA1 and LRO1 in the double gene deletion mutant Δdga1Δlro1 (dl) resulted in 5.7% lipid yields as compared to WT strain. It was surprised to see the increasing lipid yields when deletion of ARE1 in the background of Δdga1 (another double gene deletion mutant Δdga1Δare1, da) from 24% to 29% of the yields in WT (FIG. 5B). However, deletion of ARE1 in the background of dl (the triple gene deletion mutant Δdga1Δlro1Δare1, dla) could further decrease the lipid yields to only 3.7% left (FIG. 5B). Furthermore, deletion of DGA3 in the background of dla (quadruple gene deletion mutant Δdga1Δlro1Δare1Δdga3, dlad) alternately increased lipid yields from 3.7% to 8.5% (FIG. 5B). Taken together, these suggest that the three DGATs such as Dga1, Lro1 and Are1, would be essential for lipid accumulation in *R. toruloides*, while Dga3 is functionally unidentified.

Figure 5C:
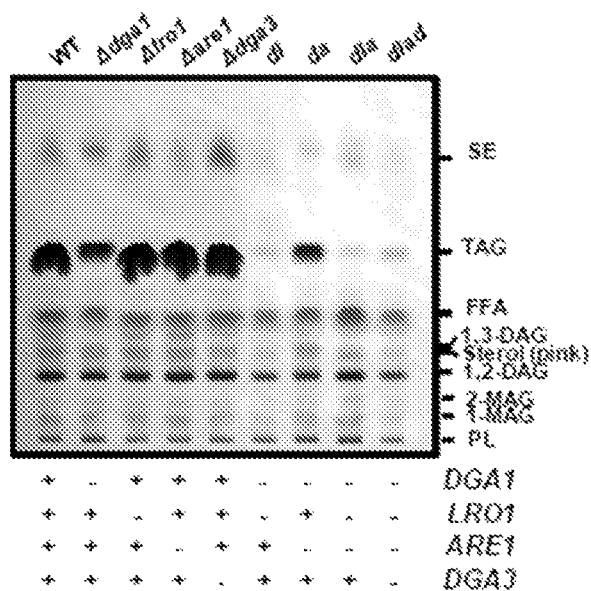
Figure 6:
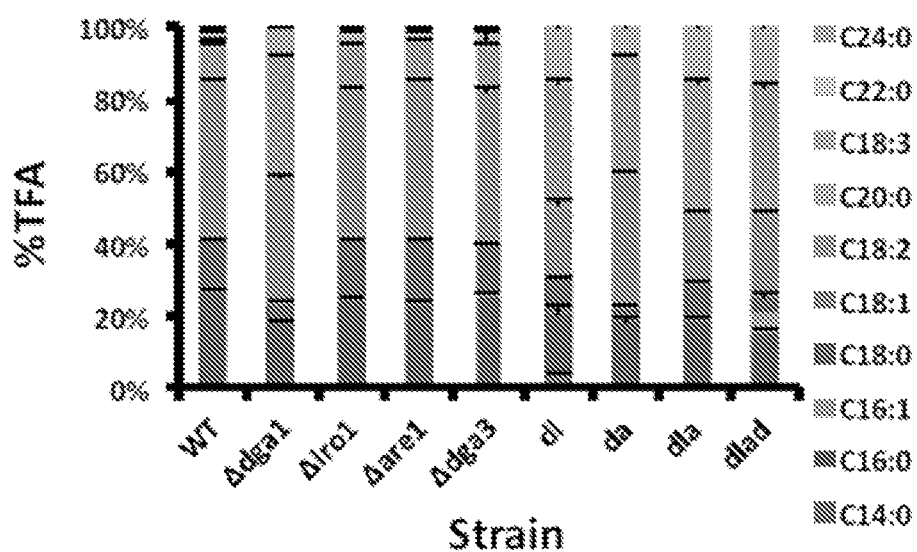
FIG. 6 shows lipid profiling of DGAT mutants through thin-layer chromatography. Cells were cultured in GJ2013 medium for 5 days with rotary shaking. The loading amount of lipids for TLC separation is 100 μg. All tests were performed by biological triplicates. Abbreviation of DGAT mutants is as in FIGS. 5A-5C. Systematic names of fatty acids: C14:0—Myristic acid; C16:0—Palmitic acid; C16:1—Palmitoleic acid; C18:0—Stearic acid; C18:1—Oleic acid; C18:2—Linoleic acid; C18:3—α-Linolenic acid; C20:0—Arachidic acid; C22:0—Behenic acid; C24:0—Lignoceric acid.

To investigate the effects of different DGATs on lipid components, especially triacylglycerol (TAG) and steryl ester (SE), lipids were separated and quantified by TLC analysis. When comparing the four DGAT mutants, only Δdga1 caused severe decrease (57.83%, Table 3) in triacylglycerol (TAG) yields (FIG. 5C), while other DGAT mutants showed 15~18% increase as compared to WT (FIG. 5C, Table 3), indicating an important role of Dga1 in TAG biosynthesis. As well agreement with above results, further stacking deletion of LRO1 and ARE1 in the double and triple gene deletion mutant, dl and dla, respectively, resulted in a gradual decrease in TAG level (FIG. 5C, Table 3). However, deletion of ARE1 in dga1 null mutant (dl) showed little effects on TAG levels as compared to Δdga1 (57.8% to 52.1%, FIG. 5C and Table 3), indicating little effects of Are1 on TAG production. As agreement with the total lipid production results, further deletion of DGA3 resulted in the increase in TAG level and absolute elimination in steryl ester level (FIG. 5C). Hence, the triple deletion mutant (dla) could produce the lowest levels of TAG and the highest levels of free fatty acids among all strains tested (FIG. 5C). The fatty acid profiles in Dgat mutants are shown in FIG. 6.

DGA1 showed little effects on steryl ester (SE) production. Lack of ARE1 resulted in an obvious decrease (61%) in steryl ester level (FIG. 5C). However, lack of LRO1 and DGA3 could significantly enhance the yields of steryl ester by 1.5 and 2 fold, respectively (FIG. 5C, Table 3). Taken together, these suggest a direct role of Are1, indirect role of Lro1 and Dga3, while no obvious role of Dga1 in the biosynthesis of SE.

Example 5

Lack of DGATs Affect the Formation of Lipid Bodies

Figure 7:
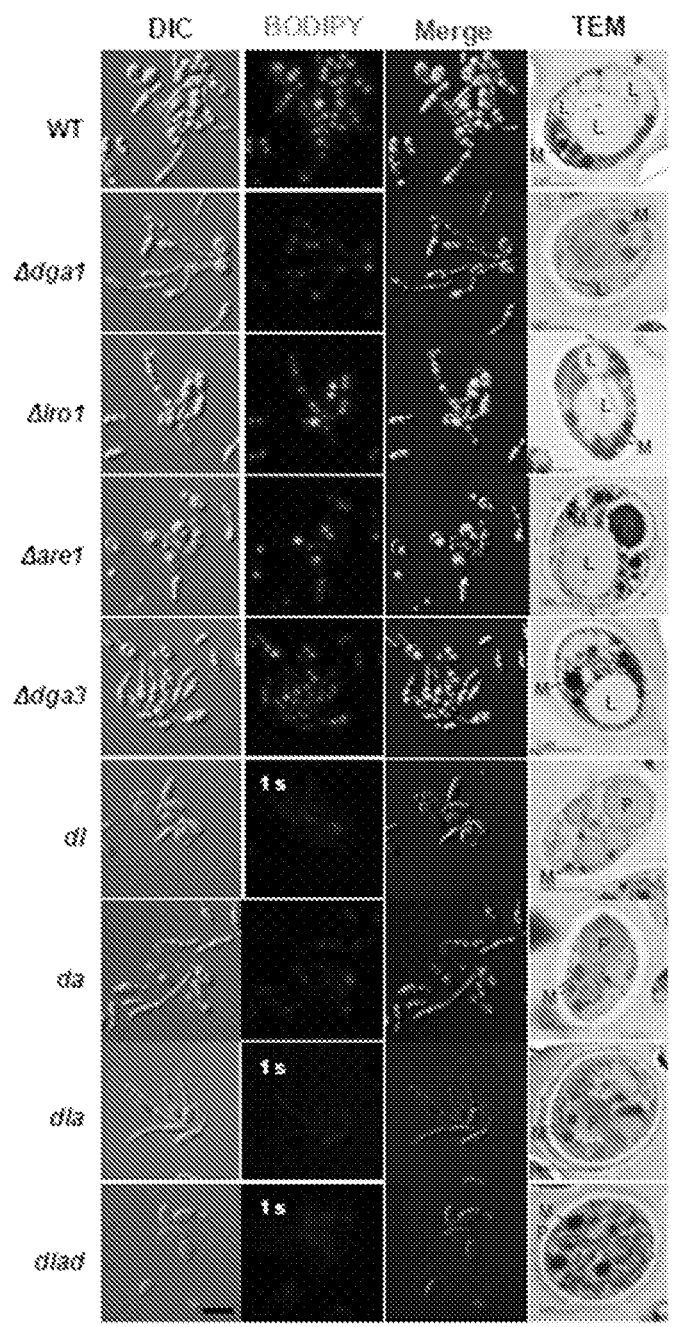
FIG. 7 shows the formation of lipid bodies in different DGAT mutants. All cells cultured in MinRL3 medium for 5 days was used for the microscopic observation. The exposure time for DIC and BODIPY staining fluorescent microscopy was 1/15 s and 1/4 s, respectively, except the observation of some strains under the exposure time of 1 s as shown in the figures. Bar represents 10 μm. Abbreviations: DIC—differential interference contrast microscopy; BODIPY— fluorescent microscopy with excitation and emission wavelength of 488 and 509 nm, respectively (eGFP channel); TEM—transmission electron microscopy. In TEM figures, L—lipid body; M—mitochondria; P—peroxisome.

Lipid body formation is essential for the biosynthesis of intracellular lipids. BODIPY, a highly lipophilic, electrically neutral bright green fluorescent dye, is used as an alternative to stain lipid bodies (Szymanski et al., 2007). High molar extinction coefficient, high oil/water partition coefficient, sharp emission bands, exceptional photo-chemical stability by maintaining fluorescence efficacy through high resistance to photo-bleaching, are among many other advantages of using BODIPY as a lipid stain (Govender et al., 2012). Here, the BODIPY staining coupled with fluorescent microscopy and TEM was used for the identification of lipid bodies. In well agreement with above results, lack of DGA1 seriously reduced both the number and size of lipid bodies, where little differences could be observed if lacks of the other three single genes (FIG. 7). Formation of lipid bodies was gradually decreased in the double mutant (da and dl) and triple mutant (dla), and few lipid bodies could be observed in either triple mutant (dla) or quadruple mutant (dlad) (FIG. 7). TEM showed the similar results as the fluorescent microscopic observation by BODIPY-staining (FIG. 7). Furthermore, enlarged and more peroxisomes could be observed during the process of multiple gene deletions (FIG. 7). Together of the studies of lipid production, lipid profiles and lipid body formations, it suggests the essential and different roles of the four DGATs in *R. toruloides*.

Example 6

Dga1 and Lro1 are Two Main Acyltransferases for the Biosynthesis of TAG

Bioinformatical analysis revealed that Dga1 and Lro1 would be the two main DGATs in *R. toruloides* (FIG. 3A), the terminal and only committed step in triacylglycerol biosynthesis. The essential effects of Dga1 and Lro1 on TAG biosynthesis were investigated by overexpression of their encoding genes. DGA1 and LRO1 were both driven under the strong and constitutive promoter of GPD1 (Liu et al., 2013b). As compared to WT, although the transcriptional up-regulation of either gene could not fully but partially complement the defects of lipid production in the quadruple mutant dlad (FIG. 8A). Due to the inverse effects of LRO1 on lipid production as compared to DGA1 (FIG. 5B), it is not surprised to observe that overexpression of LRO1 in its null mutant (Δlro1) affected little in lipid yields (data not shown). Furthermore, constitutive expression of DGA1 in its null mutant (Δdga1) could lead to an obvious improvement in either TAG or steryl ester levels (FIG. 8B), indicating the pivotal but not enough role of the sole DGA1 gene in the biosynthesis of lipids, and the complex role of DGA1 transcript levels on lipid production because of its driven by the GPD1 promoter. A stacking overexpression of both genes could restore 90% lipid yields in the quadruple mutant dlad (FIG. 8C), suggesting the key roles of Dga1 and Lro1 in lipid biosynthesis in R. toruloides.

Example 7

Dga3 is a Bifunctional Enzyme

Previous studies revealed that Rhodotorula glutinis Dga3 belonged to the soluble DGAT3 class of acyl-CoA-dependent diacylglycerol acyltransferase, heterologous expression of which could rescue the lipid production and growth defects of S. cerevisiae lipid-deficient quadruple mutant H1246 in oleate-containing medium in (Rani et al., 2013; Raychaudhuri et al., 2003). To our surprise, lack of Dga3 affected little on either TAG production or lipid body formation in R. toruloides (FIGS. 5B, 5C and 7, Table 3), indicating the hidden role of Dga3 on lipid biosynthesis by the existence of the other three acyltransferases. To demonstrate this hypothesis, we introduced a constitutive expressed DGA3 back into the CAR2-locus in the quadruple mutant dlad and determine its role in lipid production. BODIPY staining revealed that overexpression of DGA3 could partially restore the formation of lipid bodies in the acyltransferase-disrupted mutant (FIG. 9A). Lipid profiling and quantification confirmed the TAG production were improved by the existence of Dga3 (data not shown). Hence, in vivo analysis revealed that Dga3 has the activity of acyltransferase.

To uncover why oleaginous yeast R. toruloides behave a soluble acyltransferase for TAG biosynthesis, we tried to re-evaluate its intracellular function. Surprisingly, bioinformatics analysis revealed that Dga3 is the unique ortholog of S. cerevisiae Δ-pyrroline-5-carboxylate dehydrogenase (EC 1.5.1.12, Put2p, NP_011902.1, 46.1% identity), catalyzing the oxidation of pyrroline-5-carboxylate to glutamate in proline utilization pathway (Brandriss, 1983; Krzywicki and Brandriss, 1984). This suggests a potential function of Dga3 in proline utilization pathway.

Drop assay showed the growth defects of dga3 null mutant (Δdga3) if cultured in media with the sole nitrogen source of proline, where cell propagation of Δdga3 was completely eliminated if proline was used as the unique carbon and nitrogen source (FIG. 9B). However, supplementation of an alternative nitrogen source (urea) or the enzymatic products of Put2p (glutamate or arginine) (Brandriss and Magasanik, 1979) showed little growth defects on Δdga3 (FIG. 9A). Collectively, R. toruloides Dga3 is a bi-functional enzyme, acyltransferase and $\Delta^1$-pyrroline-5-carboxylate dehydrogenase.

Example 8

Metabolic Engineering of R. toruloides to Produce Fatty Alcohol

To identify the industrial application of lipid-less quadruple mutant dlad, as a principle of proof, fatty alcohols, one of the important oleochemicals, was designed to be produced in the oleaginous yeast R. toruloides. Till now, the most efficient fatty alcohol conversion enzyme is fatty acyl-CoA reductase from M. aquaeolei VT8 (Maqu_2220) (Liu et al., 2013a; Willis et al., 2011). A new Maqu_2220 encoding gene was designed based on the codon bias of R. toruloides (designated RtFAR1; SEQ ID NO:13), driven under three strong endogenous promoters with different regulatory profiles such as the lipid accumulation-correlated promoter of perilipin gene (PLN1in; SEQ ID NO:15) and two constitutive promoters of glyceraldehyde-3-phosphate dehydrogenase gene (GPD1) (Liu et al., 2013b; SEQ ID NO:16) and elongation factor 1α gene (TEF1in; SEQ ID NO:17) (FIG. 10A). The triple fused RtFAR1 expression cassettes were integrated into the CAR2-locus of R. toruloides wild type and dlad quadruple mutant strains, in which the position effects of ectopic integrations were eliminated (Liu et al., 2015). TLC separation and GC-MS analysis confirmed the formation of fatty alcohols, dominantly in C16-OH (palmityl alcohol) and C18-OH (stearyl alcohol), with small amount of C18:1-OH (oleyl alcohol) (FIG. 11B and FIG. 10B). Surprisingly, fatty alcohols produced in R. toruloides ATCC 10657 were dominantly distributed within the cells (FIG. 11B), against dominant extracellular distribution in another R. toruloides strain, CECT 13085 (Fillet et al., 2015). Under shaking flask fermentation in GJm3 medium, a simple and excellent lipid-producing medium routinely used in our lab, the titer of fatty alcohol from strain ATCC 10657 were lower than that from strain CECT 13085 (Fillet et al., 2015), about 0.3 g/L (FIG. 11B). As expected, quadruple disruption of DGAT genes could significantly improve the yields of fatty alcohols by 5 fold (0.8 g/L, FIG. 11B). Surprisingly, simple disruption of Δ12,15-bifunctional fatty acid desaturase gene (FAD2, our unpublished data) could also result in a similar yield (FIG. 11B). Further block of fatty acid β-oxidation pathway by disruption of the most effective peroxisomal acyl-CoA oxidase isozyme (Pox1, our unpublished data) resulted in 1.8-fold improvement in fatty alcohol titer, reaching 1.4 g/L (FIG. 11B). However, the combined disruption of DGAT genes, POX1 and FAD2 in the sextuple mutant (dga1lro1are1dga3pox1fad2, dladpf) led to a significant decrease in fatty alcohol titer, even lower than the use of WT as the host strain (FIG. 11B).

To clarify why different strain of R. toruloides produced different titers of fatty alcohol and to further improve the yields, we optimized the media with the best engineering strain dladpFAR1. Based on the basal media used previously (Fillet et al., 2015), we firstly studied the effects of different carbon (glucose and sucrose) and organic nitrogen sources (yeast extract and corn steep liquid). Four media, named as SY, DY, SC and DC, showed significant differences on fatty alcohol production (FIGS. 12A and 12B). As compared to the low effects of carbon source, nitrogen source affected greatly on product titers, in which two yeast extract-containing media, SY and DY, resulted in extremely high titer of fatty alcohol (11.5 and 12.4 g/L, respectively), and 37% and 30% of which is secreted into the media, respectively (FIG. 9B). Production in medium DY also achieved the highest productivity of 0.1 g/L/h, occupied about 42% of cell dry weight (data not shown), and BODIPY staining and lipid profiling showed that the residual cells still kept a low lipid content state (FIG. 10C).

BIBLIOGRAPHY

Athenstaedt, K., 2011. YALI0E32769g (DGA1) and YALI0E16797g (LRO1) encode major triacylglycerol synthases of the oleaginous yeast *Yarrowia lipolytica*. Biochimica et biophysica acta. 1811, 587-96.

Beopoulos, A., Haddouche, R., Kabran, P., Dulermo, T., Chardot, T., Nicaud, J. M., 2012. Identification and characterization of DGA2, an acyltransferase of the DGAT1 acyl-CoA:diacylglycerol acyltransferase family in the oleaginous yeast *Yarrowia lipolytica*. New insights into the storage lipid metabolism of oleaginous yeasts. Applied microbiology and biotechnology. 93, 1523-37.

Biermann, U., Bornscheuer, U., Meier, M. A., Metzger, J. O., Schafer, H. J., 2011. Oils and fats as renewable raw materials in chemistry. Angew Chem Int Ed Engl. 50, 3854-71.

Brandriss, M. C., 1983. Proline utilization in *Saccharomyces cerevisiae*: analysis of the cloned PUT2 gene. Mol Cell Biol. 3, 1846-56.

Brandriss, M. C., 1987. Evidence for positive regulation of the proline utilization pathway in *Saccharomyces cerevisiae*. Genetics. 117, 429-35.

Brandriss, M. C., Magasanik, B., 1979. Genetics and physiology of proline utilization in *Saccharomyces cerevisiae*: enzyme induction by proline. Journal of bacteriology. 140, 498-503.

Cai, L., Sun, L., Fu, L., Ji, L., 2009. media compositions, selection methods and *agrobacterium* strains for transformation of plants. PCT patent. WO 2011068468 A1.

Carlsson, A. S., Yilmaz, J. L., Green, A. G., Stymne, S., Hofvander, P., 2011. Replacing fossil oil with fresh oil— with what and for what? Eur J Lipid Sci Technol. 113, 812-831.

Chi, X., Hu, R., Zhang, X., Chen, M., Chen, N., Pan, L., Wang, T., Wang, M., Yang, Z., Wang, Q., Yu, S., 2014. Cloning and functional analysis of three diacylglycerol acyltransferase genes from peanut (*Arachis hypogaea* L.). PLoS One. 9, e105834.

Coleman, R. A., Lee, D. P., 2004. Enzymes of triacylglycerol synthesis and their regulation. Progress in lipid research. 43, 134-76.

Czabany, T., Athenstaedt, K., Daum, G., 2007. Synthesis, storage and degradation of neutral lipids in yeast. Biochimica et biophysica acta. 1771, 299-309.

Dahlqvist, A., Stahl, U., Lenman, M., Banas, A., Lee, M., Sandager, L., Ronne, H., Stymne, S., 2000. Phospholipid: diacylglycerol acyltransferase: an enzyme that catalyzes the acyl-CoA-independent formation of triacylglycerol in yeast and plants. Proceedings of the National Academy of Sciences. 97, 6487-6492.

Elsey, D., Jameson, D., Raleigh, B., Cooney, M. J., 2007. Fluorescent measurement of microalgal neutral lipids. J Microbiol Methods. 68, 639-42.

Fillet, S., Gibert, J., Suarez, B., Lara, A., Ronchel, C., Adrio, J. L., 2015. Fatty alcohols production by oleaginous yeast. Journal of industrial microbiology & biotechnology. 42, 1463-72.

Gangar, A., Karande, A. A., Rajasekharan, R., 2001. Isolation and localization of a cytosolic 10 S triacylglycerol biosynthetic multienzyme complex from oleaginous yeast. The Journal of biological chemistry. 276, 10290-8.

Govender, T., Ramanna, L., Rawat, I., Bux, F., 2012. BODIPY staining, an alternative to the Nile Red fluorescence method for the evaluation of intracellular lipids in microalgae. Bioresource Technology. 114, 507-511.

Gunstone, F. D., Harwood, J. L., Dijkstra, A. J., 2012. The lipid handbook with CD-ROM. CRC Press.

Haushalter, R. W., Groff, D., Deutsch, S., The, L., Chavkin, T. A., Brunner, S. F., Katz, L., Keasling, J. D., 2015. Development of an orthogonal fatty acid biosynthesis system in *E. coli* for oleochemical production. Metab Eng. 30, 1-6.

Hofvander, P., Doan, T. T., Hamberg, M., 2011. A prokaryotic acyl-CoA reductase performing reduction of fatty acyl-CoA to fatty alcohol. FEBS Lett. 585, 3538-43.

Jin, G., Zhang, Y., Shen, H., Yang, X., Xie, H., Zhao, Z. K., 2013. Fatty acid ethyl esters production in aqueous phase by the oleaginous yeast *Rhodosporidium toruloides*. Bioresour Technol. 150, 266-70.

Kalscheuer, R., Steinbuchel, A., 2003. A novel bifunctional wax ester synthase/acyl-CoA:diacylglycerol acyltransferase mediates wax ester and triacylglycerol biosynthesis in *Acinetobacter calcoaceticus* ADP1. The Journal of biological chemistry. 278, 8075-82.

Keasling, J. D., 2010. Manufacturing molecules through metabolic engineering. Science. 330, 1355-8.

Koh, C. M., Liu, Y., Du, M., Ji, L., 2014. Molecular characterization of KU70 and KU80 homologues and exploitation of a KU70-deficient mutant for improving gene deletion frequency in *Rhodosporidium toruloides*. BMC Microbiology. 14, 50.

Krzywicki, K. A., Brandriss, M. C., 1984. Primary structure of the nuclear PUT2 gene involved in the mitochondrial pathway for proline utilization in *Saccharomyces cerevisiae*. Mol Cell Biol. 4, 2837-42.

Lazo, G. R., Stein, P. A., Ludwig, R. A., 1991. A DNA transformation-competent *Arabidopsis* genomic library in *Agrobacterium*. Biotechnology (N Y). 9, 963-7.

Liu, A., Tan, X., Yao, L., Lu, X., 2013a. Fatty alcohol production in engineered *E. coli* expressing *Marinobacter* fatty acyl-CoA reductases. Applied microbiology and biotechnology. 97, 7061-71.

Liu, H., Zhao, X., Wang, F., Li, Y., Jiang, X., Ye, M., Zhao, Z. K., Zou, H., 2009. Comparative proteomic analysis of *Rhodosporidium toruloides* during lipid accumulation. Yeast. 26, 553-66.

Liu, Y., Koh, C. M., Sun, L., Hlaing, M. M., Du, M., Peng, N., Ji, L., 2013b. Characterization of glyceraldehyde-3-phosphate dehydrogenase gene RtGPD1 and development of genetic transformation method by dominant selection in oleaginous yeast *Rhodosporidium toruloides*. Appl Microbiol Biotechnol. 97, 719-29.

Liu, Y., Koh, C. M., Sun, L., Ji, L., 2011. Tartronate semialdehyde reductase defines a novel rate-limiting step in assimilation and bioconversion of glycerol in *Ustilago maydis*. PLoS One. 6, e16438.

Liu, Y., Koh, C. M. J., Ngoh, S. T., Ji, L., 2015. Engineering an efficient and tight d-amino acid-inducible gene expression system in *Rhodosporidium/Rhodotorula* species. Microbial Cell Factories. 14, 170-185.

Lung, S. C., Weselake, R. J., 2006. Diacylglycerol acyltransferase: a key mediator of plant triacylglycerol synthesis. Lipids. 41, 1073-88.

Mysara, M. et al. (2011). MysiRNA-designer: a workflow for efficient siRNA design. PLOS one 6(10):e25642.

Noweck, K., Grafahrend, W., Fatty alcohols. Ullmann's encyclopedia of industrial chemistry. Wiley-VCH KGaA, Weinheim, 2000.

Oelkers, P., Tinkelenberg, A., Erdeniz, N., Cromley, D., Billheimer, J. T., Sturley, S. L., 2000. A lecithin cholesterol acyltransferase-like gene mediates diacylglycerol esterification in yeast. The Journal of biological chemistry. 275, 15609-12.

Paul, D., Magbanua, Z., Arick, M., 2nd, French, T., Bridges, S. M., Burgess, S. C., Lawrence, M. L., 2014. Genome Sequence of the Oleaginous Yeast *Rhodotorula glutinis* ATCC 204091. Genome announcements. 2.

Pfleger, B. F., Gossing, M., Nielsen, J., 2015. Metabolic engineering strategies for microbial synthesis of oleochemicals. Metab Eng. 29, 1-11.

Ran, F. Ann, et al. (2013). Double nicking by RNA-guided CRISPR Cas9 for enhanced genome editing specificity. Cell 154:1380-1389.

Rani, S. H., Saha, S., Rajasekharan, R., 2013. A soluble diacylglycerol acyltransferase is involved in triacylglycerol biosynthesis in the oleaginous yeast *Rhodotorula glutinis*. Microbiology. 159, 155-66.

Ratledge, C., Wilkinson, S., 1988a. An overview of microbial lipids. Microbial lipids. 1, 3-22.

Ratledge, C., Wilkinson, S. G., 1988b. Microbial lipids. Academic Press London.

Ratledge, C., Wynn, J. P., 2002. The biochemistry and molecular biology of lipid accumulation in oleaginous microorganisms. Adv Appl Microbiol. 51, 1-51.

Raychaudhuri, S., Reddy, M. M., Rajkumar, N. R., Rajasekharan, R., 2003. Cytosolic iron superoxide dismutase is a part of the triacylglycerol biosynthetic complex in oleaginous yeast. The Biochemical journal. 372, 587-94.

Sampaio, J. P., Gadanho, M., Bauer, R., Weiß, M., 2003. Taxonomic studies in the Microbotryomycetidae: *Leucosporidium golubevii* sp. nov., *Leucosporidiella* gen. nov. and the new orders Leucosporidiales and Sporidiobolales. Mycol Prog. 2, 53-68.

Sorger, D., Daum, G., 2002. Synthesis of triacylglycerols by the acyl-coenzyme A:diacyl-glycerol acyltransferase Dga1p in lipid particles of the yeast *Saccharomyces cerevisiae*. Journal of bacteriology. 184, 519-24.

Sorger, D., Daum, G., 2003. Triacylglycerol biosynthesis in yeast. Applied microbiology and biotechnology. 61, 289-99.

Szymanski, K. M., Binns, D., Bartz, R., Grishin, N. V., Li, W.-P., Agarwal, A. K., Garg, A., Anderson, R. G. W., Goodman, J. M., 2007. The lipodystrophy protein seipin is found at endoplasmic reticulum lipid droplet junctions and is important for droplet morphology. Proceedings of the National Academy of Sciences. 104, 20890-20895.

Tang, X., Chen, W. N., 2015. Enhanced production of fatty alcohols by engineering the TAGs synthesis pathway in *Saccharomyces cerevisiae*. Biotechnol Bioeng. 112, 386-92.

Turchetto-Zolet, A. C., Maraschin, F. S., de Morais, G. L., Cagliari, A., Andrade, C. M., Margis-Pinheiro, M., Margis, R., 2011. Evolutionary view of acyl-CoA diacylglycerol acyltransferase (DGAT), a key enzyme in neutral lipid biosynthesis. BMC evolutionary biology. 11,263.

Turcotte, G., Kosaric, N., 1988. Biosynthesis of lipids by *Rhodosporidium toruloides* ATCC 10788. J Biotechnol. 8, 221-237.

Voelker, T. A., Davies, H. M., 1994. Alteration of the specificity and regulation of fatty acid synthesis of *Escherichia coli* by expression of a plant medium-chain acyl-acyl carrier protein thioesterase. J Bacteriol. 176, 7320-7.

Wang, S. S., Brandriss, M. C., 1987. Proline utilization in *Saccharomyces cerevisiae*: sequence, regulation, and mitochondrial localization of the PUT1 gene product. Mol Cell Biol. 7, 4431-40.

Wesley, S. V. et al. (2001). Construct design for efficient, effective and high-throughput gene silencing in plants. Plant J 27:581-590.

Willis, R. M., Wahlen, B. D., Seefeldt, L. C., Barney, B. M., 2011. Characterization of a fatty acyl-CoA reductase from *Marinobacter aquaeolei* VT8: a bacterial enzyme catalyzing the reduction of fatty acyl-CoA to fatty alcohol. Biochemistry. 50, 10550-8.

Yang, F., Zhang, S., Zhou, Y. J., Zhu, Z., Lin, X., Zhao, Z. K., 2012. Characterization of the mitochondrial NAD(+)-dependent isocitrate dehydrogenase of the oleaginous yeast *Rhodosporidium toruloides*. Applied microbiology and biotechnology.

Yen, C. L., Stone, S. J., Koliwad, S., Harris, C., Farese, R. V., Jr., 2008. Thematic review series: glycerolipids. DGAT enzymes and triacylglycerol biosynthesis. Journal of lipid research. 49, 2283-301.

Yan, P. et al. (2012). High-throughput construction of intron-containing hairpin RNA vectors for RNAi in plants. PLOS one 7(5):e38186.

Yoon, K., Han, D., Li, Y., Sommerfeld, M., Hu, Q., 2012. Phospholipid:diacylglycerol acyltransferase is a multifunctional enzyme involved in membrane lipid turnover and degradation while synthesizing triacylglycerol in the unicellular green microalga *Chlamydomonas reinhardtii*. The Plant cell. 24, 3708-24.

Youngquist, J. T., Schumacher, M. H., Rose, J. P., Raines, T. C., Politz, M. C., Copeland, M. F., Pfleger, B. F., 2013. Production of medium chain length fatty alcohols from glucose in *Escherichia coli*. Metab Eng. 20, 177-86.

Youssef, L., Avalos, J., 2007. Genetic basis of the ovc phenotype of *Neurospora*: identification and analysis of a 77 kb deletion. Current genetics. 51, 19-30.

Zhao, X., Wu, S., Hu, C., Wang, Q., Hua, Y., Zhao, Z. K., 2010. Lipid production from Jerusalem artichoke by *Rhodosporidium toruloides* Y4. J Ind Microbiol Biotechnol. 37, 581-5.

Zheng, Y. N., Li, L. L., Liu, Q., Yang, J. M., Wang, X. W., Liu, W., Xu, X., Liu, H., Zhao, G., Xian, M., 2012. Optimization of fatty alcohol biosynthesis pathway for selectively enhanced production of C12/14 and C16/18 fatty alcohols in engineered *Escherichia coli*. Microb Cell Fact. 11, 65.

What is claimed is:

1. A genetically modified fungal cell useful for producing fatty alcohols that comprises:
   (a) a nucleic acid construct for overexpression of a heterologous fatty acyl-CoA reductase (FAR), wherein the nucleic acid construct for overexpressing the heterologous FAR comprises multiple copies of a nucleic acid encoding the heterologous FAR, wherein each copy of the nucleic acid encoding the heterologous FAR is operably linked to a different strong constitutive promoter, wherein the heterologous FAR has the amino acid sequence set forth in SEQ ID NO: 14, and wherein the overexpression of the heterologous FAR is in comparison to the corresponding non-genetically modified fungal cell;
   (b) a deletion in an endogenous gene encoding a type 1 acyl-CoA:diacylglycerol acyltransferase (Dga1);
   (c) a deletion in an endogenous gene encoding a type 2 phospholipid:diacylglycerol acyltransferase (Lro1);
   (d) a deletion in an endogenous gene encoding an acyl-CoA:sterol acyltransferase (steryl ester synthase, Are1); and
   (e) a deletion in an endogenous gene encoding a type 3 soluble acyltransferase (Dga3),
   wherein the fungal cell is from a *Rhodosporidium* species or a *Rhodotorula* species.

2. The genetically modified fungal cell of claim 1, further comprising a deletion in an endogenous gene encoding an acyl-CoA oxidase 1 (Pox1).

3. The genetically modified fungal cell of claim 1, wherein the fungal cell is a strain of *Rhodosporidium toruloides*.

4. The genetically modified fungal cell of claim 1, wherein FAR is encoded by a nucleic acid having the nucleotide sequence set forth in SEQ ID NO:13.

5. The genetically modified fungal cell of claim 1, wherein the nucleic acid construct comprises three copies of the nucleic acid encoding the heterologous FAR.

6. The genetically modified fungal cell of claim 5, wherein the strong constitutive promoters are a RtPLN1$_{in}$ promoter having the nucleotide sequence set forth in SEQ ID NO:15, a RtGPD1 promoter having the nucleotide sequence set forth in SEQ ID NO:16, and a RtTEF1$_{in}$ promoter having the nucleotide sequence set forth in SEQ ID NO:17.

7. The genetically modified fungal cell of claim 3, wherein the strain of *Rhodosporidium toruloides* is *Rhodosporidium toruloides* ATCC 10657.

8. The genetically modified fungal cell of claim 2, wherein the fungal cell is a strain of *Rhodosporidium toruloides*.

9. The genetically modified fungal cell of claim 8, wherein the strain of *Rhodosporidium toruloides* is *Rhodosporidium toruloides* ATCC 10657.

10. The genetically modified fungal cell of claim 2, wherein the nucleic acid construct comprises three copies of the nucleic acid encoding the heterologous FAR.

11. The genetically modified fungal cell of claim 10, wherein the strong constitutive promoters are a RtPLN1$_{in}$ promoter having the nucleotide sequence set forth in SEQ ID NO:15, a RtGPD1 promoter having the nucleotide sequence set forth in SEQ ID NO:16, and a RtTEF1$_{in}$ promoter having the nucleotide sequence set forth in SEQ ID NO:17.

12. The genetically modified fungal cell of claim 1, wherein
   Dga1 has the amino acid sequence set forth in SEQ ID NO:6,
   Lro1 has the amino acid sequence set forth in SEQ ID NO:8,
   Are1 has the amino acid sequence set forth in SEQ ID NO:10, and
   Dga3 has the amino acid sequence set forth in SEQ ID NO:12.

13. The genetically modified fungal cell of claim 12, wherein
   Dga1 is encoded by a nucleic acid having the nucleotide sequence set forth in SEQ ID NO:5,
   Lro1 is encoded by a nucleic acid having the nucleotide sequence set forth in SEQ ID NO:7,
   Are1 is encoded by a nucleic acid having the nucleotide sequence set forth in SEQ ID NO:9, and
   Dga3 is encoded by a nucleic acid having the nucleotide sequence set forth in SEQ ID NO:11.

14. The genetically modified fungal cell of claim 2, wherein
   Dga1 has the amino acid sequence set forth in SEQ ID NO:6,
   Lro1 has the amino acid sequence set forth in SEQ ID NO:8,
   Are1 has the amino acid sequence set forth in SEQ ID NO:10,
   Dga3 has the amino acid sequence set forth in SEQ ID NO:12, and,
   Pox1 has the amino acid sequence set forth in SEQ ID NO:61.

15. The genetically modified fungal cell of claim 14, wherein
   Dga1 is encoded by a nucleic acid having the nucleotide sequence set forth in SEQ ID NO:5,
   Lro1 is encoded by a nucleic acid having the nucleotide sequence set forth in SEQ ID NO:7,
   Are1 is encoded by a nucleic acid having the nucleotide sequence set forth in SEQ ID NO:9,
   Dga3 is encoded by a nucleic acid having the nucleotide sequence set forth in SEQ ID NO:11; and
   Pox1 is encoded by a nucleic acid having the nucleotide sequence set forth in SEQ ID NO:60.

16. A method of producing fatty alcohols comprising culturing the genetically modified fungal cell of claim 1 under conditions suitable for growth of the modified fungal cell and for production of fatty alcohols.

17. The method of claim 16, wherein the culturing is performed using a medium comprising glucose, yeast extract, $K_2HP_4$, $NH_4N_3$, $MgSO_4.7H_2O$, and $CaCl_2.2H_2O$.

18. The method of claim 17, wherein the culturing is performed using a medium comprising per litre: 100 g glucose, 22.5 g yeast extract, 0.75 g $K_2HPO_4$, 0.7 g $NH_4NO_3$, 0.4 g $MgSO_4.7H_2O$, and 0.4 g $CaCl_2H_2O$.

* * * * *

UNITED STATES PATENT AND TRADEMARK OFFICE
CERTIFICATE OF CORRECTION

PATENT NO. : 11,034,981 B2
APPLICATION NO. : 16/484322
DATED : June 15, 2021
INVENTOR(S) : Lianghui Ji et al.

Page 1 of 1

It is certified that error appears in the above-identified patent and that said Letters Patent is hereby corrected as shown below:

In the Claims

Column 108, Claim 17, Line 67, "$K_2HP_4$" should be --$K_2HPO_4$--.

Column 108, Claim 17, Line 67, "$NH_4N_3$" should be --$NH_4NO_3$--.

Signed and Sealed this
First Day of March, 2022

Drew Hirshfeld
*Performing the Functions and Duties of the*
*Under Secretary of Commerce for Intellectual Property and*
*Director of the United States Patent and Trademark Office*